US011932858B2

(12) United States Patent
Meyers et al.

(10) Patent No.: US 11,932,858 B2
(45) Date of Patent: Mar. 19, 2024

(54) HOMOLOGOUS RECOMBINATION VIA TRANSCRIPTIONAL ACTIVATION

(71) Applicant: DONALD DANFORTH PLANT SCIENCE CENTER, St. Louis, MO (US)

(72) Inventors: Blake Meyers, St. Louis, MO (US); Rebecca Bart, St. Louis, MO (US); Kira Veley, St. Louis, MO (US); Ihuoma Okwuonu, St. Louis, MO (US)

(*) Notice: Subject to any disclaimer, the term of this patent is extended or adjusted under 35 U.S.C. 154(b) by 518 days.

(21) Appl. No.: 16/772,574

(22) PCT Filed: Dec. 14, 2018

(86) PCT No.: PCT/US2018/065756

§ 371 (c)(1),
(2) Date: Jun. 12, 2020

(87) PCT Pub. No.: WO2019/118879

PCT Pub. Date: Jun. 20, 2019

(65) Prior Publication Data

US 2020/0392517 A1 Dec. 17, 2020

Related U.S. Application Data

(60) Provisional application No. 62/598,831, filed on Dec. 14, 2017.

(51) Int. Cl.
*C12N 15/66* (2006.01)
*C12N 15/115* (2010.01)

(52) U.S. Cl.
CPC ............ *C12N 15/66* (2013.01); *C12N 15/115* (2013.01); *C12N 2310/20* (2017.05); *C12Q 2521/301* (2013.01)

(58) Field of Classification Search
CPC .. C12N 15/66; C12N 15/115; C12N 2310/20; C12Q 2521/301
See application file for complete search history.

(56) References Cited

U.S. PATENT DOCUMENTS

| | | | |
|---|---|---|---|
| 2015/0291967 | A1 | 10/2015 | Mathis et al. |
| 2016/0298096 | A1 | 10/2016 | Charpentier et al. |
| 2017/0071173 | A1 | 3/2017 | Lai et al. |
| 2017/0073664 | A1 | 3/2017 | McCafferty et al. |
| 2017/0204388 | A1 | 7/2017 | Donohoue et al. |

FOREIGN PATENT DOCUMENTS

| | | | |
|---|---|---|---|
| WO | 2011130345 | A1 | 10/2011 |

OTHER PUBLICATIONS

Albani D., et al., "The Wheat Transcriptional Activator SPA: A Seed-Specific bZIP Protein That Recognizes the GCN4-like Motif in the Bifactorial Endosperm Box of Prolamin Genes," The Plant Cell, Feb. 1997, vol. 9, pp. 171-184.

Anderson O.D., et al., "Nucleotide Sequences of the Two High-Molecular-Weight Glutenin Genes from the D-Genome of a Hexaploid Bread Wheat, *Triticum aestivum* L. *Cv Cheyenne*," Nucleic Acids Research, 1989, vol. 17, No. 1, 2 pages.

Crasto C.J., et al., "Linker: a Program to Generate Linker Sequences for Fusion Proteins," Protein Engineering, 2000, vol. 13, No. 5, pp. 309-312.

Cummins I., et al., "eDNA Sequence of a Sunflower Oleosin and Transcript Tissue Specificity," Plant Molecular Biology, 1992, vol. 19, pp. 873-876.

Ellis J.R., et al., "Tissue-Specific Expression of a Pea Legumin Gene in Seeds of *Nicotiana plumbaginifolia*," Plant Molecular Biology, 1988, vol. 10, pp. 203-214.

Gotor C., et al., "Analysis of Three Tissue-Specific Elements from the Wheat Cab-1 Enhancer," The Plant Journal, 1993, vol. 3, No. 4, pp. 509-518.

Gribskov M., et al., "Sigma Factors from *E.coli*, B.subtils, phage SPOI, and phage T4 are Lomologous Proteins," Nucleic Acids Research, 1986, vol. 14(16), pp. 6745-6763.

International Preliminary Report on Patentability for International Application No. PCT/US2018/065756, dated Jun. 25, 2020, 10 pages.

International Search Report and Written Opinion for International Application No. PCT/US2018/065756, dated May 7, 2019, 14 pages.

Kwon H-B., et al., "Identification of a Light-Responsive Region of the Nuclear Gene Encoding the B Subunit of Chloroplast Glyceraldehyde 3-Phosphate Dehydrogenase F Rotn *Arabidopsis thaliana*1," Plant Physiology, 1994, vol. 105, pp. 357-367.

Lange A., et al., "Classical Nuclear Localization Signals: Definition, Function, and Interaction with Importin a*,s," Journal of Biological Chemistry, Feb. 23, 2007, vol. 282(8), pp. 5101-5105.

Liu Y., et al., "In Vitro CRISPR/Cas9 System for Efficient Targeted DNA Editing," ASM Journals, Nov. 2015, vol. 6, No. 6, 8 pages.

Lombardo A., et al., "Gene Editing in Human Stem Cells Using Zinc Finger Nucleases and Integrase-Defective Lentiviral Vector Delivery," Nature Biotechnology, Oct. 28, 2007, 9 pages.

Matsuoka M., et al., "Tissue-Specific Light-Regulated Expression Directed by the Promoter of a C4 Gene, Maize Pyruvate, Orthophosphate Dikinase, in a C3 Plant, Rice," Proceedings of the National Academy of Sciences of the United States of America, Oct. 1993, vol. 90, pp. 9586-9590.

Mena M., et al., "An Endosperm-Specific DOF Protein from Barley, Highly Conserved in Wheat, Binds to and Activates Transcription from the Prolamin-Box of a Native B-Hordein Promoter in Barley Endosperm," The Plant Journal, 1998, vol. 16, No. 1, pp. 53-62.

Moehle E.A., et al., "Targeted Gene Addition into a Specified Location in the Human Genome Using Designed Zinc Finger Nucleases," Proceedings of the National Academy of Sciences of the United States of America, Feb. 27, 2007, vol. 104, No. 9, pp. 3055-3060.

(Continued)

*Primary Examiner* — J. E. Angell

(57) ABSTRACT

Compositions and methods for efficiently generating and identifying accurate homologous recombination events are disclosed.

20 Claims, 10 Drawing Sheets

Specification includes a Sequence Listing.

(56) References Cited

OTHER PUBLICATIONS

Muller M., et al., "The Nitrogen Response of a Barley C-Hordein Promoter is Controlled by Positive and Negative Regulation of the GCN4 and Endosperm Box," The Plant Journal, 1993, vol. 4, No. 2, pp. 343-355.
Opsahi-Ferstad H-G., et al., "ZmEsr, a Novel Endosperm-Specific Gene Expressed in a Restricted Region around the Maize Embryo," The Plant Journal, 1997, vol. 12, No. 1, pp. 235-246.
Orozco B.M., et al., "Localization of Light-Inducible and Tissue-Specific Regions of the Spinach Ribulose Bisphosphate Carboxylase/Oxygenase (Rubisco) Activase Promoter in Transgenic Tobacco Plants," Plant Molecular Biology, 1993, vol. 23, pp. 1129-1138.
Santiago Y., et al., "Targeted Gene Knockout in Mammalian Cells by Using Engineered Zinc-Finger Nucleases," Proceedings of the National Academy of Sciences of the United States of America, Apr. 15, 2008, vol. 105, No. 15, pp. 5809-5814.
Sato Y., et al., "A Rice Homeobox Gene, OSHJ, Is Expressed Before Organ Differentiation in a Specific Region during Early Embryogenesis," Proceedings of the National Academy of Sciences of the United States of America, Jul. 1996, vol. 93, pp. 8117-8122.
Scotfield S.R., et al., "Nucleotide Sequence of a Member of the Napin Storage Protein Family from *Brassica napus*," The Journal of Biological Chemistry, Sep. 5, 1967, vol. 262, No. 25, pp. 12202-12208.
Takaiwa F., et al., "Nucleotide Sequence of a Rice Glutelin Gene," FEBS Letters, Aug. 1987, vol. 22, No. 1, pp. 43-47.
Taylor N., et al., "A High-throughput Platform for the Production and Analysis of Transgenic Cassava," Tropical Plant Biology, 2012, vol. 5, pp. 127-139.
Twell D., et al., "Isolation and Expression of an Anther-Specific Gene from Tomato," Molecular Genetics and Genomics, 1989, vol. 217, pp. 240-245.
Van Der Meer I.M., et al., "Promoter Analysis of the Chalcone Synthase (chsA) Gene of Petunia Hybrida: A 67 Bp Promoter Region Directs Flower-Specific Expression," Plant Molecular Biology, 1990, vol. 15, pp. 95-109.
Vicente-Carbajosa J., et al., "Barley BLZ1: A bZIP Transcriptional Activator That Interacts with Endosperm-Specific Gene Promoters," The Plant Journal, 1998, vol. 13, No. 5, pp. 629-640.
Wilson M.C., et al., "Gene Expression Atlas for the Food Security Crop Cassava," New Phytologist, 2017, vol. 213, pp. 1632-1641.
Wu L.S.H., et al., "Genomic Cloning of 18 kDa Oleosin and Detection of Triacylglycerols and Oleosin Isoforms in Maturing Rice and Postgerminative Seedlings," Journal of Biochemistry, 1998, vol. 123, pp. 386-391.
Yamamoto Y.Y., et al., "Light-Responsive Elements of the Tobacco PSI-D Gene are Located both Upstream and within the Transcribed Region," The Plant Journal, 1997, vol. 12, No. 2, pp. 255-265.
Yoshioka N., et al., "Efficient Generation of Human iPSCs by a Synthetic Self-Replicative RNA," Cell Stem Cell, Aug. 1, 2013, vol. 13, pp. 246-254.

SEQUENCE LISTING

<160> NUMBER OF SEQ ID NOS: 15

<210> SEQ ID NO 1
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 1

Pro Lys Lys Lys Arg Lys Val
1 5

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Pro Lys Lys Lys Arg Arg Val
1 5

<210> SEQ ID NO 3
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 3

Lys Arg Pro Ala Ala Thr Lys Lys Ala Gly Gln Ala Lys Lys Lys Lys
1 5 10 15

<210> SEQ ID NO 4
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 4

Gly Arg Lys Lys Arg Arg Gln Arg Arg Arg Pro Pro Gln Pro Lys Lys
1 5 10 15

Lys Arg Lys Val
20

<210> SEQ ID NO 5
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 5

Pro Leu Ser Ser Ile Phe Ser Arg Ile Gly Asp Pro Pro Lys Lys Lys
1 5 10 15

Arg Lys Val

<210> SEQ ID NO 6
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 6

Gly Ala Leu Phe Leu Gly Trp Leu Gly Ala Ala Gly Ser Thr Met Gly
1 5 10 15

Ala Pro Lys Lys Lys Arg Lys Val
20

<210> SEQ ID NO 7
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 7

Gly Ala Leu Phe Leu Gly Phe Leu Gly Ala Ala Gly Ser Thr Met Gly
1 5 10 15

Ala Trp Ser Gln Pro Lys Lys Lys Arg Lys Val
20 25

<210> SEQ ID NO 8
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 8

Lys Glu Thr Trp Trp Glu Thr Trp Trp Thr Glu Trp Ser Gln Pro Lys
1 5 10 15

Lys Lys Arg Lys
20

<210> SEQ ID NO 9
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 9

Gly Gly Ser Gly Gly Gly Ser Gly
1 5

<210> SEQ ID NO 10
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 10

Gly Gly Gly Gly Ser
1 5

<210> SEQ ID NO 11
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 11

Glu Ala Ala Ala Lys
1 5

<210> SEQ ID NO 12
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 12

Ala Glu Ala Ala Ala Lys
1               5

<210> SEQ ID NO 13
<211> LENGTH: 18142
<212> TYPE: DNA
<213> ORGANISM: Artificial Sequence
<220> FEATURE:
<223> OTHER INFORMATION: SYNTHESIZED

<400> SEQUENCE: 13
agtgtggcac tggccgtcgt tttacaacgt cgtgactggg aaaaccctgg cgttacccaa 60
cttaatcgcc ttgcagcaca tccccctttc gccagctggc gtaatagcga agaggcccgc 120
accgatcgcc cttcccaaca gttgcgcagc ctgaatggcg aatgctagag cagcttgagc 180
ttggatcaga ttgtcgtttc ccgccttcag tttaaactat cagtgtttga caggatatat 240
tggcgggtaa acctaagaga aaagagcgtt tattagaata atcggatatt taaaagggcg 300
tgaaaaggtt tatccgttcg tccatttgta tgtgcatgcc aaccacaggg ttcccctcgg 360
gatcaaagta ctttgatcca acccctccgc tgctatagtg cagtcggctt ctgacgttca 420
gtgcagccgt cttctgaaaa cgacatgtcg cacaagtcct aagttacgcg acaggctgcc 480
gccctgccct tttcctggcg ttttcttgtc gcgtgtttta gtcgcataaa gtagaatact 540
tgcgactaga accggagaca ttacgccatg aacaagagcg ccgccgctgg cctgctgggc 600
tatgcccgcg tcagcaccga cgaccaggac ttgaccaacc aacgggccga actgcacgcg 660
gccggctgca ccaagctgtt ttccgagaag atcaccggca ccaggcgcga ccgcccggag 720
ctggccagga tgcttgacca cctacgccct ggcgacgttg tgacagtgac caggctagac 780
cgcctggccc gcagcacccg cgacctactg gacattgccg agcgcatcca ggaggccggc 840
gcgggcctgc gtagcctggc agagccgtgg gccgacacca ccacgccggc cggccgcatg 900
gtgttgaccg tgttcgccgg cattgccgag ttcgagcgtt ccctaatcat cgaccgcacc 960
cggagcgggc gcgaggccgc caaggcccga ggcgtgaagt ttggcccccg ccctaccctc 1020
accccggcac agatcgcgca cgcccgcgag ctgatcgacc aggaaggccg caccgtgaaa 1080
gaggcggctg cactgcttgg cgtgcatcgc tcgaccctgt accgcgcact tgagcgcagc 1140
gaggaagtga cgcccaccga ggccaggcgg cgcggtgcct tccgtgagga cgcattgacc 1200
gaggccgacg ccctggcggc cgccgagaat gaacgccaag aggaacaagc atgaaaccgc 1260
accaggacgg ccaggacgaa ccgtttttca ttaccgaaga gatcgaggcg gagatgatcg 1320
cggccgggta cgtgttcgag ccgcccgcgc acggctcaac cgtgcggctg catgaaatcc 1380
tggccggttt gtctgatgcc aagctggcgg cctggccggc cagcttggcc gctgaagaaa 1440
ccgagcgccg ccgtctaaaa aggtgatgtg tatttgagta aaacagcttg cgtcatgcgg 1500
tcgctgcgta tatgatgcga tgagtaaata aacaaatacg caaggggaac gcatgaaggt 1560
tatcgctgta cttaaccaga aaggcgggtc aggcaagacg accatcgcaa cccatctagc 1620
ccgcgccctg caactcgccg gggccgatgt tctgttagtc gattccgatc cccagggcag 1680
tgcccgcgat tgggcggccg tgcgggaaga tcaaccgcta accgttgtcg gcatcgaccg 1740

-continued

```
cccgacgatt gaccgcgacg tgaaggccat cggccggcgc gacttcgtag tgatcgacgg   1800
agcgccccag gcggcggact tggctgtgtc cgcgatcaag gcagccgact tcgtgctgat   1860
tccggtgcag ccaagccctt acgacatatg ggccaccgcc gacctggtgg agctggttaa   1920
gcagcgcatt gaggtcacgg atggaaggct acaagcggcc tttgtcgtgt cgcgggcgat   1980
caaaggcacg cgcatcggcg gtgaggttgc cgaggcgctg gccgggtacg agctgcccat   2040
tcttgagtcc cgtatcacgc agcgcgtgag ctacccaggc actgccgccg ccggcacaac   2100
cgttcttgaa tcagaacccg agggcgacgc tgcccgcgag gtccaggcgc tggccgctga   2160
aattaaatca aaactcattt gagttaatga ggtaaagaga aaatgagcaa aagcacaaac   2220
acgctaagtg ccggccgtcc gagcgcacgc agcagcaagg ctgcaacgtt ggccagcctg   2280
gcagacacgc cagccatgaa gcgggtcaac tttcagttgc cggcggagga tcacaccaag   2340
ctgaagatgt acgcggtacg ccaaggcaag accattaccg agctgctatc tgaatacatc   2400
gcgcagctac cagagtaaat gagcaaatga ataaatgagt agatgaattt tagcggctaa   2460
aggaggcggc atggaaaatc aagaacaacc aggcaccgac gccgtggaat gccccatgtg   2520
tggaggaacg ggcggttggc caggcgtaag cggctgggtt gtctgccggc cctgcaatgg   2580
cactggaacc cccaagcccg aggaatcggc gtgacggtcg caaaccatcc ggcccggtac   2640
aaatcggcgc ggcgctgggt gatgacctgg tggagaagtt gaaggccgcg caggccgccc   2700
agcggcaacg catcgaggca gaagcacgcc ccggtgaatc gtggcaagcg gccgctgatc   2760
gaatccgcaa agaatcccgg caaccgccgg cagccggtgc gccgtcgatt aggaagccgc   2820
ccaagggcga cgagcaacca gattttttcg ttccgatgct ctatgacgtg ggcacccgcg   2880
atagtcgcag catcatggac gtggccgttt tccgtctgtc gaagcgtgac cgacgagctg   2940
gcgaggtgat ccgctacgag cttccagacg ggcacgtaga ggtttccgca gggccggccg   3000
gcatggccag tgtgtgggat tacgacctgg tactgatggc ggtttcccat ctaaccgaat   3060
ccatgaaccg ataccgggaa gggaagggag acaagcccgg ccgcgtgttc cgtccacacg   3120
ttgcggacgt actcaagttc tgccggcgag ccgatggcgg aaagcagaaa gacgacctgg   3180
tagaaacctg cattcggtta aacaccacgc acgttgccat gcagcgtacg aagaaggcca   3240
agaacggccg cctggtgacg gtatccgagg gtgaagcctt gattagccgc tacaagatcg   3300
taaagagcga aaccgggcgg ccggagtaca tcgagatcga gctagctgat tggatgtacc   3360
gcgagatcac agaaggcaag aacccggacg tgctgacggt tcaccccgat tactttttga   3420
tcgatcccgg catcggccgt tttctctacc gcctggcacg ccgcgccgca ggcaaggcag   3480
aagccagatg gttgttcaag acgatctacg aacgcagtgg cagcgccgga gagttcaaga   3540
agttctgttt caccgtgcgc aagctgatcg ggtcaaatga cctgccggag tacgatttga   3600
aggaggaggc ggggcaggct ggcccgatcc tagtcatgcg ctaccgcaac ctgatcgagg   3660
gcgaagcatc cgccggttcc taatgtacgg agcagatgct agggcaaatt gccctagcag   3720
gggaaaaagg tcgaaaaggc ctctttcctg tggatagcac gtacattggg aacccaaagc   3780
cgtacattgg gaaccggaac ccgtacattg ggaacccaaa gccgtacatt gggaaccggt   3840
cacacatgta agtgactgat ataaaagaga aaaaaggcga tttttccgcc taaaactctt   3900
taaaacttat taaaactctt aaaacccgcc tggcctgtgc ataactgtct ggccagcgca   3960
cagcccaaga gctgcaaaaa gcgcctaccc ttcggtcgct gcgctcccta cgccccgccg   4020
cttcgcgtcg gcctatcgcg gccgctggcc gctcaaaaat ggctggccta cggccaggca   4080
atctaccagg gcgcggacaa gccgcgccgt cgccactcga ccgccggcgc ccacatcaag   4140
```

-continued

```
gcaccctgcc tcgcgcgttt cggtgatgac ggtgaaaacc tctgacacat gcagctcccg   4200
gaaacggtca cagcttgtct gtaagcggat gccgggagca gacaagcccg tcagggcgcg   4260
tcagcgggtg ttggcgggtg tcggggcgca gccatgaccc agtcacgtag cgatagcgga   4320
gtgtatactg gcttaactat gcggcatcag agcagattgt actgagagtg caccatatgc   4380
ggtgtgaaat accgcacaga tgcgtaagga gaaaataccg catcaggccc tcttccgctt   4440
cctcgctcac tgactcgctg cgctcggtcg ttcggctgcg gcgagcggta tcagctcact   4500
caaaggcggt aatacggtta tccacagaat caggggataa cgcaggaaag aacatgtgag   4560
caaaaggcca gcaaaaggcc aggaaccgta aaaaggccgc gttgctggcg tttttccata   4620
ggctccgccc ccctgacgag catcacaaaa atcgacgctc aagtcagagg tggcgaaacc   4680
cgacaggact ataaagatac caggcgtttc cccctggaag ctccctcgtg cgctctcctg   4740
ttccgaccct gccgcttacc ggatacctgt ccgcctttct cccttcggga agcgtggcgc   4800
tttctcatag ctcacgctgt aggtatctca gttcggtgta ggtcgttcgc tccaagctgg   4860
gctgtgtgca cgaacccccc gttcagcccg accgctgcgc cttatccggt aactatcgtc   4920
ttgagtccaa cccggtaaga cacgacttat cgccactggc agcagccact ggtaacagga   4980
ttagcagagc gaggtatgta ggcggtgcta cagagttctt gaagtggtgg cctaactacg   5040
gctacactag aaggacagta tttggtatct gcgctctgct gaagccagtt accttcggaa   5100
aaagagttgg tagctcttga tccggcaaac aaaccaccgc tggtagcggt ggtttttttg   5160
tttgcaagca gcagattacg cgcagaaaaa aaggatctca agaagatcct ttgatctttt   5220
ctacggggtc tgacgctcag tggaacgaaa actcacgtta agggattttg gtcatgcatt   5280
ctaggtacta aaacaattca tccagtaaaa tataatattt tattttctcc caatcaggct   5340
tgatccccag taagtcaaaa aatagctcga catactgttc ttccccgata tcctccctga   5400
tcgaccggac gcagaaggca atgtcatacc acttgtccgc cctgccgctt ctcccaagat   5460
caataaagcc acttactttg ccatctttca caaagatgtt gctgtctccc aggtcgccgt   5520
gggaaaagac aagttcctct tcgggctttt ccgtctttaa aaaatcatac agctcgcgcg   5580
gatctttaaa tggagtgtct tcttcccagt tttcgcaatc cacatcggcc agatcgttat   5640
tcagtaagta atccaattcg gctaagcggc tgtctaagct attcgtatag ggacaatccg   5700
atatgtcgat ggagtgaaag agcctgatgc actccgcata cagctcgata atcttttcag   5760
ggctttgttc atcttcatac tcttccgagc aaaggacgcc atcggcctca ctcatgagca   5820
gattgctcca gccatcatgc cgttcaaagt gcaggacctt tggaacaggc agctttcctt   5880
ccagccatag catcatgtcc ttttcccgtt ccacatcata ggtggtccct ttataccggc   5940
tgtccgtcat ttttaaatat aggttttcat tttctcccac cagcttatat accttagcag   6000
gagacattcc ttccgtatct tttacgcagc ggtatttttc gatcagtttt ttcaattccg   6060
gtgatattct cattttagcc atttattatt tccttcctct tttctacagt atttaaagat   6120
accccaagaa gctaattata acaagacgaa ctccaattca ctgttccttg cattctaaaa   6180
ccttaaatac cagaaaacag ctttttcaaa gttgttttca aagttggcgt ataacatagt   6240
atcgacggag ccgattttga aaccgcggtg atcacaggca gcaacgctct gtcatcgtta   6300
caatcaacat gctaccctcc gcgagatcat ccgtgtttca aacccggcag cttagttgcc   6360
gttcttccga atagcatcgg taacatgagc aaagtctgcc gccttacaac ggctctcccg   6420
ctgacgccgt cccggactga tgggctgcct gtatcgagtg gtgattttgt gccgagctgc   6480
cggtcgggga gctgttggct ggctggtggc aggatatatt gtggtgtaaa caaattgacg   6540
```

-continued

```
cttagacaac ttaataacac attgcggacg tttttaatgt actgaattaa cgccgaatta   6600
attcggggga tctggatttt agtactggat tttggtttta ggaattagaa attttattga   6660
tagaagtatt ttacaaatac aaatacatac taagggtttc ttatatgctc aacacatgag   6720
cgaaacccta taggaaccct aattccctta tctgggaact actcacacat tattatggag   6780
aaactcgagc ttgtcgatcg actctagcta gaggatcgat ccgaacccca gagtcccgct   6840
cagaagaact cgtcaagaag gcgatagaag gcgatgcgct gcgaatcggg agcggcgata   6900
ccgtaaagca cgaggaagcg gtcagcccat tcgccgccaa gttcttcagc aatatcacgg   6960
gtagccaacg ctatgtcctg atagcggtcc gccacaccca gccggccaca gtcgatgaat   7020
ccagaaaagc ggccattttc caccatgata ttcggcaagc aggcatcgcc atgtgtcacg   7080
acgagatcct cgccgtcggg catgcgcgcc ttgagcctgg cgaacagttc ggctggcgcg   7140
agcccctgat gttcttcgtc cagatcatcc tgatcgacaa gaccggcttc catccgagta   7200
cgtgctcgct cgatgcgatg tttcgcttgg tggtcgaatg ggcaggtagc cggatcaagc   7260
gtatgcagcc gccgcattgc atcagccatg atggatactt tctcggcagg agcaaggtga   7320
gatgacagga gatcctgccc cggcacttcg cccaatagca gccagtccct tcccgcttca   7380
gtgacaacgt cgagcacagc tgcgcaagga acgcccgtcg tggccagcca cgatagccgc   7440
gctgcctcgt cctggagttc attcagggca ccggacaggt cggtcttgac aaaaagaacc   7500
gggcgcccct gcgctgacag ccgaaacacg gcggcatcag agcagccgat tgtctgttgt   7560
gcccagtcat agccgaatag cctctccacc caagcggccg gagaacctgc gtgcaatcca   7620
tcttgttcaa tccccatggt cgatcgacag atctgcgaaa gctcgagaga gatagatttg   7680
tagagagaga ctggtgattt cagcgtgtcc tctccaaatg aaatgaactt ccttatatag   7740
aggaagggtc ttgcgaagga tagtgggatt gtgcgtcatc ccttacgtca gtggagatat   7800
cacatcaatc cacttgcttt gaagacgtgg ttggaacgtc ttcttttttcc acgatgctcc   7860
tcgtgggtgg gggtccatct ttgggaccac tgtcggcaga ggcatcttga acgatagcct   7920
ttcctttatc gcaatgatgg catttgtagg tgccaccttc cttttctact gtccttttga   7980
tgaagtgaca gatagctggg caatggaatc cgaggaggtt tcccgatatt accctttgtt   8040
gaaaagtctc aatagccctt tggtcttctg agactgtatc tttgatattc ttggagtaga   8100
cgagagtgtc gtgctccacc atgttcacat caatccactt gctttgaaga cgtggttgga   8160
acgtcttctt tttccacgat gctcctcgtg ggtgggggtc catctttggg accactgtcg   8220
gcagaggcat cttgaacgat agcctttcct ttatcgcaat gatggcattt gtaggtgcca   8280
ccttcctttt ctactgtcct tttgatgaag tgacagatag ctgggcaatg gaatccgagg   8340
aggtttcccg atattaccct ttgttgaaaa gtctcaatag ccctttggtc ttctgagact   8400
gtatctttga tattcttgga gtagacgaga gtgtcgtgct ccaccatgtt ggcaagctgc   8460
tctagccaat acgcaaaccg cctctccccg cgcgttggcc gattcattaa tgcagctggc   8520
acgacaggtt tcccgactgg aaagcgggca gtgagcgcaa cgcaattaat gtgagttagc   8580
tcactcatta ggcaccccag gctttacact ttatgcttcc ggctcgtatg ttgtgtggaa   8640
ttgtgagcgg ataacaattt cacacaggaa acagctatga catgattacg aattcgagct   8700
cggtacccgg ggatcggcgc gccagatttg ccttttcaat ttcagaaaga atgctaaccc   8760
acagatggtt agagaggctt acgcagcagg tatcatcaag acgatctacc cgagcaataa   8820
tctccaggaa atcaaatacc ttcccaagaa ggttaaagat gcagtcaaaa gattcaggac   8880
taactgcatc aagaacacag agaaagatat atttctcaag atcagaagta ctattccagt   8940
```

-continued atggacgatt caaggcttgc ttcacaaacc aaggcaagta atagagattg gagtctctaa 9000
aaaggtagtt cccactgaat caaaggccat ggagtcaaag attcaaatag aggacctaac 9060
agaactcgcc gtaaagactg gcgaacagtt catacagagt ctcttacgac tcaatgacaa 9120
gaagaaaatc ttcgtcaaca tggtggagca cgacacactt gtctactcca aaaatatcaa 9180
agatacagtc tcagaagacc aaagggcaat tgagactttt caacaaaggg taatatccgg 9240
aaacctcctc ggattccatt gcccagctat ctgtcacttt attgtgaaga tagtggaaaa 9300
ggaaggtggc tcctacaaat gccatcattg cgataaagga aaggccatcg ttgaagatgc 9360
ctctgccgac agtggtccca aagatggacc cccacccacg aggagcatcg tggaaaaaga 9420
agacgttcca accacgtctt caaagcaagt ggattgatgt gatatctcca ctgacgtaag 9480
ggatgacgca caatcccact atccttcgca agacccttcc tctatataag gaagttcatt 9540
tcatttggag agaacacggg ggactcctgc aggaaaaatg gatcattatc ttgatattag 9600
acttagacct gatccagaat ttccaccagc tcaacttatg tctgttcttt ttggaaaact 9660
tcatcaagct cttgttgctc aaggaggaga tagaattgga gtttcttttc ctgatcttga 9720
tgaatcaaga tcaagacttg gagaaagact tagaattcat gcttctgctg atgatcttag 9780
agctttgctt gctagacctt ggcttgaagg acttagagat catcttcaat ttggagaacc 9840
agctgttgtt ccacatccaa ctccttatag acaagtttca agagttcaag ctaaatctaa 9900
tccagaaaga cttagaagaa gacttatgag aagacatgat ctttctgaag aagaagctag 9960
aaaaagaatt cctgatactg ttgctagagc tttggatttg ccttttgtta cacttagatc 10020
acaatctact ggacaacatt ttagactttt tattagacat ggaccacttc aagttactgc 10080
tgaagaagga ggatttactt gttatggact ttctaaggga ggttttgttc cttggtttgg 10140
atctggagct actaattttt ctcttcttaa gcaagctgga gatgttgaag aaaatcctgg 10200
acccatggat aagaagtact ctatcggact cgatatcgga actaactctg tgggatgggc 10260
tgtgatcacc gatgagtaca aggtgccatc taagaagttc aaggttctcg gaaacaccga 10320
taggcactct atcaagaaaa accttatcgg tgctctcctc ttcgattctg gtgaaactgc 10380
tgaggctacc agactcaaga gaaccgctag aagaaggtac accagaagaa agaacaggat 10440
ctgctacctc caagagatct tctctaacga gatggctaaa gtggatgatt cattcttcca 10500
caggctcgaa gagtcattcc tcgtggaaga agataagaag cacgagaggc accctatctt 10560
cggaaacatc gttgatgagg tggcatacca cgagaagtac cctactatct accacctcag 10620
aaagaagctc gttgattcta ctgataaggc tgatctcagg ctcatctacc tcgctctcgc 10680
tcacatgatc aagttcagag gacacttcct catcgagggt gatctcaacc ctgataactc 10740
tgatgtggat aagttgttca tccagctcgt gcagacctac aaccagcttt tcgaagagaa 10800
ccctatcaac gcttcaggtg tggatgctaa ggctatcctc tctgctaggc tctctaagtc 10860
aagaaggctt gagaacctca ttgctcagct ccctggtgag aagaagaacg gacttttcgg 10920
aaacttgatc gctctctctc tcggactcac ccctaacttc aagtctaact tcgatctcgc 10980
tgaggatgca aagctccagc tctcaaagga tacctacgat gatgatctcg ataacctcct 11040
cgctcagatc ggagatcagt acgctgattt gttcctcgct gctaagaacc tctctgatgc 11100
tatcctcctc agtgatatcc tcagagtgaa caccgagatc accaaggctc cactctcagc 11160
ttctatgatc aagagatacg atgagcacca ccaggatctc acacttctca aggctcttgt 11220
tagacagcag ctcccagaga agtacaaaga gattttcttc gatcagtcta agaacggata 11280
cgctggttac atcgatggtg gtgcatctca agaagagttc tacaagttca tcaagcctat 11340

-continued

```
cctcgagaag atggatggaa ccgaggaact cctcgtgaag ctcaatagag aggatcttct  11400
cagaaagcag aggaccttcg ataacggatc tatccctcat cagatccacc tcggagagtt  11460
gcacgctatc cttagaaggc aagaggattt ctacccattc ctcaaggata acagggaaaa  11520
gattgagaag attctcacct tcagaatccc ttactacgtg ggacctctcg ctagaggaaa  11580
ctcaagattc gcttggatga ccagaaagtc tgaggaaacc atcacccctt ggaacttcga  11640
agaggtggtg gataagggtg ctagtgctca gtctttcatc gagaggatga ccaacttcga  11700
taagaacctt ccaaacgaga aggtgctccc taagcactct ttgctctacg agtacttcac  11760
cgtgtacaac gagttgacca aggttaagta cgtgaccgag ggaatgagga agcctgcttt  11820
tttgtcaggt gagcaaaaga aggctatcgt tgatctcttg ttcaagacca acagaaaggt  11880
gaccgtgaag cagctcaaag aggattactt caagaaaatc gagtgcttcg attcagttga  11940
gatttctggt gttgaggata ggttcaacgc atctctcgga acctaccacg atctcctcaa  12000
gatcattaag gataaggatt tcttggataa cgaggaaaac gaggatatct tggaggatat  12060
cgttcttacc ctcaccctct ttgaagatag agagatgatt gaagaaaggc tcaagaccta  12120
cgctcatctc ttcgatgata aggtgatgaa gcagttgaag agaagaagat acactggttg  12180
gggaaggctc tcaagaaagc tcattaacgg aatcagggat aagcagtctg gaaagacaat  12240
ccttgatttc ctcaagtctg atggattcgc taacagaaac ttcatgcagc tcatccacga  12300
tgattctctc acctttaaag aggatatcca gaaggctcag gtttcaggac agggtgatag  12360
tctccatgag catatcgcta acctcgctgg atctcctgca atcaagaagg gaatcctcca  12420
gactgtgaag gttgtggatg agttggtgaa ggtgatggga aggcataagc ctgagaacat  12480
cgtgatcgaa atggctagag agaaccagac cactcagaag ggacagaaga actctaggga  12540
aaggatgaag aggatcgagg aaggtatcaa agagcttgga tctcagatcc tcaaagagca  12600
ccctgttgag aacactcagc tccagaatga gaagctctac ctctactacc tccagaacgg  12660
aagggatatg tatgtggatc aagagttgga tatcaacagg ctctctgatt acgatgttga  12720
tcatatcgtg ccacagtcat tcttgaagga tgattctatc gataacaagg tgctcaccag  12780
gtctgataag aacaggggta agagtgataa cgtgccaagt gaagaggttg tgaagaaaat  12840
gaagaactat tggaggcagc tcctcaacgc taagctcatc actcagagaa agttcgataa  12900
cttgactaag gctgagaggg gaggactctc tgaattggat aaggcaggat tcatcaagag  12960
gcagcttgtg gaaaccaggc agatcactaa gcacgttgca cagatcctcg attctaggat  13020
gaacaccaag tacgatgaga acgataagtt gatcagggaa gtgaaggtta tcaccctcaa  13080
gtcaaagctc gtgtctgatt tcagaaagga tttccaattc tacaaggtga gggaaatcaa  13140
caactaccac cacgctcacg atgcttacct taacgctgtt gttggaaccg ctctcatcaa  13200
gaagtatcct aagctcgagt cagagttcgt gtacggtgat tacaaggtgt acgatgtgag  13260
gaagatgatc gctaagtctg agcaagagat cggaaaggct accgctaagt atttcttcta  13320
ctctaacatc atgaatttct tcaagaccga gattaccctc gctaacggtg agatcagaaa  13380
gaggccactc atcgagacaa acggtgaaac aggtgagatc gtgtgggata agggaaggga  13440
tttcgctacc gttagaaagg tgctctctat gccacaggtg aacatcgtta agaaaaccga  13500
ggtgcagacc ggtggattct ctaaagagtc tatcctccct aagaggaact ctgataagct  13560
cattgctagg aagaaggatt gggaccctaa gaaatacggt ggtttcgatt ctcctaccgt  13620
ggcttactct gttctcgttg tggctaaggt tgagaaggga aagagtaaga agctcaagtc  13680
tgttaaggaa cttctcggaa tcactatcat ggaaaggtca tctttcgaga agaacccaat  13740
```

-continued cgatttcctc gaggctaagg gatacaaaga ggttaagaag gatctcatca tcaagctccc 13800
aaagtactca ctcttcgaac tcgagaacgg tagaaagagg atgctcgctt ctgctggtga 13860
gcttcaaaag ggaaacgagc ttgctctccc atctaagtac gttaactttc tttacctcgc 13920
ttctcactac gagaagttga agggatctcc agaagataac gagcagaagc aacttttcgt 13980
tgagcagcac aagcactact tggatgagat catcgagcag atctctgagt tctctaaaag 14040
ggtgatcctc gctgatgcaa acctcgataa ggtgttgtct gcttacaaca agcacagaga 14100
taagcctatc agggaacagg cagagaacat catccatctc ttcaccctta ccaacctcgg 14160
tgctcctgct gctttcaagt acttcgatac aaccatcgat aggaagagat acacctctac 14220
caaagaagtg ctcgatgcta ccctcatcca tcagtctatc actggactct acgagactag 14280
gatcgatctc tcacagctcg gtggtgattc aagggctgat cctaagaaga agaggaaggt 14340
ttgacgtcga cgatatgaag atgaagatga aatatttggt gtgtcaaata aaaagcttgt 14400
gtgcttaagt ttgtgttttt ttcttggctt gttgtgttat gaatttgtgg ctttttctaa 14460
tattaaatga atgtaagatc acattataat gaataaacaa atgtttctat aatccattgt 14520
gaatgttttg ttggatctct tctgcagcat ataactactg tatgtgctat ggtatggact 14580
atggaatatg attaaagata agccagagct ctggtgacgg acggcgcgct ggcagacata 14640
ctgtcccaca aatgaagatg gaatctgtaa aagaaaacgc gtgaaataat gcgtctgaca 14700
aaggttaggt cggctgcctt taatcaatac caaagtggtc cctaccacga tggaaaaact 14760
gtgcagtcgg tttggctttt tctgacgaac aaataagatt cgtggccgac aggtgggggt 14820
ccaccatgtg aaggcatctt cagactccaa taatggagca atgacgtaag ggcttacgaa 14880
ataagtaagg gtagtttggg aaatgtccac tcacccgtca gtctataaat acttagcccc 14940
tccctcattg ttaagggagc aaaatctcag agagatagtc ctagagagag aaagagagca 15000
agtagcctag aagtagtcaa ggcggcgaag tattcaggca cgtggccagg aagaagaaaa 15060
gccaagacga cgaaaacagg taagagctaa gcttcctgca ggttcactgc cgtataggca 15120
gcattaacat taccattaac ggttttagag ctagaaatag caagttaaaa taaggctagt 15180
ccgttatcaa cttgaaaaag tggcaccgag tcggtgcgtt cactgccgta taggcagagg 15240
gacaccaatg tcctgctgtt ttagagctag aaatagcaag ttaaaataag gctagtccgt 15300
tatcaacttg aaaaagtggc accgagtcgg tgcgttcact gccgtatagg caggtcgatc 15360
gacaagctcg agtttctcca ataatgtg tgagtagttc ccagataagg gaattagggt 15420
tcctataggg tttcgctcat gtgttgagca tataagaaac ccttagtatg tatttgtatt 15480
tgtaaaatac ttctatcaat aaaatttcta attcctaaaa ccaaaatcca gtactaaaat 15540
ccagatcccc cgaattagag ctctaccggc gagctttggg tacgtcacgt ggctcgagcg 15600
cgtagtcctc ggtaggcaag cttatttaat tcatacagaa gcaatctttg tttcagatgt 15660
tcactacaaa actcatcctc ttcttcaata tttttggttt cggaatgatc gctatcttaa 15720
ctcttttcct tacacatggc cgcaaacgcg ttgatgttct tggatggatt tgcatgatct 15780
ttgctttatg cgtgtttgtt gcccccatgg gtatcatggt gagaatgcga gtcgcaaatt 15840
tcaacacttg cttctttctg tctctgacag ttttttttt ttcccctata attatattga 15900
ttgatttttg ttttctctct tctttactct attttccaga gaaaagtgat aaaaacgaag 15960
agtgtcgagt tcatgccatt ttctttatca ttcttcctca ccttgactgc ggtgatgtgg 16020
ttcttctatg gttttctaaa gaaagacctt tatgttgccg taagttaact atcacgcatg 16080
catcattatc acgtacatct ttctttacat tccaccaact ttatctttcc cattaatcat 16140

-continued

```
caacccagca actatttctt attccctttt gattaacttc cacttacaat ttccttttc  16200
ttgtcatgaa cagattccaa acacattggg ctttcttttt gggattgtcc agatggtgct  16260
ttatttaatc tacagaaacc ccaagaaatt acctgtagag gatcctaaac ttcgcgaatt  16320
gtccgagcac atcgtcgacg ttgcaaagct gagtgcaacc ctctgttccg agataaccac  16380
agtagtggtt ccacagccca tagacaatgg aaatgatgtt gaaggtcaaa aaattaagga  16440
agaaaacgag caggacattg gtgtccctgc agacaaagtt aagactaatc tttttctctt  16500
tctcatcttt tcacttctcc aatcattatc ctcggccgaa ttcagtaaag gagaagaact  16560
tttcactgga gttgtcccaa ttcttgttga attagatggt gatgttaatg ggcacaaatt  16620
ttctgtcagt ggagagggtg aaggtgatgc aacatacgga aaacttaccc ttaaatttat  16680
ttgcactact ggaaaactac ctgttccatg gccaacactt gtcactactt tcacttatgg  16740
tgttcaatgc ttttcaagat acccagatca tatgaagcgg cacgacttct tcaagagcgc  16800
catgcctgag ggatacgtgc aggagaggac catctctttc aaggacgacg ggaactacaa  16860
gacacgtgct gaagtcaagt ttgagggaga caccctcgtc aacaggatcg agcttaaggg  16920
aatcgatttc aaggaggacg gaaacatcct cggccacaag ttggaataca actacaactc  16980
ccacaacgta tacatcacgg cagacaaaca aaagaatgga atcaaagcta acttcaaaat  17040
tagacacaac attgaagatg gaagcgttca actagcagac cattatcaac aaaatactcc  17100
aattggcgat ggccctgtcc ttttaccaga caaccattac ctgtccacac aatctgccct  17160
ttcgaaagat cccaacgaaa agagagacca catggtcctt cttgagtttg taacagctgc  17220
tgggattaca catggcatgg atgaactata caaacatgat gagctttgat aacattaaca  17280
ttaccattaa cgtgatcttg gttatgtttt ttctttttaa ttttgcatgt aatcgttcaa  17340
agtggtggtg ccatgtctac ttgtaaggct gcaatgcagc catgttgtct attatgtcaa  17400
atctagttcc atttaatgtc aatctttatt ctcaacctaa aagaagaata tcaatcttta  17460
tgtaatacgt tttttcgagt aaataaaatg tccagtgaat ttacagttaa tgttaaatca  17520
gcattatatt ttaggaaaat agtattcaac ttatagttta atggttgaaa ttaaatatta  17580
atttttattt tatgatgtaa taattttaaa tttaaattat agctcctggc aagagttatt  17640
aataaaataa tactgccaat atttttttct aaattttatt tgaatttgtt atttatttta  17700
tggaaaatat ttttaaaaaa taattttcat attttttat ataagaagag ctcaaaaaaa  17760
ttttaaatcc atgttatttt acactaaaaa acagaagttt aaatagggga gaaattttta  17820
cattcgccaa caaaactata taaatttttg ttttgaatta taaaataata attattttc  17880
ctaaaaagaa ttcttcatga ttgtgccaaa taagtctcaa tgcaatttta aaaaaaatcc  17940
agacaaaatt tgtcttattt ctcactgtgc tatttttcta ataagcattt tcattgtgca  18000
attaaatcta ttggactcta atcaataata aagaaaaggg ataccttttaa tcttttatcg  18060
aagatatcaa ctaattctag agcgcggtaa tatcgcagaa caaaagtacc tgatatcgag  18120
tgtacttcaa gtcacaccgg cg                                            18142
```

```
<210> SEQ ID NO 14
<211> LENGTH: 22468
<212> TYPE: DNA
<213> ORGANISM: Artificial Sequence
<220> FEATURE:
<223> OTHER INFORMATION: SYNTHESIZED

<400> SEQUENCE: 14

agtgtggcac tggccgtcgt tttacaacgt cgtgactggg aaaaccctgg cgttacccaa     60
```

-continued

```
cttaatcgcc ttgcagcaca tccccctttc gccagctggc gtaatagcga agaggcccgc    120
accgatcgcc cttcccaaca gttgcgcagc ctgaatggcg aatgctagag cagcttgagc    180
ttggatcaga ttgtcgtttc ccgccttcag tttaaactat cagtgtttga caggatatat    240
tggcgggtaa acctaagaga aaagagcgtt tattagaata atcggatatt taaaagggcg    300
tgaaaaggtt tatccgttcg tccatttgta tgtgcatgcc aaccacaggg ttcccctcgg    360
gatcaaagta ctttgatcca acccctccgc tgctatagtg cagtcggctt ctgacgttca    420
gtgcagccgt cttctgaaaa cgacatgtcg cacaagtcct aagttacgcg acaggctgcc    480
gccctgccct tttcctggcg ttttcttgtc gcgtgtttta gtcgcataaa gtagaatact    540
tgcgactaga accggagaca ttacgccatg aacaagagcg ccgccgctgg cctgctgggc    600
tatgcccgcg tcagcaccga cgaccaggac ttgaccaacc aacgggccga actgcacgcg    660
gccggctgca ccaagctgtt ttccgagaag atcaccggca ccaggcgcga ccgcccggag    720
ctggccagga tgcttgacca cctacgccct ggcgacgttg tgacagtgac caggctagac    780
cgcctggccc gcagcacccg cgacctactg gacattgccg agcgcatcca ggaggccggc    840
gcgggcctgc gtagcctggc agagccgtgg gccgacacca ccacgccggc cggccgcatg    900
gtgttgaccg tgttcgccgg cattgccgag ttcgagcgtt ccctaatcat cgaccgcacc    960
cggagcgggc gcgaggccgc caaggcccga ggcgtgaagt ttggcccccg ccctaccctc   1020
accccggcac agatcgcgca cgcccgcgag ctgatcgacc aggaaggccg caccgtgaaa   1080
gaggcggctg cactgcttgg cgtgcatcgc tcgaccctgt accgcgcact tgagcgcagc   1140
gaggaagtga cgcccaccga ggccaggcgg cgcggtgcct tccgtgagga cgcattgacc   1200
gaggccgacg ccctggcggc cgccgagaat gaacgccaag aggaacaagc atgaaaccgc   1260
accaggacgg ccaggacgaa ccgtttttca ttaccgaaga gatcgaggcg gagatgatcg   1320
cggccgggta cgtgttcgag ccgcccgcgc acggctcaac cgtgcggctg catgaaatcc   1380
tggccggttt gtctgatgcc aagctggcgg cctggccggc cagcttggcc gctgaagaaa   1440
ccgagcgccg ccgtctaaaa aggtgatgtg tatttgagta aaacagcttg cgtcatgcgg   1500
tcgctgcgta tatgatgcga tgagtaaata aacaaatacg caaggggaac gcatgaaggt   1560
tatcgctgta cttaaccaga aaggcgggtc aggcaagacg accatcgcaa cccatctagc   1620
ccgcgccctg caactcgccg gggccgatgt tctgttagtc gattccgatc cccagggcag   1680
tgcccgcgat tgggcggccg tgcgggaaga tcaaccgcta accgttgtcg gcatcgaccg   1740
cccgacgatt gaccgcgacg tgaaggccat cggccggcgc gacttcgtag tgatcgacgg   1800
agcgccccag gcggcggact tggctgtgtc cgcgatcaag gcagccgact tcgtgctgat   1860
tccggtgcag ccaagccctt acgacatatg ggccaccgcc gacctggtgg agctggttaa   1920
gcagcgcatt gaggtcacgg atggaaggct acaagcggcc tttgtcgtgt cgcgggcgat   1980
caaaggcacg cgcatcggcg gtgaggttgc cgaggcgctg gccgggtacg agctgcccat   2040
tcttgagtcc cgtatcacgc agcgcgtgag ctacccaggc actgccgccg ccggcacaac   2100
cgttcttgaa tcagaacccg agggcgacgc tgcccgcgag gtccaggcgc tggccgctga   2160
aattaaatca aaactcattt gagttaatga ggtaaagaga aaatgagcaa aagcacaaac   2220
acgctaagtg ccggccgtcc gagcgcacgc agcagcaagg ctgcaacgtt ggccagcctg   2280
gcagacacgc cagccatgaa gcgggtcaac tttcagttgc cggcggagga tcacaccaag   2340
ctgaagatgt acgcggtacg ccaaggcaag accattaccg agctgctatc tgaatacatc   2400
gcgcagctac cagagtaaat gagcaaatga ataaatgagt agatgaattt tagcggctaa   2460
```

-continued

```
aggaggcggc atggaaaatc aagaacaacc aggcaccgac gccgtggaat gccccatgtg   2520
tggaggaacg ggcggttggc caggcgtaag cggctgggtt gtctgccggc cctgcaatgg   2580
cactggaacc cccaagcccg aggaatcggc gtgacggtcg caaaccatcc ggcccggtac   2640
aaatcggcgc ggcgctgggt gatgacctgg tggagaagtt gaaggccgcg caggccgccc   2700
agcggcaacg catcgaggca gaagcacgcc ccggtgaatc gtggcaagcg gccgctgatc   2760
gaatccgcaa agaatcccgg caaccgccgg cagccggtgc gccgtcgatt aggaagccgc   2820
ccaagggcga cgagcaacca gattttttcg ttccgatgct ctatgacgtg ggcacccgcg   2880
atagtcgcag catcatggac gtggccgttt tccgtctgtc gaagcgtgac cgacgagctg   2940
gcgaggtgat ccgctacgag cttccagacg ggcacgtaga ggtttccgca gggccggccg   3000
gcatggccag tgtgtgggat tacgacctgg tactgatggc ggtttcccat ctaaccgaat   3060
ccatgaaccg ataccgggaa gggaagggag acaagcccgg ccgcgtgttc cgtccacacg   3120
ttgcggacgt actcaagttc tgccggcgag ccgatggcgg aaagcagaaa gacgacctgg   3180
tagaaacctg cattcggtta aacaccacgc acgttgccat gcagcgtacg aagaaggcca   3240
agaacggccg cctggtgacg gtatccgagg gtgaagcctt gattagccgc tacaagatcg   3300
taaagagcga aaccgggcgg ccggagtaca tcgagatcga gctagctgat tggatgtacc   3360
gcgagatcac agaaggcaag aacccggacg tgctgacggt tcaccccgat tactttttga   3420
tcgatcccgg catcggccgt tttctctacc gcctggcacg ccgcgccgca ggcaaggcag   3480
aagccagatg gttgttcaag acgatctacg aacgcagtgg cagcgccgga gagttcaaga   3540
agttctgttt caccgtgcgc aagctgatcg ggtcaaatga cctgccggag tacgatttga   3600
aggaggaggc ggggcaggct ggcccgatcc tagtcatgcg ctaccgcaac ctgatcgagg   3660
gcgaagcatc cgccggttcc taatgtacgg agcagatgct agggcaaatt gccctagcag   3720
gggaaaaagg tcgaaaaggc ctctttcctg tggatagcac gtacattggg aacccaaagc   3780
cgtacattgg gaaccggaac ccgtacattg ggaacccaaa gccgtacatt gggaaccggt   3840
cacacatgta agtgactgat ataaaagaga aaaaaggcga tttttccgcc taaaactctt   3900
taaaacttat taaaactctt aaaacccgcc tggcctgtgc ataactgtct ggccagcgca   3960
cagcccaaga gctgcaaaaa gcgcctaccc ttcggtcgct gcgctcccta cgccccgccg   4020
cttcgcgtcg gcctatcgcg gccgctggcc gctcaaaaat ggctggccta cggccaggca   4080
atctaccagg gcgcggacaa gccgcgccgt cgccactcga ccgccggcgc ccacatcaag   4140
gcaccctgcc tcgcgcgttt cggtgatgac ggtgaaaacc tctgacacat gcagctcccg   4200
gaaacggtca cagcttgtct gtaagcggat gccgggagca gacaagcccg tcagggcgcg   4260
tcagcgggtg ttggcgggtg tcggggcgca gccatgaccc agtcacgtag cgatagcgga   4320
gtgtatactg gcttaactat gcggcatcag agcagattgt actgagagtg caccatatgc   4380
ggtgtgaaat accgcacaga tgcgtaagga gaaaataccg catcaggccc tcttccgctt   4440
cctcgctcac tgactcgctg cgctcggtcg ttcggctgcg gcgagcggta tcagctcact   4500
caaaggcggt aatacggtta tccacagaat caggggataa cgcaggaaag aacatgtgag   4560
caaaaggcca gcaaaaggcc aggaaccgta aaaaggccgc gttgctggcg tttttccata   4620
ggctccgccc ccctgacgag catcacaaaa atcgacgctc aagtcagagg tggcgaaacc   4680
cgacaggact ataaagatac caggcgtttc cccctggaag ctccctcgtg cgctctcctg   4740
ttccgaccct gccgcttacc ggatacctgt ccgcctttct cccttcggga agcgtggcgc   4800
tttctcatag ctcacgctgt aggtatctca gttcggtgta ggtcgttcgc tccaagctgg   4860
```

-continued gctgtgtgca cgaacccccc gttcagcccg accgctgcgc cttatccggt aactatcgtc 4920
ttgagtccaa cccggtaaga cacgacttat cgccactggc agcagccact ggtaacagga 4980
ttagcagagc gaggtatgta ggcggtgcta cagagttctt gaagtggtgg cctaactacg 5040
gctacactag aaggacagta tttggtatct gcgctctgct gaagccagtt accttcggaa 5100
aaagagttgg tagctcttga tccggcaaac aaaccaccgc tggtagcggt ggtttttttg 5160
tttgcaagca gcagattacg cgcagaaaaa aaggatctca agaagatcct ttgatctttt 5220
ctacggggtc tgacgctcag tggaacgaaa actcacgtta agggattttg gtcatgcatt 5280
ctaggtacta aaacaattca tccagtaaaa tataatattt tattttctcc caatcaggct 5340
tgatccccag taagtcaaaa aatagctcga catactgttc ttccccgata tcctccctga 5400
tcgaccggac gcagaaggca atgtcatacc acttgtccgc cctgccgctt ctcccaagat 5460
caataaagcc acttactttg ccatctttca caaagatgtt gctgtctccc aggtcgccgt 5520
gggaaaagac aagttcctct tcgggctttt ccgtctttaa aaaatcatac agctcgcgcg 5580
gatctttaaa tggagtgtct tcttcccagt tttcgcaatc cacatcggcc agatcgttat 5640
tcagtaagta atccaattcg gctaagcggc tgtctaagct attcgtatag ggacaatccg 5700
atatgtcgat ggagtgaaag agcctgatgc actccgcata cagctcgata atcttttcag 5760
ggctttgttc atcttcatac tcttccgagc aaaggacgcc atcggcctca ctcatgagca 5820
gattgctcca gccatcatgc cgttcaaagt gcaggacctt tggaacaggc agctttcctt 5880
ccagccatag catcatgtcc ttttcccgtt ccacatcata ggtggtccct ttataccggc 5940
tgtccgtcat ttttaaatat aggttttcat tttctcccac cagcttatat accttagcag 6000
gagacattcc ttccgtatct tttacgcagc ggtatttttc gatcagtttt ttcaattccg 6060
gtgatattct cattttagcc atttattatt tccttcctct tttctacagt atttaaagat 6120
accccaagaa gctaattata acaagacgaa ctccaattca ctgttccttg cattctaaaa 6180
ccttaaatac cagaaaacag ctttttcaaa gttgttttca aagttggcgt ataacatagt 6240
atcgacggag ccgattttga aaccgcggtg atcacaggca gcaacgctct gtcatcgtta 6300
caatcaacat gctaccctcc gcgagatcat ccgtgtttca aacccggcag cttagttgcc 6360
gttcttccga atagcatcgg taacatgagc aaagtctgcc gccttacaac ggctctcccg 6420
ctgacgccgt cccggactga tgggctgcct gtatcgagtg gtgattttgt gccgagctgc 6480
cggtcgggga gctgttggct ggctggtggc aggatatatt gtggtgtaaa caaattgacg 6540
cttagacaac ttaataacac attgcggacg tttttaatgt actgaattaa cgccgaatta 6600
attcggggga tctggatttt agtactggat tttggtttta ggaattagaa attttattga 6660
tagaagtatt ttacaaatac aaatacatac taagggtttc ttatatgctc aacacatgag 6720
cgaaacccta taggaaccct aattccctta tctgggaact actcacacat tattatggag 6780
aaactcgagc ttgtcgatcg actctagcta gaggatcgat ccgaacccca gagtcccgct 6840
cagaagaact cgtcaagaag gcgatagaag gcgatgcgct gcgaatcggg agcggcgata 6900
ccgtaaagca cgaggaagcg gtcagcccat tcgccgccaa gttcttcagc aatatcacgg 6960
gtagccaacg ctatgtcctg atagcggtcc gccacaccca gccggccaca gtcgatgaat 7020
ccagaaaagc ggccattttc caccatgata ttcggcaagc aggcatcgcc atgtgtcacg 7080
acgagatcct cgccgtcggg catgcgcgcc ttgagcctgg cgaacagttc ggctggcgcg 7140
agcccctgat gttcttcgtc cagatcatcc tgatcgacaa gaccggcttc catccgagta 7200
cgtgctcgct cgatgcgatg tttcgcttgg tggtcgaatg ggcaggtagc cggatcaagc 7260

-continued

```
gtatgcagcc gccgcattgc atcagccatg atggatactt tctcggcagg agcaaggtga   7320
gatgacagga gatcctgccc cggcacttcg cccaatagca gccagtccct tcccgcttca   7380
gtgacaacgt cgagcacagc tgcgcaagga acgcccgtcg tggccagcca cgatagccgc   7440
gctgcctcgt cctggagttc attcagggca ccggacaggt cggtcttgac aaaaagaacc   7500
gggcgcccct gcgctgacag ccgaaacacg gcggcatcag agcagccgat tgtctgttgt   7560
gcccagtcat agccgaatag cctctccacc caagcggccg gagaacctgc gtgcaatcca   7620
tcttgttcaa tccccatggt cgatcgacag atctgcgaaa gctcgagaga gatagatttg   7680
tagagagaga ctggtgattt cagcgtgtcc tctccaaatg aaatgaactt ccttatatag   7740
aggaagggtc ttgcgaagga tagtgggatt gtgcgtcatc ccttacgtca gtggagatat   7800
cacatcaatc cacttgcttt gaagacgtgg ttggaacgtc ttctttttcc acgatgctcc   7860
tcgtgggtgg gggtccatct ttgggaccac tgtcggcaga ggcatcttga acgatagcct   7920
ttcctttatc gcaatgatgg catttgtagg tgccaccttc cttttctact gtccttttga   7980
tgaagtgaca gatagctggg caatggaatc cgaggaggtt tcccgatatt accctttgtt   8040
gaaaagtctc aatagccctt tggtcttctg agactgtatc tttgatattc ttggagtaga   8100
cgagagtgtc gtgctccacc atgttcacat caatccactt gctttgaaga cgtggttgga   8160
acgtcttctt tttccacgat gctcctcgtg ggtgggggtc catctttggg accactgtcg   8220
gcagaggcat cttgaacgat agcctttcct ttatcgcaat gatggcattt gtaggtgcca   8280
ccttcctttt ctactgtcct tttgatgaag tgacagatag ctgggcaatg gaatccgagg   8340
aggtttcccg atattaccct ttgttgaaaa gtctcaatag ccctttggtc ttctgagact   8400
gtatctttga tattcttgga gtagacgaga gtgtcgtgct ccaccatgtt ggcaagctgc   8460
tctagccaat acgcaaaccg cctctccccg cgcgttggcc gattcattaa tgcagctggc   8520
acgacaggtt tcccgactgg aaagcgggca gtgagcgcaa cgcaattaat gtgagttagc   8580
tcactcatta ggcaccccag gctttacact ttatgcttcc ggctcgtatg ttgtgtggaa   8640
ttgtgagcgg ataacaattt cacacaggaa acagctatga catgattacg aattcgagct   8700
cggtacccac cctacttaaa aaccctttcg attaaatcta ttattattat ttttcatatt   8760
gttataatta aacaacgtag ataaagttta ataaatttat tttattaatt aatttaatta   8820
tataaaaaaa gaaagaggta aaaatgaaaa aggcaaaaag gtagttttct tgaacccaaa   8880
atttgtagag catggtcctc ttttttgaaa aaaaattaag acaaaacttg agagatttta   8940
ctttaataaa tttagattgt aagattgaag aaggaatcat caaaggggga tttaatattt   9000
atattttatt tttttataaa aaatttattt atttatattt tataattaat ttgatttata   9060
ataaattgag gtctaggtaa gtatttcacc tgccgaatgt tggcatatgg gatcactatg   9120
acaaatcaca aagctgccaa atcaaatttg tctttgccta aaccgctcca tcctaatacc   9180
acatcaaatc ctgtcttcat tcattctgag ttaaagcctt ccacacacca taaatactcc   9240
atccatgtac tgcaaagctc ccaccatctt tatcttcacg aaaaaaaaat cccacttcct   9300
cgtactgaaa tccagaggtc accatggatc ccattcgtcc gcgcacgcca agtcctgccc   9360
acgaacttct ggccggaccc cagccggata gggttcagcc gcagccgact gcagatcgtg   9420
ggggggctcc gcctgccggc agccccctgg atggcttgcc cgctcgacgg acgatgtccc   9480
gaacccgtct cccgtctccc cctgcaccct tgcctgcgtt ctcagcgggc agtttcagcg   9540
atctgctccg tcagttcgat ccgtcgcttc ttgatacatc gctttttaat tcgatgtctg   9600
ccttcggcgc tcctcataca gaggctgcct caggagaggg ggatgaggtg caatcgggtc   9660
```

-continued

```
tgcgtgcagc cgatgacccg caagccaccg tgcaggtcgc tgtgacggcc gcgcgaccgc   9720
cgcgcgccaa gccggcgccg cgacggcgtg ctgcgcacac ctctgacgct tcgccggccg   9780
ggcaggtcga tctatgcacg ctcggctaca gccagcagca gcaagagaag atcaaactga   9840
aggctcgttc gacagtagca cagcaccacg aggcactgat cggccatggg tttacacgtg   9900
cgcacatcgt tgcgctcagc caacacccgg cagccttagg gaccgtcgct gtcaagtacc   9960
aggccatgat cgcggcgttg ccggaggcga cacacgaaga catcgttggc ggcggcaaac  10020
agtggtccgg cgcacgcgcc ctggaagcat tgctcacggt gtcgggagag ttgagaggtc  10080
caccgttaca gttggacaca ggtcaacttc tcaagattgc aaaacgtggc ggcgtgaccg  10140
cggtggaggc agtgcatgca tggcgcaatg cactgacggg cgctcccctg aacctgaccc  10200
cggaccaggt ggtggccatc gccagcaata ttggcggcaa gcaggcgctg gagacggtgc  10260
agcggctgtt gccggtgctg tgcgagcaac atggcctgac cctggaccag gtggtggcca  10320
tcgccagcaa tggcggcggc aagcaggcgc tggagacggt gcagcggctg ttgccggtgc  10380
tgtgcgagca acatggtctg accccggacc aggtggtggc tatcgccagc aatattggcg  10440
gcaagcaggc gctggagacg gtgcagcggc tgttgccggt gctgtgcgag caacatggtc  10500
tgaccccgga ccaggtggtg gccatcgcca gcaataacgg cggcaagcag gcgctggaga  10560
cggtgcagcg gctgttgccg gtgctgtgcg agcaacatgg cctgaccccg gaccaggtgg  10620
tggctatcgc cagcaatatt ggcggcaagc aggcgctgga gacggtgcag cggctgttgc  10680
cggtgctgcg ccaggcccat ggcctgaccc cggcgcaggt ggtggccatc gccagccacg  10740
atggcggcaa gcaggcgctg gagacggtgc agcagctgtt gccggtgctg tgcgagcaac  10800
atggcctgac cccggcgcag gtggtggcca tcgccagcaa tagcggcggc aagcaggcgc  10860
tggagacggt gcagcggctg ttgccggtgc tgcgccaggc ccatggcctg accccggacc  10920
aggtggtggc catcgccagc aatagcggcg gcaagccggc gctggagacg gtgcagcggc  10980
tgttgccggt gctgtgcgag caacatggtc tgaccccgga ccaggtggtg gccatcgcca  11040
gcaataacgg cggcaagccg gcgctggaga cggtgcagcg gctgttgccg gtgctgtgcg  11100
agcaacatgg cctgacccgg gcgcaggtgg tggccatcgc cagcaatggc ggcggcaagc  11160
aggcgctgga gacggtgcag cggctgttgc cggtgctgcg ccaggcccat ggcctgaccc  11220
cggcgcaggt ggtggccatc gccagccacg atggcggcaa gcaggcgctg gagacggtgc  11280
agcagctgtt gccggtgctg tgcgagcaac atggcctgac cccggcgcag gtggtggcca  11340
tcgccagcaa tagcggcggc aagcaggcgc tggagacggt gcagcggctg ttgccggtgc  11400
tgcgccaggc ccatggcctg accccggacc aggtggtggc catcgccagc cacgatggcg  11460
gcaagcaggc gctggagacg gtgcagcggc tgttgccggt gctgtgcgag caacatggtc  11520
tgaccccgga ccaggtggtg gccatcgcca gcaataacgg cggcaagcag gcgctggaga  11580
cggtgcagcg gctgttgccg gtgctgtgcg agcaacatgg cctgaccccg gaccaggtgg  11640
tggccatcgc cagccacgat ggcggcaagc aggcgctgga gacggtgcag cggctgttgc  11700
cggtgctgtg cgagcaacat ggcctgaccc cggaccaggt ggtggccatc gccagccacg  11760
atggcggcaa gcaggcgctg gagacggtgc agcggctgtt gccggtgctg cgccaggccc  11820
atggcctgac cccggcgcag gtggtggcca tcgccagcca cgatggcggc aagccggcgc  11880
tggagacggt gcagcggctg ttgccggtgc tgtgcgagca acatggcctg accccggacc  11940
aggtggtggc tatcgccagc aatattggcg gcaagcaggc gctggagacg gtgcagcggc  12000
tgttgccggt gctgtgcgag caacatggcc tgaccccgga ccaggtggtg gccatcgcca  12060
```

-continued

```
gcaatggcgg cggcaagcag gcgctggaga cggtgcagcg gctgttgccg gtgctgtgcg  12120
agcaacatgg tctgaccccg gcgcaggtgg tggccatcgc cagcaatggc ggcggcaggc  12180
cggcgctgga gagcattttt gcccagttat ctcgccctga tcaggcgttg gccgcgttga  12240
ccaacgacca cctcgtcgcc ttggcctgcc tcggcgggcg tcctgcgctg gaggcagtga  12300
aaaagggatt gccgcacgcg ccgaccttga tcaaaagaac caatcgccgt cttcccgaac  12360
gcacgtccca tcgcgttgcc gaccacgcgc aagtggctcg cgtgttgggt tttttccagt  12420
gccactccca cccagcgcaa gcatttgatg aagccatgac gcagttcggg atgagcaggc  12480
acgggttgtt acagctattt cgcagagccg gcgtcaccga actcgaggcc cacagtggaa  12540
cgctccccc agcctcgcag cgttggcacc gtatcctcca ggcatcaggg atgaaaaggg  12600
ccgaaccgtc cggtgcttcc gctcaaacgc cggaccaggc gtctttgcat gcattcgccg  12660
atgcgctgga gcgtgagctg gatgcgccca gcccaataga ccgggcgggc caggcgctgg  12720
caagcagcag ccgtaaacgg tcccgatcgg agagttctgt caccggctcc ttcgcacagc  12780
aagctgtcga ggtgcgcgtt cccgaacagc gcgatgcgct gcatttcctc cccctcagct  12840
ggggtgtaaa acgcccgcgt accaggatcg gggcggcct cccggatcct ggtacgccca  12900
tggacgccga cctggcaccg tccagcaccg tgatgtggga acaagatgct gaccccttcg  12960
caggggcagc ggatgatttt ccggcattca acgaagagga gatggcatgg ttgatggagc  13020
tatttcctca gtgaggggat cggcgcgcca gatttgcctt ttcaatttca gaaagaatgc  13080
taacccacag atggttagag aggcttacgc agcaggtatc atcaagacga tctacccgag  13140
caataatctc caggaaatca aataccttcc caagaaggtt aaagatgcag tcaaaagatt  13200
caggactaac tgcatcaaga acacagagaa agatatattt ctcaagatca gaagtactat  13260
tccagtatgg acgattcaag gcttgcttca caaaccaagg caagtaatag agattggagt  13320
ctctaaaaag gtagttccca ctgaatcaaa ggccatggag tcaaagattc aaatagagga  13380
cctaacagaa ctcgccgtaa agactggcga acagttcata cagagtctct tacgactcaa  13440
tgacaagaag aaaatcttcg tcaacatggt ggagcacgac acacttgtct actccaaaaa  13500
tatcaaagat acagtctcag aagaccaaag ggcaattgag acttttcaac aaagggtaat  13560
atccggaaac ctcctcggat tccattgccc agctatctgt cactttattg tgaagatagt  13620
ggaaaaggaa ggtggctcct acaaatgcca tcattgcgat aaaggaaagg ccatcgttga  13680
agatgcctct gccgacagtg gtcccaaaga tggaccccca cccacgagga gcatcgtgga  13740
aaaagaagac gttccaacca cgtcttcaaa gcaagtggat tgatgtgata tctccactga  13800
cgtaagggat gacgcacaat cccactatcc ttcgcaagac ccttcctcta tataaggaag  13860
ttcatttcat ttggagagaa cacgggggac tcctgcagga aaaatggatc attatcttga  13920
tattagactt agacctgatc cagaatttcc accagctcaa cttatgtctg ttctttttgg  13980
aaaacttcat caagctcttg ttgctcaagg aggagataga attggagttt cttttcctga  14040
tcttgatgaa tcaagatcaa gacttggaga aagacttaga attcatgctt ctgctgatga  14100
tcttagagct ttgcttgcta gaccttggct tgaaggactt agagatcatc ttcaatttgg  14160
agaaccagct gttgttccac atccaactcc ttatagacaa gtttcaagag ttcaagctaa  14220
atctaatcca gaaagactta gaagaagact tatgagaaga catgatcttt ctgaagaaga  14280
agctagaaaa agaattcctg atactgttgc tagagctttg gatttgcctt ttgttacact  14340
tagatcacaa tctactggac aacattttag actttttatt agacatggac cacttcaagt  14400
tactgctgaa gaaggaggat ttacttgtta tggactttct aagggaggtt ttgttccttg  14460
```

-continued

```
gtttggatct ggagctacta atttttctct tcttaagcaa gctggagatg ttgaagaaaa  14520
tcctggaccc atggataaga agtactctat cggactcgat atcggaacta actctgtggg  14580
atgggctgtg atcaccgatg agtacaaggt gccatctaag aagttcaagg ttctcggaaa  14640
caccgatagg cactctatca agaaaaacct tatcggtgct ctcctcttcg attctggtga  14700
aactgctgag gctaccagac tcaagagaac cgctagaaga aggtacacca gaagaaagaa  14760
caggatctgc tacctccaag agatcttctc taacgagatg gctaaagtgg atgattcatt  14820
cttccacagg ctcgaagagt cattcctcgt ggaagaagat aagaagcacg agaggcaccc  14880
tatcttcgga aacatcgttg atgaggtggc ataccacgag aagtacccta ctatctacca  14940
cctcagaaag aagctcgttg attctactga taaggctgat ctcaggctca tctacctcgc  15000
tctcgctcac atgatcaagt tcagaggaca cttcctcatc gagggtgatc tcaaccctga  15060
taactctgat gtggataagt tgttcatcca gctcgtgcag acctacaacc agcttttcga  15120
agagaaccct atcaacgctt caggtgtgga tgctaaggct atcctctctg ctaggctctc  15180
taagtcaaga aggcttgaga acctcattgc tcagctccct ggtgagaaga agaacggact  15240
tttcggaaac ttgatcgctc tctctctcgg actcacccct aacttcaagt ctaacttcga  15300
tctcgctgag gatgcaaagc tccagctctc aaaggatacc tacgatgatg atctcgataa  15360
cctcctcgct cagatcggag atcagtacgc tgatttgttc ctcgctgcta agaacctctc  15420
tgatgctatc ctcctcagtg atatcctcag agtgaacacc gagatcacca aggctccact  15480
ctcagcttct atgatcaaga gatacgatga gcaccaccag gatctcacac ttctcaaggc  15540
tcttgttaga cagcagctcc cagagaagta caaagagatt ttcttcgatc agtctaagaa  15600
cggatacgct ggttacatcg atggtggtgc atctcaagaa gagttctaca agttcatcaa  15660
gcctatcctc gagaagatgg atggaaccga ggaactcctc gtgaagctca atagagagga  15720
tcttctcaga aagcagagga ccttcgataa cggatctatc cctcatcaga tccacctcgg  15780
agagttgcac gctatcctta gaaggcaaga ggatttctac ccattcctca aggataacag  15840
ggaaaagatt gagaagattc tcaccttcag aatcccttac tacgtgggac ctctcgctag  15900
aggaaactca agattcgctt ggatgaccag aaagtctgag gaaaccatca ccccttggaa  15960
cttcgaagag gtggtggata agggtgctag tgctcagtct ttcatcgaga ggatgaccaa  16020
cttcgataag aaccttccaa acgagaaggt gctccctaag cactctttgc tctacgagta  16080
cttcaccgtg tacaacgagt tgaccaaggt taagtacgtg accgagggaa tgaggaagcc  16140
tgctttttg tcaggtgagc aaaagaaggc tatcgttgat ctcttgttca agaccaacag  16200
aaaggtgacc gtgaagcagc tcaaagagga ttacttcaag aaaatcgagt gcttcgattc  16260
agttgagatt tctggtgttg aggataggtt caacgcatct ctcggaacct accacgatct  16320
cctcaagatc attaaggata aggatttctt ggataacgag gaaaacgagg atatcttgga  16380
ggatatcgtt cttaccctca ccctctttga agatagagag atgattgaag aaaggctcaa  16440
gacctacgct catctcttcg atgataaggt gatgaagcag ttgaagagaa gaagatacac  16500
tggttgggga aggctctcaa gaaagctcat taacggaatc agggataagc agtctggaaa  16560
gacaatcctt gatttcctca agtctgatgg attcgctaac agaaacttca tgcagctcat  16620
ccacgatgat tctctcacct ttaaagagga tatccagaag gctcaggttt caggacaggg  16680
tgatagtctc catgagcata tcgctaacct cgctggatct cctgcaatca agaagggaat  16740
cctccagact gtgaaggttg tggatgagtt ggtgaaggtg atgggaaggc ataagcctga  16800
gaacatcgtg atcgaaatgg ctagagagaa ccagaccact cagaagggac agaagaactc  16860
```

tagggaaagg atgaagagga tcgaggaagg tatcaaagag cttggatctc agatcctcaa 16920
agagcaccct gttgagaaca ctcagctcca gaatgagaag ctctacctct actacctcca 16980
gaacggaagg gatatgtatg tggatcaaga gttggatatc aacaggctct ctgattacga 17040
tgttgatcat atcgtgccac agtcattctt gaaggatgat tctatcgata acaaggtgct 17100
caccaggtct gataagaaca ggggtaagag tgataacgtg ccaagtgaag aggttgtgaa 17160
gaaaatgaag aactattgga ggcagctcct caacgctaag ctcatcactc agagaaagtt 17220
cgataacttg actaaggctg agaggggagg actctctgaa ttggataagg caggattcat 17280
caagaggcag cttgtggaaa ccaggcagat cactaagcac gttgcacaga tcctcgattc 17340
taggatgaac accaagtacg atgagaacga taagttgatc agggaagtga aggttatcac 17400
cctcaagtca aagctcgtgt ctgatttcag aaaggatttc caattctaca aggtgaggga 17460
aatcaacaac taccaccacg ctcacgatgc ttaccttaac gctgttgttg gaaccgctct 17520
catcaagaag tatcctaagc tcgagtcaga gttcgtgtac ggtgattaca aggtgtacga 17580
tgtgaggaag atgatcgcta agtctgagca agagatcgga aaggctaccg ctaagtattt 17640
cttctactct aacatcatga atttcttcaa gaccgagatt accctcgcta acggtgagat 17700
cagaaagagg ccactcatcg agacaaacgg tgaaacaggt gagatcgtgt gggataaggg 17760
aagggatttc gctaccgtta gaaaggtgct ctctatgcca caggtgaaca tcgttaagaa 17820
aaccgaggtg cagaccggtg gattctctaa agagtctatc ctccctaaga ggaactctga 17880
taagctcatt gctaggaaga aggattggga ccctaagaaa tacggtggtt tcgattctcc 17940
taccgtggct tactctgttc tcgttgtggc taaggttgag aagggaaaga gtaagaagct 18000
caagtctgtt aaggaacttc tcggaatcac tatcatggaa aggtcatctt tcgagaagaa 18060
cccaatcgat ttcctcgagg ctaagggata caaagaggtt aagaaggatc tcatcatcaa 18120
gctcccaaag tactcactct tcgaactcga gaacggtaga aagaggatgc tcgcttctgc 18180
tggtgagctt caaaagggaa acgagcttgc tctcccatct aagtacgtta actttcttta 18240
cctcgcttct cactacgaga agttgaaggg atctccagaa gataacgagc agaagcaact 18300
tttcgttgag cagcacaagc actacttgga tgagatcatc gagcagatct ctgagttctc 18360
taaaagggtg atcctcgctg atgcaaacct cgataaggtg ttgtctgctt acaacaagca 18420
cagagataag cctatcaggg aacaggcaga gaacatcatc catctcttca cccttaccaa 18480
cctcggtgct cctgctgctt tcaagtactt cgatacaacc atcgatagga agagatacac 18540
ctctaccaaa gaagtgctcg atgctaccct catccatcag tctatcactg gactctacga 18600
gactaggatc gatctctcac agctcggtgg tgattcaagg gctgatccta agaagaagag 18660
gaaggtttga cgtcgacgat atgaagatga agatgaaata tttggtgtgt caaataaaaa 18720
gcttgtgtgc ttaagtttgt gtttttttct tggcttgttg tgttatgaat ttgtggcttt 18780
ttctaatatt aaatgaatgt aagatcacat tataatgaat aaacaaatgt ttctataatc 18840
cattgtgaat gttttgttgg atctcttctg cagcatataa ctactgtatg tgctatggta 18900
tggactatgg aatatgatta aagataagcc agagctctgg tgacggacgg cgcgctggca 18960
gacatactgt cccacaaatg aagatggaat ctgtaaaaga aaacgcgtga aataatgcgt 19020
ctgacaaagg ttaggtcggc tgcctttaat caataccaaa gtggtcccta ccacgatgga 19080
aaaactgtgc agtcggtttg gctttttctg acgaacaaat aagattcgtg gccgacaggt 19140
gggggtccac catgtgaagg catcttcaga ctccaataat ggagcaatga cgtaagggct 19200
tacgaaataa gtaagggtag tttgggaaat gtccactcac ccgtcagtct ataaatactt 19260

-continued agcccctccc tcattgttaa gggagcaaaa tctcagagag atagtcctag agagagaaag 19320
agagcaagta gcctagaagt agtcaaggcg gcgaagtatt caggcacgtg gccaggaaga 19380
agaaaagcca agacgacgaa aacaggtaag agctaagctt cctgcaggtt cactgccgta 19440
taggcagcat taacattacc attaacggtt ttagagctag aaatagcaag ttaaaataag 19500
gctagtccgt tatcaacttg aaaaagtggc accgagtcgg tgcgttcact gccgtatagg 19560
cagagggaca ccaatgtcct gctgttttag agctagaaat agcaagttaa aataaggcta 19620
gtccgttatc aacttgaaaa agtggcaccg agtcggtgcg ttcactgccg tataggcagg 19680
tcgatcgaca agctcgagtt tctccataat aatgtgtgag tagttcccag ataagggaat 19740
tagggttcct atagggtttc gctcatgtgt tgagcatata agaaaccctt agtatgtatt 19800
tgtatttgta aaatacttct atcaataaaa tttctaattc ctaaaaccaa aatccagtac 19860
taaaatccag atcccccgaa ttagagctct accggcgagc tttgggtacg tcacgtggct 19920
cgagcgcgta gtcctcggta ggcaagctta tttaattcat acagaagcaa tctttgtttc 19980
agatgttcac tacaaaactc atcctcttct tcaatatttt tggtttcgga atgatcgcta 20040
tcttaactct tttccttaca catggccgca aacgcgttga tgttcttgga tggatttgca 20100
tgatctttgc tttatgcgtg tttgttgccc ccatgggtat catggtgaga atgcgagtcg 20160
caaatttcaa cacttgcttc tttctgtctc tgacagtttt ttttttttcc cctataatta 20220
tattgattga tttttgtttt ctctcttctt tactctattt tccagagaaa agtgataaaa 20280
acgaagagtg tcgagttcat gccattttct ttatcattct tcctcacctt gactgcggtg 20340
atgtggttct tctatggttt tctaaagaaa gacctttatg ttgccgtaag ttaactatca 20400
cgcatgcatc attatcacgt acatctttct ttacattcca ccaactttat ctttcccatt 20460
aatcatcaac ccagcaacta tttcttattc ccttttgatt aacttccact tacaatttcc 20520
tttttcttgt catgaacaga ttccaaacac attgggcttt ctttttggga ttgtccagat 20580
ggtgctttat ttaatctaca gaaaccccaa gaaattacct gtagaggatc ctaaacttcg 20640
cgaattgtcc gagcacatcg tcgacgttgc aaagctgagt gcaaccctct gttccgagat 20700
aaccacagta gtggttccac agcccataga caatggaaat gatgttgaag gtcaaaaaat 20760
taaggaagaa aacgagcagg acattggtgt ccctgcagac aaagttaaga ctaatctttt 20820
tctctttctc atcttttcac ttctccaatc attatcctcg gccgaattca gtaaaggaga 20880
agaacttttc actggagttg tcccaattct tgttgaatta gatggtgatg ttaatgggca 20940
caaattttct gtcagtggag agggtgaagg tgatgcaaca tacggaaaac ttacccttaa 21000
atttatttgc actactggaa aactacctgt tccatggcca acacttgtca ctactttcac 21060
ttatggtgtt caatgctttt caagataccc agatcatatg aagcggcacg acttcttcaa 21120
gagcgccatg cctgagggat acgtgcagga gaggaccatc tctttcaagg acgacgggaa 21180
ctacaagaca cgtgctgaag tcaagtttga gggagacacc ctcgtcaaca ggatcgagct 21240
taagggaatc gatttcaagg aggacggaaa catcctcggc cacaagttgg aatacaacta 21300
caactcccac aacgtataca tcacggcaga caaacaaaag aatggaatca aagctaactt 21360
caaaattaga cacaacattg aagatggaag cgttcaacta gcagaccatt atcaacaaaa 21420
tactccaatt ggcgatggcc ctgtcctttt accagacaac cattacctgt ccacacaatc 21480
tgccctttcg aaagatccca acgaaaagag agaccacatg gtccttcttg agtttgtaac 21540
agctgctggg attacacatg gcatggatga actatacaaa catgatgagc tttgataaca 21600
ttaacattac cattaacgtg atcttggtta tgttttttct tttaatttt gcatgtaatc 21660 gttcaaagtg gtggtgccat gtctacttgt aaggctgcaa tgcagccatg ttgtctatta 21720
tgtcaaatct agttccattt aatgtcaatc tttattctca acctaaaaga agaatatcaa 21780
tctttatgta atacgttttt tcgagtaaat aaaatgtcca gtgaatttac agttaatgtt 21840
aaatcagcat tatattttag gaaaatagta ttcaacttat agtttaatgg ttgaaattaa 21900
atattaattt ttattttatg atgtaataat tttaaattta aattatagct cctggcaaga 21960
gttattaata aaataatact gccaatattt ttttctaaat tttatttgaa tttgttattt 22020
attttatgga aaatattttt aaaaaataat tttcatattt ttttatataa gaagagctca 22080
aaaaaatttt aaatccatgt tattttacac taaaaaacag aagtttaaat aggggagaaa 22140
tttttacatt cgccaacaaa actatataaa tttttgtttt gaattataaa ataataatta 22200
tttttcctaa aaagaattct tcatgattgt gccaaataag tctcaatgca attttaaaaa 22260
aaatccagac aaaatttgtc ttatttctca ctgtgctatt tttctaataa gcattttcat 22320
tgtgcaatta aatctattgg actctaatca ataataaaga aaagggatac ctttaatctt 22380
ttatcgaaga tatcaactaa ttctagagcg cggtaatatc gcagaacaaa agtacctgat 22440
atcgagtgta cttcaagtca caccggcg 22468

<210> SEQ ID NO 15
<211> LENGTH: 22694
<212> TYPE: DNA
<213> ORGANISM: Artificial Sequence
<220> FEATURE:
<223> OTHER INFORMATION: SYNTHESIZED

<400> SEQUENCE: 15
agtgtggcac tggccgtcgt tttacaacgt cgtgactggg aaaaccctgg cgttacccaa 60
cttaatcgcc ttgcagcaca tccccctttc gccagctggc gtaatagcga agaggcccgc 120
accgatcgcc cttcccaaca gttgcgcagc ctgaatggcg aatgctagag cagcttgagc 180
ttggatcaga ttgtcgtttc ccgccttcag tttaaactat cagtgtttga caggatatat 240
tggcgggtaa acctaagaga aaagagcgtt tattagaata atcggatatt taaaagggcg 300
tgaaaaggtt tatccgttcg tccatttgta tgtgcatgcc aaccacaggg ttcccctcgg 360
gatcaaagta ctttgatcca acccctccgc tgctatagtg cagtcggctt ctgacgttca 420
gtgcagccgt cttctgaaaa cgacatgtcg cacaagtcct aagttacgcg acaggctgcc 480
gccctgccct tttcctggcg ttttcttgtc gcgtgtttta gtcgcataaa gtagaatact 540
tgcgactaga accggagaca ttacgccatg aacaagagcg ccgccgctgg cctgctgggc 600
tatgcccgcg tcagcaccga cgaccaggac ttgaccaacc aacgggccga actgcacgcg 660
gccggctgca ccaagctgtt ttccgagaag atcaccggca ccaggcgcga ccgcccggag 720
ctggccagga tgcttgacca cctacgccct ggcgacgttg tgacagtgac caggctagac 780
cgcctggccc gcagcacccg cgacctactg gacattgccg agcgcatcca ggaggccggc 840
gcgggcctgc gtagcctggc agagccgtgg gccgacacca ccacgccggc cggccgcatg 900
gtgttgaccg tgttcgccgg cattgccgag ttcgagcgtt ccctaatcat cgaccgcacc 960
cggagcgggc gcgaggccgc caaggcccga ggcgtgaagt ttggcccccg ccctaccctc 1020
accccggcac agatcgcgca cgcccgcgag ctgatcgacc aggaaggccg caccgtgaaa 1080
gaggcggctg cactgcttgg cgtgcatcgc tcgaccctgt accgcgcact tgagcgcagc 1140
gaggaagtga cgcccaccga ggccaggcgg cgcggtgcct tccgtgagga cgcattgacc 1200
gaggccgacg ccctggcggc cgccgagaat gaacgccaag aggaacaagc atgaaaccgc 1260

-continued

```
accaggacgg ccaggacgaa ccgtttttca ttaccgaaga gatcgaggcg gagatgatcg   1320
cggccgggta cgtgttcgag ccgcccgcgc acggctcaac cgtgcggctg catgaaatcc   1380
tggccggttt gtctgatgcc aagctggcgg cctggccggc cagcttggcc gctgaagaaa   1440
ccgagcgccg ccgtctaaaa aggtgatgtg tatttgagta aaacagcttg cgtcatgcgg   1500
tcgctgcgta tatgatgcga tgagtaaata aacaaatacg caaggggaac gcatgaaggt   1560
tatcgctgta cttaaccaga aaggcgggtc aggcaagacg accatcgcaa cccatctagc   1620
ccgcgccctg caactcgccg gggccgatgt tctgttagtc gattccgatc cccagggcag   1680
tgcccgcgat tgggcggccg tgcgggaaga tcaaccgcta accgttgtcg gcatcgaccg   1740
cccgacgatt gaccgcgacg tgaaggccat cggccggcgc gacttcgtag tgatcgacgg   1800
agcgccccag gcggcggact tggctgtgtc cgcgatcaag gcagccgact tcgtgctgat   1860
tccggtgcag ccaagccctt acgacatatg ggccaccgcc gacctggtgg agctggttaa   1920
gcagcgcatt gaggtcacgg atggaaggct acaagcggcc tttgtcgtgt cgcgggcgat   1980
caaaggcacg cgcatcggcg gtgaggttgc cgaggcgctg gccgggtacg agctgcccat   2040
tcttgagtcc cgtatcacgc agcgcgtgag ctacccaggc actgccgccg ccggcacaac   2100
cgttcttgaa tcagaacccg agggcgacgc tgcccgcgag gtccaggcgc tggccgctga   2160
aattaaatca aaactcattt gagttaatga ggtaaagaga aaatgagcaa aagcacaaac   2220
acgctaagtg ccggccgtcc gagcgcacgc agcagcaagg ctgcaacgtt ggccagcctg   2280
gcagacacgc cagccatgaa gcgggtcaac tttcagttgc cggcggagga tcacaccaag   2340
ctgaagatgt acgcggtacg ccaaggcaag accattaccg agctgctatc tgaatacatc   2400
gcgcagctac cagagtaaat gagcaaatga ataaatgagt agatgaattt tagcggctaa   2460
aggaggcggc atggaaaatc aagaacaacc aggcaccgac gccgtggaat gccccatgtg   2520
tggaggaacg ggcggttggc caggcgtaag cggctgggtt gtctgccggc cctgcaatgg   2580
cactggaacc cccaagcccg aggaatcggc gtgacggtcg caaaccatcc ggcccggtac   2640
aaatcggcgc ggcgctgggt gatgacctgg tggagaagtt gaaggccgcg caggccgccc   2700
agcggcaacg catcgaggca gaagcacgcc ccggtgaatc gtggcaagcg gccgctgatc   2760
gaatccgcaa agaatcccgg caaccgccgg cagccggtgc gccgtcgatt aggaagccgc   2820
ccaagggcga cgagcaacca gatttttcg ttccgatgct ctatgacgtg ggcacccgcg   2880
atagtcgcag catcatggac gtggccgttt tccgtctgtc gaagcgtgac cgacgagctg   2940
gcgaggtgat ccgctacgag cttccagacg ggcacgtaga ggtttccgca gggccggccg   3000
gcatggccag tgtgtgggat tacgacctgg tactgatggc ggtttcccat ctaaccgaat   3060
ccatgaaccg ataccgggaa gggaagggag acaagcccgg ccgcgtgttc cgtccacacg   3120
ttgcggacgt actcaagttc tgccggcgag ccgatggcgg aaagcagaaa gacgacctgg   3180
tagaaacctg cattcggtta aacaccacgc acgttgccat gcagcgtacg aagaaggcca   3240
agaacggccg cctggtgacg gtatccgagg gtgaagcctt gattagccgc tacaagatcg   3300
taaagagcga aaccgggcgg ccggagtaca tcgagatcga gctagctgat tggatgtacc   3360
gcgagatcac agaaggcaag aacccggacg tgctgacggt tcaccccgat tactttttga   3420
tcgatcccgg catcggccgt tttctctacc gcctggcacg ccgcgccgca ggcaaggcag   3480
aagccagatg gttgttcaag acgatctacg aacgcagtgg cagcgccgga gagttcaaga   3540
agttctgttt caccgtgcgc aagctgatcg ggtcaaatga cctgccggag tacgatttga   3600
aggaggaggc ggggcaggct ggcccgatcc tagtcatgcg ctaccgcaac ctgatcgagg   3660
```

-continued gcgaagcatc cgccggttcc taatgtacgg agcagatgct agggcaaatt gccctagcag 3720
gggaaaaagg tcgaaaaggc ctctttcctg tggatagcac gtacattggg aacccaaagc 3780
cgtacattgg gaaccggaac ccgtacattg ggaacccaaa gccgtacatt gggaaccggt 3840
cacacatgta agtgactgat ataaaagaga aaaaaggcga tttttccgcc taaaactctt 3900
taaaacttat taaaactctt aaaacccgcc tggcctgtgc ataactgtct ggccagcgca 3960
cagcccaaga gctgcaaaaa gcgcctaccc ttcggtcgct gcgctcccta cgccccgccg 4020
cttcgcgtcg gcctatcgcg gccgctggcc gctcaaaaat ggctggccta cggccaggca 4080
atctaccagg gcgcggacaa gccgcgccgt cgccactcga ccgccggcgc ccacatcaag 4140
gcaccctgcc tcgcgcgttt cggtgatgac ggtgaaaacc tctgacacat gcagctcccg 4200
gaaacggtca cagcttgtct gtaagcggat gccgggagca gacaagcccg tcagggcgcg 4260
tcagcgggtg ttggcgggtg tcggggcgca gccatgaccc agtcacgtag cgatagcgga 4320
gtgtatactg gcttaactat gcggcatcag agcagattgt actgagagtg caccatatgc 4380
ggtgtgaaat accgcacaga tgcgtaagga gaaaataccg catcaggccc tcttccgctt 4440
cctcgctcac tgactcgctg cgctcggtcg ttcggctgcg gcgagcggta tcagctcact 4500
caaaggcggt aatacggtta tccacagaat caggggataa cgcaggaaag aacatgtgag 4560
caaaaggcca gcaaaaggcc aggaaccgta aaaaggccgc gttgctggcg tttttccata 4620
ggctccgccc ccctgacgag catcacaaaa atcgacgctc aagtcagagg tggcgaaacc 4680
cgacaggact ataaagatac caggcgtttc cccctggaag ctccctcgtg cgctctcctg 4740
ttccgaccct gccgcttacc ggatacctgt ccgcctttct cccttcggga agcgtggcgc 4800
tttctcatag ctcacgctgt aggtatctca gttcggtgta ggtcgttcgc tccaagctgg 4860
gctgtgtgca cgaacccccc gttcagcccg accgctgcgc cttatccggt aactatcgtc 4920
ttgagtccaa cccggtaaga cacgacttat cgccactggc agcagccact ggtaacagga 4980
ttagcagagc gaggtatgta ggcggtgcta cagagttctt gaagtggtgg cctaactacg 5040
gctacactag aaggacagta tttggtatct gcgctctgct gaagccagtt accttcggaa 5100
aaagagttgg tagctcttga tccggcaaac aaaccaccgc tggtagcggt ggtttttttg 5160
tttgcaagca gcagattacg cgcagaaaaa aaggatctca agaagatcct ttgatctttt 5220
ctacggggtc tgacgctcag tggaacgaaa actcacgtta agggattttg gtcatgcatt 5280
ctaggtacta aaacaattca tccagtaaaa tataatattt tattttctcc caatcaggct 5340
tgatccccag taagtcaaaa aatagctcga catactgttc ttccccgata tcctccctga 5400
tcgaccggac gcagaaggca atgtcatacc acttgtccgc cctgccgctt ctcccaagat 5460
caataaagcc acttactttg ccatctttca caaagatgtt gctgtctccc aggtcgccgt 5520
gggaaaagac aagttcctct tcgggctttt ccgtctttaa aaaatcatac agctcgcgcg 5580
gatctttaaa tggagtgtct tcttcccagt tttcgcaatc cacatcggcc agatcgttat 5640
tcagtaagta atccaattcg gctaagcggc tgtctaagct attcgtatag ggacaatccg 5700
atatgtcgat ggagtgaaag agcctgatgc actccgcata cagctcgata atcttttcag 5760
ggctttgttc atcttcatac tcttccgagc aaaggacgcc atcggcctca ctcatgagca 5820
gattgctcca gccatcatgc cgttcaaagt gcaggacctt tggaacaggc agctttcctt 5880
ccagccatag catcatgtcc ttttcccgtt ccacatcata ggtggtccct ttataccggc 5940
tgtccgtcat ttttaaatat aggttttcat tttctcccac cagcttatat accttagcag 6000
gagacattcc ttccgtatct tttacgcagc ggtatttttc gatcagtttt ttcaattccg 6060
gtgatattct cattttagcc atttattatt tccttcctct tttctacagt atttaaagat 6120
accccaagaa gctaattata acaagacgaa ctccaattca ctgttccttg cattctaaaa 6180
ccttaaatac cagaaaacag ctttttcaaa gttgttttca aagttggcgt ataacatagt 6240
atcgacggag ccgattttga aaccgcggtg atcacaggca gcaacgctct gtcatcgtta 6300
caatcaacat gctaccctcc gcgagatcat ccgtgtttca aacccggcag cttagttgcc 6360
gttcttccga atagcatcgg taacatgagc aaagtctgcc gccttacaac ggctctcccg 6420
ctgacgccgt cccggactga tgggctgcct gtatcgagtg gtgattttgt gccgagctgc 6480
cggtcgggga gctgttggct ggctggtggc aggatatatt gtggtgtaaa caaattgacg 6540
cttagacaac ttaataacac attgcggacg tttttaatgt actgaattaa cgccgaatta 6600
attcgggga tctggatttt agtactggat tttggtttta ggaattagaa attttattga 6660
tagaagtatt ttacaaatac aaatacatac taagggtttc ttatatgctc aacacatgag 6720
cgaaacccta taggaaccct aattccctta tctgggaact actcacacat tattatggag 6780
aaactcgagc ttgtcgatcg actctagcta gaggatcgat ccgaacccca gagtcccgct 6840
cagaagaact cgtcaagaag gcgatagaag gcgatgcgct gcgaatcggg agcggcgata 6900
ccgtaaagca cgaggaagcg gtcagcccat tcgccgccaa gttcttcagc aatatcacgg 6960
gtagccaacg ctatgtcctg atagcggtcc gccacaccca gccggccaca gtcgatgaat 7020
ccagaaaagc ggccattttc caccatgata ttcggcaagc aggcatcgcc atgtgtcacg 7080
acgagatcct cgccgtcggg catgcgcgcc ttgagcctgg cgaacagttc ggctggcgcg 7140
agcccctgat gttcttcgtc cagatcatcc tgatcgacaa gaccggcttc catccgagta 7200
cgtgctcgct cgatgcgatg tttcgcttgg tggtcgaatg ggcaggtagc cggatcaagc 7260
gtatgcagcc gccgcattgc atcagccatg atggatactt tctcggcagg agcaaggtga 7320
gatgacagga gatcctgccc cggcacttcg cccaatagca gccagtccct tcccgcttca 7380
gtgacaacgt cgagcacagc tgcgcaagga acgcccgtcg tggccagcca cgatagccgc 7440
gctgcctcgt cctggagttc attcagggca ccggacaggt cggtcttgac aaaaagaacc 7500
gggcgcccct gcgctgacag ccgaaacacg gcggcatcag agcagccgat tgtctgttgt 7560
gcccagtcat agccgaatag cctctccacc caagcggccg gagaacctgc gtgcaatcca 7620
tcttgttcaa tccccatggt cgatcgacag atctgcgaaa gctcgagaga gatagatttg 7680
tagagagaga ctggtgattt cagcgtgtcc tctccaaatg aaatgaactt ccttatatag 7740
aggaagggtc ttgcgaagga tagtgggatt gtgcgtcatc ccttacgtca gtggagatat 7800
cacatcaatc cacttgcttt gaagacgtgg ttggaacgtc ttcttttttcc acgatgctcc 7860
tcgtgggtgg gggtccatct ttgggaccac tgtcggcaga ggcatcttga acgatagcct 7920
ttcctttatc gcaatgatgg catttgtagg tgccaccttc cttttctact gtccttttga 7980
tgaagtgaca gatagctggg caatggaatc cgaggaggtt tcccgatatt accctttgtt 8040
gaaaagtctc aatagccctt tggtcttctg agactgtatc tttgatattc ttggagtaga 8100
cgagagtgtc gtgctccacc atgttcacat caatccactt gctttgaaga cgtggttgga 8160
acgtcttctt tttccacgat gctcctcgtg ggtgggggtc catctttggg accactgtcg 8220
gcagaggcat cttgaacgat agcctttcct ttatcgcaat gatggcattt gtaggtgcca 8280
ccttcctttt ctactgtcct tttgatgaag tgacagatag ctgggcaatg gaatccgagg 8340
aggtttcccg atattaccct ttgttgaaaa gtctcaatag ccctttggtc ttctgagact 8400
gtatctttga tattcttgga gtagacgaga gtgtcgtgct ccaccatgtt ggcaagctgc 8460

-continued

```
tctagccaat acgcaaaccg cctctccccg cgcgttggcc gattcattaa tgcagctggc   8520
acgacaggtt tcccgactgg aaagcgggca gtgagcgcaa cgcaattaat gtgagttagc   8580
tcactcatta ggcaccccag gctttacact ttatgcttcc ggctcgtatg ttgtgtggaa   8640
ttgtgagcgg ataacaattt cacacaggaa acagctatga catgattacg aattcgagct   8700
cggtacccag atttgccttt tcaatttcag aaagaatgct aacccacaga tggttagaga   8760
ggcttacgca gcaggtatca tcaagacgat ctacccgagc aataatctcc aggaaatcaa   8820
ataccttccc aagaaggtta aagatgcagt caaaagattc aggactaact gcatcaagaa   8880
cacagagaaa gatatatttc tcaagatcag aagtactatt ccagtatgga cgattcaagg   8940
cttgcttcac aaaccaaggc aagtaataga gattggagtc tctaaaaagg tagttcccac   9000
tgaatcaaag gccatggagt caaagattca aatagaggac ctaacagaac tcgccgtaaa   9060
gactggcgaa cagttcatac agagtctctt acgactcaat gacaagaaga aaatcttcgt   9120
caacatggtg gagcacgaca cacttgtcta ctccaaaaat atcaaagata cagtctcaga   9180
agaccaaagg gcaattgaga cttttcaaca aagggtaata tccggaaacc tcctcggatt   9240
ccattgccca gctatctgtc actttattgt gaagatagtg gaaaaggaag gtggctccta   9300
caaatgccat cattgcgata aaggaaaggc catcgttgaa gatgcctctg ccgacagtgg   9360
tcccaaagat ggacccccac ccacgaggag catcgtggaa aaagaagacg ttccaaccac   9420
gtcttcaaag caagtggatt gatgtgatat ctccactgac gtaagggatg acgcacaatc   9480
ccactatcct tcgcaagacc cttcctctat ataaggaagt tcatttcatt tggagagaac   9540
acgggggact atggatccca ttcgtccgcg cacgccaagt cctgcccacg aacttctggc   9600
cggaccccag ccggataggg ttcagccgca gccgactgca gatcgtgggg gggctccgcc   9660
tgccggcagc cccctggatg gcttgcccgc tcgacggacg atgtcccgaa cccgtctccc   9720
gtctccccct gcacccttgc ctgcgttctc agcgggcagt ttcagcgatc tgctccgtca   9780
gttcgatccg tcgcttcttg atacatcgct ttttaattcg atgtctgcct tcggcgctcc   9840
tcatacagag gctgcctcag gagaggggga tgaggtgcaa tcgggtctgc gtgcagccga   9900
tgacccgcaa gccaccgtgc aggtcgctgt gacggccgcg cgaccgccgc gcgccaagcc   9960
ggcgccgcga cggcgtgctg cgcacacctc tgacgcttcg ccggccgggc aggtcgatct  10020
atgcacgctc ggctacagcc agcagcagca agagaagatc aaactgaagg ctcgttcgac  10080
agtagcacag caccacgagg cactgatcgg ccatgggttt acacgtgcgc acatcgttgc  10140
gctcagccaa cacccggcag ccttagggac cgtcgctgtc aagtaccagg ccatgatcgc  10200
ggcgttgccg gaggcgacac acgaagacat cgttggcggc ggcaaacagt ggtccggcgc  10260
acgcgccctg gaagcattgc tcacggtgtc gggagagttg agaggtccac cgttacagtt  10320
ggacacaggt caacttctca agattgcaaa acgtggcggc gtgaccgcgg tggaggcagt  10380
gcatgcatgg cgcaatgcac tgacgggcgc tcccctgaac ctgaccccgg accaggtggt  10440
ggccatcgcc agcaatattg gcggcaagca ggcgctggag acggtgcagc ggctgttgcc  10500
ggtgctgtgc gagcaacatg gcctgaccct ggaccaggtg gtggccatcg ccagcaatgg  10560
cggcggcaag caggcgctgg agacggtgca gcggctgttg ccggtgctgt gcgagcaaca  10620
tggtctgacc ccggaccagg tggtggctat cgccagcaat attggcggca agcaggcgct  10680
ggagacggtg cagcggctgt tgccggtgct gtgcgagcaa catggtctga ccccggacca  10740
ggtggtggcc atcgccagca ataacggcgg caagcaggcg ctggagacgg tgcagcggct  10800
gttgccggtg ctgtgcgagc aacatggcct gaccccggac caggtggtgg ctatcgccag  10860
```

-continued caatattggc ggcaagcagg cgctggagac ggtgcagcgg ctgttgccgg tgctgcgcca 10920
ggcccatggc ctgaccccgg cgcaggtggt ggccatcgcc agccacgatg gcggcaagca 10980
ggcgctggag acggtgcagc agctgttgcc ggtgctgtgc gagcaacatg gcctgacccc 11040
ggcgcaggtg gtggccatcg ccagcaatag cggcggcaag caggcgctgg agacggtgca 11100
gcggctgttg ccggtgctgc gccaggccca tggcctgacc ccggaccagg tggtggccat 11160
cgccagcaat agcggcggca agccggcgct ggagacggtg cagcggctgt tgccggtgct 11220
gtgcgagcaa catggtctga ccccggacca ggtggtggcc atcgccagca ataacggcgg 11280
caagccggcg ctggagacgg tgcagcggct gttgccggtg ctgtgcgagc aacatggcct 11340
gacccgggcg caggtggtgg ccatcgccag caatggcggc ggcaagcagg cgctggagac 11400
ggtgcagcgg ctgttgccgg tgctgcgcca ggcccatggc ctgaccccgg cgcaggtggt 11460
ggccatcgcc agccacgatg gcggcaagca ggcgctggag acggtgcagc agctgttgcc 11520
ggtgctgtgc gagcaacatg gcctgacccc ggcgcaggtg gtggccatcg ccagcaatag 11580
cggcggcaag caggcgctgg agacggtgca gcggctgttg ccggtgctgc gccaggccca 11640
tggcctgacc ccggaccagg tggtggccat cgccagccac gatggcggca agcaggcgct 11700
ggagacggtg cagcggctgt tgccggtgct gtgcgagcaa catggtctga ccccggacca 11760
ggtggtggcc atcgccagca ataacggcgg caagcaggcg ctggagacgg tgcagcggct 11820
gttgccggtg ctgtgcgagc aacatggcct gaccccggac caggtggtgg ccatcgccag 11880
ccacgatggc ggcaagcagg cgctggagac ggtgcagcgg ctgttgccgg tgctgtgcga 11940
gcaacatggc ctgaccccgg accaggtggt ggccatcgcc agccacgatg gcggcaagca 12000
ggcgctggag acggtgcagc ggctgttgcc ggtgctgcgc caggcccatg gcctgacccc 12060
ggcgcaggtg gtggccatcg ccagccacga tggcggcaag ccggcgctgg agacggtgca 12120
gcggctgttg ccggtgctgt gcgagcaaca tggcctgacc ccggaccagg tggtggctat 12180
cgccagcaat attggcggca agcaggcgct ggagacggtg cagcggctgt tgccggtgct 12240
gtgcgagcaa catggcctga ccccggacca ggtggtggcc atcgccagca atggcggcgg 12300
caagcaggcg ctggagacgg tgcagcggct gttgccggtg ctgtgcgagc aacatggtct 12360
gaccccggcg caggtggtgg ccatcgccag caatggcggc ggcaggccgg cgctggagag 12420
catttttgcc cagttatctc gccctgatca ggcgttggcc gcgttgacca acgaccacct 12480
cgtcgccttg gcctgcctcg gcgggcgtcc tgcgctggag gcagtgaaaa agggattgcc 12540
gcacgcgccg accttgatca aaagaaccaa tcgccgtctt cccgaacgca cgtcccatcg 12600
cgttgccgac cacgcgcaag tggctcgcgt gttgggtttt ttccagtgcc actcccaccc 12660
agcgcaagca tttgatgaag ccatgacgca gttcgggatg agcaggcacg ggttgttaca 12720
gctatttcgc agagccggcg tcaccgaact cgaggcccac agtggaacgc tcccccccagc 12780 ctcgcagcgt tggcaccgta tcctccaggc atcagggatg aaaagggccg aaccgtccgg 12840
tgcttccgct caaacgccgg accaggcgtc tttgcatgca ttcgccgatg cgctggagcg 12900
tgagctggat gcgcccagcc caatagaccg ggcgggccag gcgctggcaa gcagcagccg 12960
taaacggtcc cgatcggaga gttctgtcac cggctccttc gcacagcaag ctgtcgaggt 13020
gcgcgttccc gaacagcgcg atgcgctgca tttcctcccc ctcagctggg gtgtaaaacg 13080
cccgcgtacc aggatcgggg gcggcctccc ggatcctggt acgcccatgg acgccgacct 13140
ggcaccgtcc agcaccgtga tgtgggaaca agatgctgac cccttcgcag gggcagcgga 13200
tgattttccg gcattcaacg aagaggagat ggcatggttg atggagctat ttcctcagtg 13260

-continued

```
aggggatcgg cgcgccagat ttgccttttc aatttcagaa agaatgctaa cccacagatg  13320
gttagagagg cttacgcagc aggtatcatc aagacgatct acccgagcaa taatctccag  13380
gaaatcaaat acttcccaag aaggttaaag atgcagtcaa aagattcagg actaactgca  13440
tcaagaacac agagaaagat atatttctca agatcagaag tactattcca gtatggacga  13500
ttcaaggctt gcttcacaaa ccaaggcaag taatagagat tggagtctct aaaaaggtag  13560
ttcccactga atcaaaggcc atggagtcaa agattcaaat agaggaccta acagaactcg  13620
ccgtaaagac tggcgaacag ttcatacaga gtctcttacg actcaatgac aagaagaaaa  13680
tcttcgtcaa catggtggag cacgacacac ttgtctactc caaaaatatc aaagatacag  13740
tctcagaaga ccaaagggca attgagactt ttcaacaaag ggtaatatcc ggaaacctcc  13800
tcggattcca ttgcccagct atctgtcact ttattgtgaa gatagtggaa aaggaaggtg  13860
gctcctacaa atgccatcat tgcgataaag gaaaggccat cgttgaagat gcctctgccg  13920
acagtggtcc caaagatgga cccccaccca cgaggagcat cgtggaaaaa gaagacgttc  13980
caaccacgtc ttcaaagcaa gtggattgat gtgatatctc cactgacgta agggatgacg  14040
cacaatccca ctatccttcg caagaccctt cctctatata aggaagttca tttcatttgg  14100
agagaacacg ggggactcct gcaggaaaaa tggatcatta tcttgatatt agacttagac  14160
ctgatccaga atttccacca gctcaactta tgtctgttct tttggaaaa cttcatcaag  14220
ctcttgttgc tcaaggagga gatagaattg gagtttcttt tcctgatctt gatgaatcaa  14280
gatcaagact tggagaaaga cttagaattc atgcttctgc tgatgatctt agagctttgc  14340
ttgctagacc ttggcttgaa ggacttagag atcatcttca atttggagaa ccagctgttg  14400
ttccacatcc aactccttat agacaagttt caagagttca agctaaatct aatccagaaa  14460
gacttagaag aagacttatg agaagacatg atctttctga agaagaagct agaaaaagaa  14520
ttcctgatac tgttgctaga gctttggatt tgccttttgt tacacttaga tcacaatcta  14580
ctggacaaca ttttagactt tttattagac atggaccact tcaagttact gctgaagaag  14640
gaggatttac ttgttatgga ctttctaagg gaggttttgt tccttggttt ggatctggag  14700
ctactaattt ttctcttctt aagcaagctg gagatgttga agaaaatcct ggacccatgg  14760
ataagaagta ctctatcgga ctcgatatcg gaactaactc tgtgggatgg gctgtgatca  14820
ccgatgagta caaggtgcca tctaagaagt tcaaggttct cggaaacacc gataggcact  14880
ctatcaagaa aaaccttatc ggtgctctcc tcttcgattc tggtgaaact gctgaggcta  14940
ccagactcaa gagaaccgct agaagaaggt acaccagaag aaagaacagg atctgctacc  15000
tccaagagat cttctctaac gagatggcta aagtggatga ttcattcttc cacaggctcg  15060
aagagtcatt cctcgtggaa gaagataaga agcacgagag gcaccctatc ttcggaaaca  15120
tcgttgatga ggtggcatac cacgagaagt accctactat ctaccacctc agaaagaagc  15180
tcgttgattc tactgataag gctgatctca ggctcatcta cctcgctctc gctcacatga  15240
tcaagttcag aggacacttc ctcatcgagg gtgatctcaa ccctgataac tctgatgtgg  15300
ataagttgtt catccagctc gtgcagacct acaaccagct tttcgaagag aaccctatca  15360
acgcttcagg tgtggatgct aaggctatcc tctctgctag gctctctaag tcaagaaggc  15420
ttgagaacct cattgctcag ctccctggtg agaagaagaa cggacttttc ggaaacttga  15480
tcgctctctc tctcggactc acccctaact tcaagtctaa cttcgatctc gctgaggatg  15540
caaagctcca gctctcaaag gatacctacg atgatgatct cgataacctc ctcgctcaga  15600
tcggagatca gtacgctgat ttgttcctcg ctgctaagaa cctctctgat gctatcctcc  15660
```

-continued

```
tcagtgatat cctcagagtg aacaccgaga tcaccaaggc tccactctca gcttctatga  15720
tcaagagata cgatgagcac caccaggatc tcacacttct caaggctctt gttagacagc  15780
agctcccaga gaagtacaaa gagattttct tcgatcagtc taagaacgga tacgctggtt  15840
acatcgatgg tggtgcatct caagaagagt tctacaagtt catcaagcct atcctcgaga  15900
agatggatgg aaccgaggaa ctcctcgtga agctcaatag agaggatctt ctcagaaagc  15960
agaggacctt cgataacgga tctatccctc atcagatcca cctcggagag ttgcacgcta  16020
tccttagaag gcaagaggat ttctacccat tcctcaagga taacagggaa aagattgaga  16080
agattctcac cttcagaatc ccttactacg tgggacctct cgctagagga aactcaagat  16140
tcgcttggat gaccagaaag tctgaggaaa ccatcacccc ttggaacttc gaagaggtgg  16200
tggataaggg tgctagtgct cagtctttca tcgagaggat gaccaacttc gataagaacc  16260
ttccaaacga gaaggtgctc cctaagcact ctttgctcta cgagtacttc accgtgtaca  16320
acgagttgac caaggttaag tacgtgaccg agggaatgag gaagcctgct tttttgtcag  16380
gtgagcaaaa gaaggctatc gttgatctct tgttcaagac caacagaaag gtgaccgtga  16440
agcagctcaa agaggattac ttcaagaaaa tcgagtgctt cgattcagtt gagatttctg  16500
gtgttgagga taggttcaac gcatctctcg gaacctacca cgatctcctc aagatcatta  16560
aggataagga tttcttggat aacgaggaaa acgaggatat cttggaggat atcgttctta  16620
ccctcaccct ctttgaagat agagagatga ttgaagaaag gctcaagacc tacgctcatc  16680
tcttcgatga taaggtgatg aagcagttga agagaagaag atacactggt tggggaaggc  16740
tctcaagaaa gctcattaac ggaatcaggg ataagcagtc tggaaagaca atccttgatt  16800
tcctcaagtc tgatggattc gctaacagaa acttcatgca gctcatccac gatgattctc  16860
tcacctttaa agaggatatc cagaaggctc aggtttcagg acagggtgat agtctccatg  16920
agcatatcgc taacctcgct ggatctcctg caatcaagaa gggaatcctc cagactgtga  16980
aggttgtgga tgagttggtg aaggtgatgg gaaggcataa gcctgagaac atcgtgatcg  17040
aaatggctag agagaaccag accactcaga agggacagaa gaactctagg gaaaggatga  17100
agaggatcga ggaaggtatc aaagagcttg gatctcagat cctcaaagag caccctgttg  17160
agaacactca gctccagaat gagaagctct acctctacta cctccagaac ggaagggata  17220
tgtatgtgga tcaagagttg gatatcaaca ggctctctga ttacgatgtt gatcatatcg  17280
tgccacagtc attcttgaag gatgattcta tcgataacaa ggtgctcacc aggtctgata  17340
agaacagggg taagagtgat aacgtgccaa gtgaagaggt tgtgaagaaa atgaagaact  17400
attggaggca gctcctcaac gctaagctca tcactcagag aaagttcgat aacttgacta  17460
aggctgagag gggaggactc tctgaattgg ataaggcagg attcatcaag aggcagcttg  17520
tggaaaccag gcagatcact aagcacgttg cacagatcct cgattctagg atgaacacca  17580
agtacgatga gaacgataag ttgatcaggg aagtgaaggt tatcaccctc aagtcaaagc  17640
tcgtgtctga tttcagaaag gatttccaat tctacaaggt gagggaaatc aacaactacc  17700
accacgctca cgatgcttac cttaacgctg ttgttggaac cgctctcatc aagaagtatc  17760
ctaagctcga gtcagagttc gtgtacggtg attacaaggt gtacgatgtg aggaagatga  17820
tcgctaagtc tgagcaagag atcggaaagg ctaccgctaa gtatttcttc tactctaaca  17880
tcatgaattt cttcaagacc gagattaccc tcgctaacgg tgagatcaga aagaggccac  17940
tcatcgagac aaacggtgaa acaggtgaga tcgtgtggga taagggaagg gatttcgcta  18000
ccgttagaaa ggtgctctct atgccacagg tgaacatcgt taagaaaacc gaggtgcaga  18060
```

-continued ccggtggatt ctctaaagag tctatcctcc ctaagaggaa ctctgataag ctcattgcta 18120
ggaagaagga ttgggaccct aagaaatacg gtggtttcga ttctcctacc gtggcttact 18180
ctgttctcgt tgtggctaag gttgagaagg gaaagagtaa gaagctcaag tctgttaagg 18240
aacttctcgg aatcactatc atggaaaggt catctttcga gaagaaccca atcgatttcc 18300
tcgaggctaa gggatacaaa gaggttaaga aggatctcat catcaagctc ccaaagtact 18360
cactcttcga actcgagaac ggtagaaaga ggatgctcgc ttctgctggt gagcttcaaa 18420
agggaaacga gcttgctctc ccatctaagt acgttaactt tctttacctc gcttctcact 18480
acgagaagtt gaagggatct ccagaagata acgagcagaa gcaacttttc gttgagcagc 18540
acaagcacta cttggatgag atcatcgagc agatctctga gttctctaaa agggtgatcc 18600
tcgctgatgc aaacctcgat aaggtgttgt ctgcttacaa caagcacaga gataagccta 18660
tcagggaaca ggcagagaac atcatccatc tcttcaccct taccaacctc ggtgctcctg 18720
ctgctttcaa gtacttcgat acaaccatcg ataggaagag atacacctct accaaagaag 18780
tgctcgatgc taccctcatc catcagtcta tcactggact ctacgagact aggatcgatc 18840
tctcacagct cggtggtgat tcaagggctg atcctaagaa gaagaggaag gtttgacgtc 18900
gacgatatga agatgaagat gaaatatttg gtgtgtcaaa taaaaagctt gtgtgcttaa 18960
gtttgtgttt ttttcttggc ttgttgtgtt atgaatttgt ggctttttct aatattaaat 19020
gaatgtaaga tcacattata atgaataaac aaatgtttct ataatccatt gtgaatgttt 19080
tgttggatct cttctgcagc atataactac tgtatgtgct atggtatgga ctatggaata 19140
tgattaaaga taagccagag ctctggtgac ggacggcgcg ctggcagaca tactgtccca 19200
caaatgaaga tggaatctgt aaaagaaaac gcgtgaaata atgcgtctga caaaggttag 19260
gtcggctgcc tttaatcaat accaaagtgg tccctaccac gatggaaaaa ctgtgcagtc 19320
ggtttggctt tttctgacga acaaataaga ttcgtggccg acaggtgggg gtccaccatg 19380
tgaaggcatc ttcagactcc aataatggag caatgacgta agggcttacg aaataagtaa 19440
gggtagtttg ggaaatgtcc actcacccgt cagtctataa atacttagcc cctccctcat 19500
tgttaaggga gcaaaatctc agagagatag tcctagagag agaaagagag caagtagcct 19560
agaagtagtc aaggcggcga agtattcagg cacgtggcca ggaagaagaa aagccaagac 19620
gacgaaaaca ggtaagagct aagcttcctg caggttcact gccgtatagg cagcattaac 19680
attaccatta acggttttag agctagaaat agcaagttaa aataaggcta gtccgttatc 19740
aacttgaaaa agtggcaccg agtcggtgcg ttcactgccg tataggcaga gggacaccaa 19800
tgtcctgctg ttttagagct agaaatagca agttaaaata aggctagtcc gttatcaact 19860
tgaaaaagtg gcaccgagtc ggtgcgttca ctgccgtata ggcaggtcga tcgacaagct 19920
cgagtttctc cataataatg tgtgagtagt tcccagataa gggaattagg gttcctatag 19980
ggtttcgctc atgtgttgag catataagaa acccttagta tgtatttgta tttgtaaaat 20040
acttctatca ataaaatttc taattcctaa aaccaaaatc cagtactaaa atccagatcc 20100
cccgaattag agctctaccg gcgagctttg ggtacgtcac gtggctcgag cgcgtagtcc 20160
tcggtaggca agcttattta attcatacag aagcaatctt tgtttcagat gttcactaca 20220
aaactcatcc tcttcttcaa tatttttggt ttcggaatga tcgctatctt aactcttttc 20280
cttacacatg gccgcaaacg cgttgatgtt cttggatgga tttgcatgat ctttgcttta 20340
tgcgtgtttg ttgcccccat gggtatcatg gtgagaatgc gagtcgcaaa tttcaacact 20400
tgcttctttc tgtctctgac agtttttttt ttttccccta taattatatt gattgatttt 20460

-continued

```
tgttttctct cttctttact ctattttcca gagaaaagtg ataaaaacga agagtgtcga  20520
gttcatgcca ttttctttat cattcttcct caccttgact gcggtgatgt ggttcttcta  20580
tggttttcta aagaaagacc tttatgttgc cgtaagttaa ctatcacgca tgcatcatta  20640
tcacgtacat ctttctttac attccaccaa ctttatcttt cccattaatc atcaacccag  20700
caactatttc ttattccctt ttgattaact tccacttaca atttcctttt tcttgtcatg  20760
aacagattcc aaacacattg ggctttcttt ttgggattgt ccagatggtg ctttatttaa  20820
tctacagaaa ccccaagaaa ttacctgtag aggatcctaa acttcgcgaa ttgtccgagc  20880
acatcgtcga cgttgcaaag ctgagtgcaa ccctctgttc cgagataacc acagtagtgg  20940
ttccacagcc catagacaat ggaaatgatg ttgaaggtca aaaaattaag gaagaaaacg  21000
agcaggacat tggtgtccct gcagacaaag ttaagactaa tctttttctc tttctcatct  21060
tttcacttct ccaatcatta tcctcggccg aattcagtaa aggagaagaa cttttcactg  21120
gagttgtccc aattcttgtt gaattagatg gtgatgttaa tgggcacaaa ttttctgtca  21180
gtggagaggg tgaaggtgat gcaacatacg gaaaacttac ccttaaattt atttgcacta  21240
ctggaaaact acctgttcca tggccaacac ttgtcactac tttcacttat ggtgttcaat  21300
gcttttcaag atacccagat catatgaagc ggcacgactt cttcaagagc gccatgcctg  21360
agggatacgt gcaggagagg accatctctt tcaaggacga cgggaactac aagacacgtg  21420
ctgaagtcaa gtttgaggga gacaccctcg tcaacaggat cgagcttaag ggaatcgatt  21480
tcaaggagga cggaaacatc ctcggccaca agttggaata caactacaac tcccacaacg  21540
tatacatcac ggcagacaaa caaaagaatg gaatcaaagc taacttcaaa attagacaca  21600
acattgaaga tggaagcgtt caactagcag accattatca acaaaatact ccaattggcg  21660
atggccctgt ccttttacca gacaaccatt acctgtccac acaatctgcc ctttcgaaag  21720
atcccaacga aaagagagac cacatggtcc ttcttgagtt tgtaacagct gctgggatta  21780
cacatggcat ggatgaacta tacaaacatg atgagctttg ataacattaa cattaccatt  21840
aacgtgatct tggttatgtt ttttcttttt aattttgcat gtaatcgttc aaagtggtgg  21900
tgccatgtct acttgtaagg ctgcaatgca gccatgttgt ctattatgtc aaatctagtt  21960
ccatttaatg tcaatcttta ttctcaacct aaaagaagaa tatcaatctt tatgtaatac  22020
gtttttttcga gtaaataaaa tgtccagtga atttacagtt aatgttaaat cagcattata  22080
ttttaggaaa atagtattca acttatagtt taatggttga aattaaatat taatttttat  22140
tttatgatgt aataatttta aatttaaatt atagctcctg gcaagagtta ttaataaaat  22200
aatactgcca atattttttt ctaaatttta tttgaatttg ttatttattt tatggaaaat  22260
atttttaaaa aataatttttc atattttttt atataagaag agctcaaaaa aattttaaat  22320
ccatgttatt ttacactaaa aaacagaagt ttaaataggg gagaaatttt tacattcgcc  22380
aacaaaacta tataaatttt tgttttgaat tataaaataa taattatttt tcctaaaaag  22440
aattcttcat gattgtgcca aataagtctc aatgcaattt taaaaaaaat ccagacaaaa  22500
tttgtcttat ttctcactgt gctatttttc taataagcat tttcattgtg caattaaatc  22560
tattggactc taatcaataa taaagaaaag ggataccttt aatcttttat cgaagatatc  22620
aactaattct agagcgcggt aatatcgcag aacaaaagta cctgatatcg agtgtacttc  22680
aagtcacacc ggcg                                                    22694
```

HOMOLOGOUS RECOMBINATION VIA TRANSCRIPTIONAL ACTIVATION

CROSS-REFERENCE TO RELATED APPLICATIONS

This application is a 35 U.S.C. 371 National Stage of International Application Number PCT/US2018/065756, filed Dec. 14, 2018, which claims the benefit of U.S. Provisional Patent Application No. 62/598,831 filed Dec. 14, 2017, the entire contents of which are hereby incorporated by reference in their entirety.

SEQUENCE LISTING

This application contains a Sequence Listing that has been submitted in ASCII format via EFS-Web and is hereby incorporated by reference in its entirety. The ASCII copy is named "077875-659415-US-Sequence-Listing.txt", and is 84 kilobytes in size.

FIELD OF THE INVENTION

The present disclosure provides compositions and methods of generating and identifying correct products of homologous recombination.

BACKGROUND OF THE INVENTION

Genome editing is a revolutionary technology that promises the ability to improve or overcome current deficiencies in the genetic code as well as to introduce novel functionality. However, some applications of the technology do not always generate completely reliable results. For instance, in organisms where the frequency of homologous recombination (HR) is low, the technology as currently practiced is only able to create random 'mistakes' at a user-defined location in the genome. For instance, in plants, where the frequency of homologous recombination is less than 1%, editing applications that require replacing an endogenous sequence with a user-defined sequence is possible only in theory. This means, identifying nucleic acid modifications of interest requires laborious screening and has a poor likelihood of success. In fact, in a typical scenario, it simply isn't possible to obtain the optimal, desired change.

Therefore, there is a long-felt need for improved and effective means of genome editing, especially in organisms where the frequency of homologous recombination (HR) is low. More specifically, there is a need for methods of identifying and isolating successful products of homologous recombination in genome editing.

SUMMARY OF THE INVENTION

One aspect of the present disclosure encompasses a homologous recombination composition. The composition comprises a homologous recombination system and a transcription activation system. The homologous recombination system comprises a programmable nucleic acid modification system, wherein the modification system targets a nucleic acid locus in a gene of interest. The programmable nucleic acid modification system comprises a donor polynucleotide encoding a reporter flanked by regions homologous to the nucleic acid locus. Expression of the reporter after homologous recombination and transcription activation of the gene of interest indicates an accurate homologous recombination event. The homologous recombination composition may generate an accurate homologous recombination event in a plant cell. The homologous recombination composition may be directed to one or more nucleic acid loci. The nucleic acid locus may be in a nuclear, organellar, or extrachromosomal gene of interest.

The programmable nucleic acid modification system may be an RNA-guided clustered regularly interspersed short palindromic repeats (CRISPR)/CRISPR-associated (Cas) (CRISPR/Cas) nuclease system, a CRISPR/Cpf1 nuclease system, a zinc finger nuclease (ZFN), a transcription activator-like effector nuclease (TALEN), a meganuclease, or a programmable DNA binding domain linked to a nuclease domain. The gene of interest may be a protein coding gene or an RNA coding gene, and the reporter may be a selectable or visual reporter.

The gene of interest may be a protein coding gene and the homologous recombination results in the reporter fused in frame with an open reading frame of the gene of interest, the reporter completely or partially replacing a coding sequence of the gene of interest, introduction of the reporter into an intron of the gene of interest, or in an untranslated region of a protein-producing gene of interest, or introduction of a stop codon such that expression of the gene of interest results in the expression of an unfused reporter, fusing the reporter at an N terminus, C terminus, or internally to a polypeptide fragment encoded by a partial open reading frame of the gene of interest. Alternatively, the gene of interest may be a protein-coding gene and the reporter may be a fluorescent RNA aptamer. Additionally, the gene of interest may be a RNA coding gene and the homologous recombination may further introduce a small RNA target site to knock out a IncRNA, one or more polymorphisms at 5' or 3' sequences of a miRNA precursor, or may further introduce in phase insertions or replacements of tasiRNAs or phasiRNAs in a tasi/phasiRNAs.

The transcription activation system may comprise a programmable endonuclease modified to lack all nuclease activity, a catalytically inactive Ago endonuclease, a catalytically inactive meganuclease, or a transcription activator-like effectors (TALEs) nucleic acid binding protein. The donor polynucleotide may further encodes sequence modifications in the gene of interest at or near a nucleic acid locus.

A promoter of the gene of interest may be replaced with a heterologous promoter. When a promoter is replaced, the donor polynucleotide may comprise a first nucleic acid sequence targeting a first nucleic acid locus for replacing endogenous promoter control sequences, and a second nucleic acid sequence at a second target nucleic acid locus for introducing the reporter in the gene of interest.

An intergenic nucleic acid sequence between two genes of interest may be modified. When an intergenic region is modified, the donor polynucleotide may encode a first replacement polynucleotide comprising a first reporter flanked by regions of homology to a first nucleic acid locus in a first gene of interest; a second replacement polynucleotide comprising a second reporter flanked by regions of homology to a second nucleic acid locus in a second gene of interest; and an intergenic construct flanked by the first replacement polynucleotide and the second replacement polynucleotide.

The transcription activation system and the homologous recombination system may be encoded on one or more expression constructs. In such an arrangement, expression of the transcription activation system may controlled by a tissue specific promoter. The tissue specific promoter may express the transcription activation system in screenable tissue.

Another aspect of the present disclosure encompasses a system of one or more nucleic acid constructs encoding one or more components of the homologous recombination compositions described above. The system may encode a programmable nucleic acid modification system, a donor polynucleotide encoding a reporter flanked by regions homologous to the nucleic acid locus, a transcription activation system specific for inducing expression of the gene of interest, and combinations thereof. Further, expression of the transcription activation system may be controlled by a tissue specific promoter.

Yet another aspect of the present disclosure encompasses a cell comprising the homologous recombination composition described above. The cell may be a eukaryotic cell, and the eukaryotic cell may be a plant cell. One or more components of the homologous recombination composition may be encoded by the one or more nucleic acid constructs described above.

Another aspect of the present disclosure encompasses a method of generating one or more accurate homologous recombination events in a cell. The method comprises providing one or more of the homologous recombination compositions described above; introducing into the cell the one or more homologous recombination compositions; and identifying an accurate homologous recombination event by identifying a cell expressing the reporter. The cell may be a eukaryotic cell, and the eukaryotic cell may be a plant cell. Additionally, the cell may be ex vivo.

An additional aspect of the present disclosure encompasses a library of homologous recombination compositions comprising two or more of the homologous recombination compositions described above. Each of the two or more homologous recombination compositions targets a distinct nucleic acid locus. The library may target all genes in a genome of a cell. Each of the two or more homologous recombination compositions may knock out a distinct gene of interest. The homologous recombination system may be a CRISPR nuclease system and the transcription activation system is based on a CRISPR nuclease system.

The library may comprise two or more homologous recombination constructs. Each construct comprises a nucleic acid cassette specific for a distinct nucleic acid locus comprising a nucleic acid expression construct encoding a gRNA of the CRISPR-based nucleic acid modification system specific for the nucleic acid locus, a nucleic acid expression construct encoding a gRNA of the CRISPR-based transcription activation system, and a donor polynucleotide encoding a reporter flanked by regions homologous to the nucleic acid locus; and a modular homologous recombination construct comprising a backbone encoding additional components of the CRISPR-based nucleic acid modification system and the CRISPR-based transcription activation system.

Another aspect of the present disclosure encompasses a kit comprising one or more of the homologous recombination compositions described above, wherein each of the homologous recombination compositions targets a distinct nucleic acid locus. Each of the one or more homologous recombination compositions may be encoded by a system of one or more of the nucleic acid constructs described above. The kit may comprise one or more cells comprising one or more of the homologous recombination compositions described above, a system of one or more nucleic acid constructs described above, or combinations thereof.

REFERENCE TO COLOR FIGURES

The application file contains at least one figure executed in color. Copies of this patent application publication with color figure will be provided by the Office upon request and payment of the necessary fee.

DETAILED DESCRIPTION

Figure 1:
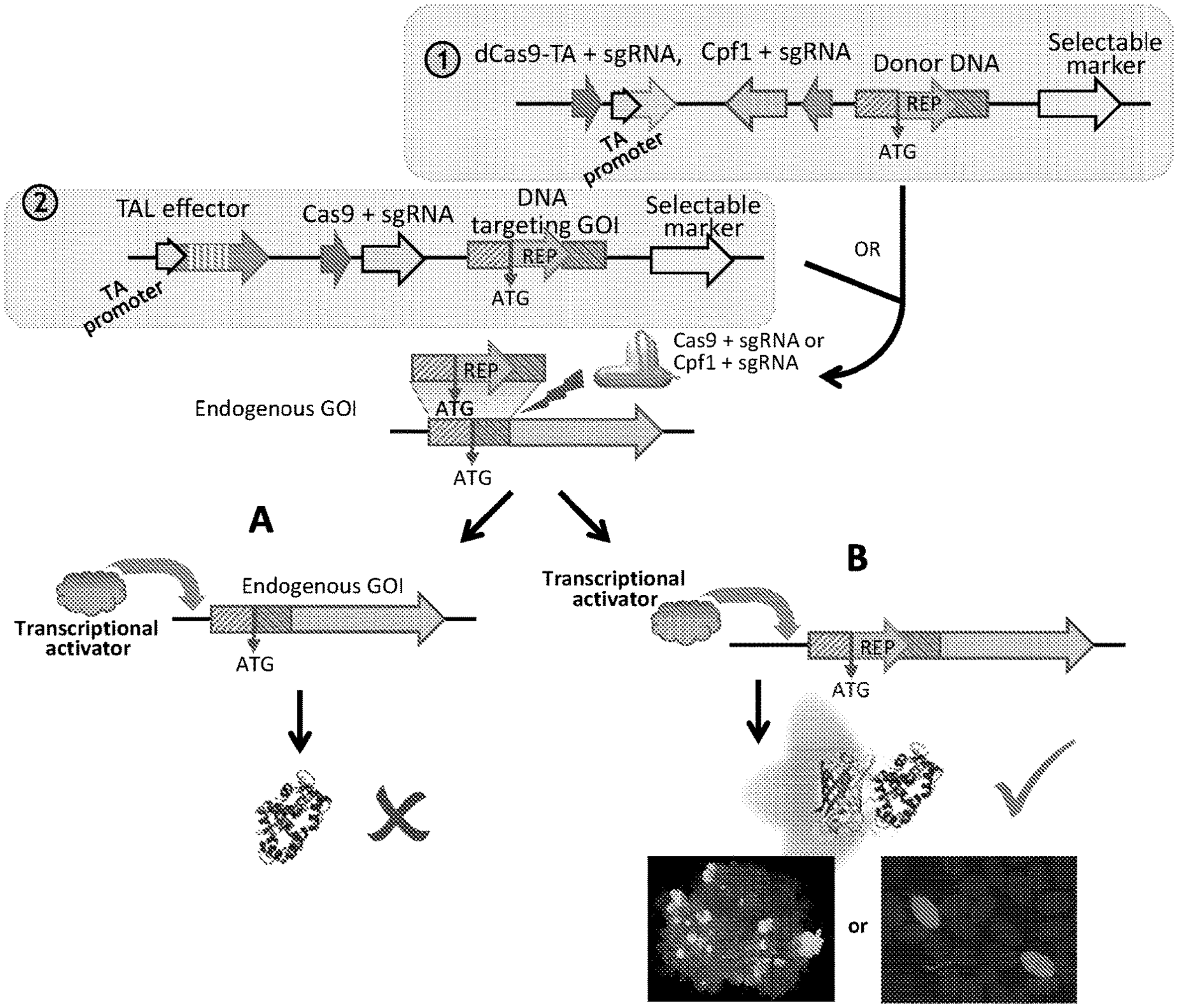
FIG. 1 depicts a schematic overview of the strategy of using a transcriptional activator to identify in-frame gene fusions, products of homologous recombination. Panel 1 depicts an aspect of a DNA construct encoding a donor polynucleotide (DNA targeting gene of interest (GOI)) comprising a reporter flanked by regions homologous to a nucleic acid locus, Cpf1 nickase and single guide RNA, and a CRISPR-based transcription activator with associated sgRNA. Panel 2 depicts an alternative aspect of a DNA construct of Panel 1. In Panel 2, a TAL effector is used for transcriptional activation instead of a CRISPR-based transcription activator. Panels A and B depict the two possible outcomes in the strategy. Panel A depicts an outcome wherein the reporter is not inserted. Panel B depicts an outcome wherein the reporter is inserted, and expressed by the transcription activator.

The present disclosure is based in part on the surprising discovery that combining a homologous recombination system with a transcription activation system may be used to efficiently and consistently generate and identify an accurate homologous recombination event. Strategies of the discovery may be as depicted in FIGS. 1-7. Essentially, a homologous recombination system induces homologous recombination of a donor polynucleotide at a specific nucleic acid locus in a gene of interest (see, e.g., FIG. 1). A donor polynucleotide encodes a reporter flanked by regions homologous to the nucleic acid locus for introducing the reporter at the nucleic acid locus. A transcription activation system specifically induces expression of the gene of interest. In the event of an inaccurate homologous recombination event, the reporter is not introduced into the gene of interest at the target nucleic acid locus, and is not expressed when the expression of the gene of interest is activated by the transcription activation system (FIG. 1, Panel A). Conversely, expression of the reporter after homologous recombination indicates an accurate homologous recombination event, and identifies the accurate homologous recombination event (FIG. 1, Panel B).

I. Composition

In one aspect, the present disclosure provides a homologous recombination composition for inducing and identifying an accurate recombination event. The composition comprises a homologous recombination system and a transcription activation system. The homologous recombination system comprises a programmable nucleic acid modification system, wherein the modification system targets a nucleic acid locus in a gene of interest. The homologous recombination system further comprises a donor polynucleotide encoding a reporter flanked by regions homologous to the nucleic acid locus. The transcription activation system is specific for inducing expression of the gene of interest, wherein expression of the reporter after homologous recombination indicates an accurate homologous recombination event. A homologous recombination composition may be directed to one or more, or two or more nucleic acid loci.

(a) Homologous Recombination System

As used herein, the term "homologous recombination system" refers to any system capable of inducing and generating a homologous recombination event at a target nucleic acid locus, and that may lead to the replacement of nucleic acid sequences at or near the target nucleic acid locus with nucleic acid sequences of a donor polynucleotide. A homologous recombination system of the disclosure generally comprises a programmable nucleic acid modification system and a donor polynucleotide. The programmable nucleic acid modification system targets a nucleic acid locus in a gene of interest and induces homologous recombination at the target nucleic acid locus. The donor polynucleotide encodes a reporter flanked by regions homologous to the nucleic acid locus. In the presence of the donor polynucleotide, homologous recombination may lead to the replacement of nucleic acid sequences at or near the target nucleic acid locus with nucleic acid sequences of the donor polynucleotide.

A. Programmable Nucleic Acid Modification Systems

Programmable nucleic acid modification systems generally comprise a programmable, sequence-specific nucleic acid-binding domain, and a modification domain. The programmable nucleic acid-binding domain may be designed or engineered to recognize and bind different nucleic acid sequences. In some modification systems, the nucleic acid-binding domain is mediated by interaction between a protein and the target nucleic acid sequence. Thus, the nucleic acid-binding domain may be programmed to bind a nucleic acid sequence of interest by protein engineering. In other modification systems, the nucleic acid-binding domain is mediated by a guide nucleic acid that interacts with a protein of the modification system and the target nucleic acid sequence. In such instances, the programmable nucleic acid-binding domain may be targeted to a nucleic acid sequence of interest by designing the appropriate guide nucleic acid.

The programmable nucleic acid modification system further comprises a nuclease modification domain and, thus, has nuclease activity. Thus, a programmable nucleic acid modification protein of the modification system is a targeting endonuclease that cleaves a nucleic acid at a targeted site. The cleavage may be double-stranded or single-stranded. The cleavage may be repaired by homology directed repair (HDR) or non-homologous end-joining (NHEJ) repair processes. Non-limiting examples of programmable nucleic acid modification systems include, without limit, CRISPR/Cas nucleases, CRISPR/Cas nickases, DNA-guided Argonaute endonucleases, zinc finger nucleases, transcription activator-like effector nucleases, meganucleases, or chimeric proteins comprising a programmable nucleic acid-binding domain and a nuclease domain. Other suitable programmable nucleic acid modification systems will be recognized by individuals skilled in the art. Programmable nucleic acid modification systems may be as detailed below in Sections (I)(a)(A)(i)-(vii).

i. CRISPR Nuclease Systems

The programmable nucleic acid modification system may be a RNA-guided CRISPR nuclease system. The CRISPR system is guided by a guide RNA to a target sequence at which a protein of the system introduces a double-stranded break in a target nucleic acid sequence.

The CRISPR nuclease system may be derived from any type of CRISPR system, including a type I (i.e., IA, IB, IC, ID, IE, or IF), type II (i.e., IIA, IIB, or IIC), type III (i.e., IIIA or IIIB), or type V CRISPR system. The CRISPR/Cas system may be from *Streptococcus* sp. (e.g., *Streptococcus pyogenes*), *Campylobacter* sp. (e.g., *Campylobacter jejuni*), *Francisella* sp. (e.g., *Francisella novicida*), *Acaryochloris* sp., *Acetohalobium* sp., *Acidaminococcus* sp., *Acidithiobacillus* sp., *Alicyclobacillus* sp., *Allochromatium* sp., *Ammonifex* sp., *Anabaena* sp., *Arthrospira* sp., *Bacillus* sp., *Burkholderiales* sp., *Caldicelulosiruptor* sp., *Candidatus* sp., *Clostridium* sp., *Crocosphaera* sp., *Cyanothece* sp., *Exiguobacterium* sp., *Finegoldia* sp., *Ktedonobacter* sp., *Lactobacillus* sp., *Lyngbya* sp., *Marinobacter* sp., *Methanohalobium* sp., *Microscilla* sp., *Microcoleus* sp., *Microcystis* sp., *Natranaerobius* sp., *Neisseria* sp., *Nitrosococcus* sp., *Nocardiopsis* sp., *Nodularia* sp., *Nostoc* sp., *Oscillatoria* sp., *Polaromonas* sp., *Pelotomaculum* sp., *Pseudoalteromonas* sp., *Petrotoga* sp., *Prevotella* sp., *Staphylococcus* sp., *Streptomyces* sp., *Streptosporangium* sp., *Synechococcus* sp., or *Thermosipho* sp.

Non-limiting examples of suitable CRISPR systems include CRISPR/Cas systems, CRISPR/Cpf systems, CRISPR/Cmr systems, CRISPR/Csa systems, CRISPR/Csb systems, CRISPR/Csc systems, CRISPR/Cse systems, CRISPR/Csf systems, CRISPR/Csm systems, CRISPR/Csn systems, CRISPR/Csx systems, CRISPR/Csy systems, CRISPR/Csz systems, and derivatives or variants thereof. Preferably, the CRISPR system may be a type II Cas9 protein, a type V Cpf1 protein, or a derivative thereof. More preferably, the CRISPR/Cas nuclease may be *Streptococcus pyogenes* Cas9 (SpCas9), *Streptococcus thermophilus* Cas9 (StCas9), *Campylobacter jejuni* Cas9 (CjCas9), *Francisella novicida* Cas9 (FnCas9), or *Francisella novicida* Cpf1 (FnCpf1).

In general, a protein of the CRISPR system comprises a RNA recognition and/or RNA binding domain, which interacts with the guide RNA. A protein of the CRISPR system also comprises at least one nuclease domain having endonuclease activity. For example, a Cas9 protein may comprise a RuvC-like nuclease domain and a HNH-like nuclease domain, and a Cpf1 protein may comprise a RuvC-like domain. A protein of the CRISPR system may also comprise DNA binding domains, helicase domains, RNase domains, protein-protein interaction domains, dimerization domains, as well as other domains.

A protein of the CRISPR system may be associated with one or more guide RNAs (gRNA). The guide RNA may be a single guide RNA (i.e., sgRNA), or may comprise two RNA molecules (i.e., crRNA and tracrRNA). The guide RNA interacts with a protein of the CRISPR system to guide it to a target site in the DNA. The target site has no sequence limitation except that the sequence is bordered by a protospacer adjacent motif (PAM). For example, PAM sequences for Cas9 include 3'-NGG, 3'-NGGNG, 3'-NNAGAAW, and 3'-ACAY, and PAM sequences for Cpf1 include 5'-TTN (wherein N is defined as any nucleotide, W is defined as either A or T, and Y is defined as either C or T). Each gRNA comprises a sequence that is complementary to the target sequence (e.g., a Cas9 gRNA may comprise GN17-20GG). The gRNA may also comprise a scaffold sequence that forms a stem loop structure and a single-stranded region. The scaffold region may be the same in every gRNA. In some aspects, the gRNA may be a single molecule (i.e., sgRNA). In other aspects, the gRNA may be two separate molecules.

Those skilled in the art are familiar with gRNA design and construction, e.g., gRNA design tools are available on the internet or from commercial sources.

A CRISPR system may comprise one or more nucleic acid binding domains associated with one or more, or two or more selected guide RNAs used to direct the CRISPR system to one or more, or two or more selected target nucleic acid loci. For instance, a nucleic acid binding domain may be associated with one or more, or two or more selected guide RNAs, each selected guide RNA, when complexed with a nucleic acid binding domain, causing the CRISPR system to localize to the target of the guide RNA.

ii. CRISPR Nickase Systems

The programmable nucleic acid modification system may also be a CRISPR nickase system. CRISPR nickase systems are similar to the CRISPR nuclease systems described above except that a CRISPR nuclease of the system is modified to cleave only one strand of a double-stranded nucleic acid sequence. Thus, a CRISPR nickase in combination with a guide RNA of the system may create a single-stranded break or nick in the target nucleic acid sequence. Alternatively, a CRISPR nickase in combination with a pair of offset gRNAs may create a double-stranded break in the nucleic acid sequence.

A CRISPR nuclease of the system may be converted to a nickase by one or more mutations and/or deletions. For example, a Cas9 nickase may comprise one or more mutations in one of the nuclease domains, wherein the one or more mutations may be D10A, E762A, and/or D986A in the RuvC-like domain, or the one or more mutations may be H840A (or H839A), N854A and/or N863A in the HNH-like domain.

iii. ssDNA-Guided Argonaute Systems

Alternatively, the programmable nucleic acid modification system may comprise a single-stranded DNA-guided Argonaute endonuclease. Argonautes (Agos) are a family of endonucleases that use 5'-phosphorylated short single-stranded nucleic acids as guides to cleave nucleic acid targets. Some prokaryotic Agos use single-stranded guide DNAs and create double-stranded breaks in nucleic acid sequences. The ssDNA-guided Ago endonuclease may be associated with a single-stranded guide DNA.

The Ago endonuclease may be derived from *Alistipes* sp., *Aquifex* sp., *Archaeoglobus* sp., *Bacteriodes* sp., *Bradyrhizobium* sp., *Burkholderia* sp., *Cellvibrio* sp., *Chlorobium* sp., *Geobacter* sp., *Mariprofundus* sp., *Natronobacterium* sp., *Parabacteriodes* sp., *Parvularcula* sp., *Planctomyces* sp., *Pseudomonas* sp., *Pyrococcus* sp., *Thermus* sp., or *Xanthomonas* sp. For instance, the Ago endonuclease may be *Natronobacterium gregoryi* Ago (NgAgo). Alternatively, the Ago endonuclease may be *Thermus thermophilus* Ago (TtAgo). The Ago endonuclease may also be *Pyrococcus furiosus* (PfAgo).

The single-stranded guide DNA (gDNA) of a ssDNA-guided Argonaute system is complementary to the target site in the nucleic acid sequence. The target site has no sequence limitations and does not require a PAM. The gDNA generally ranges in length from about 15-30 nucleotides. The gDNA may comprise a 5' phosphate group. Those skilled in the art are familiar with ssDNA oligonucleotide design and construction.

iv. Zinc Finger Nucleases

The programmable nucleic acid modification system may be a zinc finger nuclease (ZFN). A ZFN comprises a DNA-binding zinc finger region and a nuclease domain. The zinc finger region may comprise from about two to seven zinc fingers, for example, about four to six zinc fingers, wherein each zinc finger binds three nucleotides. The zinc finger region may be engineered to recognize and bind to any DNA sequence. Zinc finger design tools or algorithms are available on the internet or from commercial sources. The zinc fingers may be linked together using suitable linker sequences.

A ZFN also comprises a nuclease domain, which may be obtained from any endonuclease or exonuclease. Non-limiting examples of endonucleases from which a nuclease domain may be derived include, but are not limited to, restriction endonucleases and homing endonucleases. The nuclease domain may be derived from a type II-S restriction endonuclease. Type II-S endonucleases cleave DNA at sites that are typically several base pairs away from the recognition/binding site and, as such, have separable binding and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. The type II-S nuclease domain may be modified to facilitate dimerization of two different nuclease domains. For example, the cleavage domain of FokI may be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI nuclease domains are targets for modification. For example, one modified FokI domain may comprise Q486E, I499L, and/or N496D mutations, and the other modified FokI domain may comprise E490K, I538K, and/or H537R mutations.

v. Transcription Activator-Like Effector Nuclease Systems

The programmable nucleic acid modification system may also be a transcription activator-like effector nuclease (TALEN) or the like. TALENs comprise a DNA-binding domain composed of highly conserved repeats derived from transcription activator-like effectors (TALEs) that are linked to a nuclease domain. TALEs are proteins secreted by plant pathogen *Xanthomonas* to alter transcription of genes in host plant cells. TALE repeat arrays may be engineered via modular protein design to target any DNA sequence of interest. Other transcription activator-like effector nuclease systems may comprise, but are not limited to, the repetitive sequence, transcription activator like effector (RipTAL) system from the bacterial plant pathogenic *Ralstonia solanacearum* species complex (Rssc). The nuclease domain of TALEs may be any nuclease domain as described above in Section (I)(a)(A)(i).

vi. Meganucleases or Rare-Cutting Endonuclease Systems

The programmable nucleic acid modification system may also be a meganuclease or derivative thereof. Meganucleases are endodeoxyribonucleases characterized by long recognition sequences, i.e., the recognition sequence generally ranges from about 12 base pairs to about 45 base pairs. As a consequence of this requirement, the recognition sequence generally occurs only once in any given genome. Among meganucleases, the family of homing endonucleases named LAGLIDADG has become a valuable tool for the study of genomes and genome engineering. In some aspects, the meganuclease may be I-SceI or variants thereof. A meganuclease may be targeted to a specific nucleic acid sequence by modifying its recognition sequence using techniques well known to those skilled in the art.

The programmable DNA modification system having nuclease activity may be a rare-cutting endonuclease or derivative thereof. Rare-cutting endonucleases are site-specific endonucleases whose recognition sequence occurs rarely in a genome, preferably only once in a genome. The rare-cutting endonuclease may recognize a 7-nucleotide sequence, an 8-nucleotide sequence, or longer recognition sequence. Non-limiting examples of rare-cutting endonucleases include NotI, AscI, PacI, AsiSI, SbfI, and FseI.

vii. Optional Additional Domains

The programmable nucleic acid modification system may further comprise at least one nuclear localization signal (NLS), at least one cell-penetrating domain, at least one reporter domain, and/or at least one linker.

In general, an NLS comprises a stretch of basic amino acids. Nuclear localization signals are known in the art (see, e.g., Lange et al., J. Biol. Chem., 2007, 282:5101-5105). For example, in one aspect, the NLS may be a monopartite sequence, such as PKKKRKV (SEQ ID NO: 1) or PKKKRRV (SEQ ID NO: 2). Alternatively, the NLS may be a bipartite sequence. Further, the NLS may be KRPAATKKAGQAKKKK (SEQ ID NO: 3). The NLS may be located at the N-terminus, the C-terminal, or in an internal location of the fusion protein.

A cell-penetrating domain may be a cell-penetrating peptide sequence derived from the HIV-1 TAT protein. As an example, the TAT cell-penetrating sequence may be GRKKRRQRRRPPQPKKKRKV (SEQ ID NO: 4). Alternatively, the cell-penetrating domain may be TLM (PLSSIFSRIGDPPKKKRKV; SEQ ID NO: 5), a cell-penetrating peptide sequence derived from the human hepatitis B virus; MPG (GALFLGWLGAAGSTMGAPKKKRKV; SEQ ID NO: 6; or GALFLGFLGAAGSTMGAWSQPKKKRKV; SEQ ID NO: 7); or Pep-1 (KETWWETWVVTEWSQPKKKRKV; SEQ ID NO: 8), VP22, a cell-penetrating peptide from Herpes simplex virus, or a polyarginine peptide sequence. The cell-penetrating domain may be located at the N-terminus, the C-terminal, or in an internal location of the fusion protein.

A programmable nucleic acid modification system may further comprise at least one reporter domain. Non-limiting examples of reporter domains include fluorescent proteins, purification tags, and epitope tags. In some aspects, the reporter domain may be a fluorescent protein. Non-limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (e.g., mOrange, mKO, Kusabira-Orange, Monomeric Kusabira-Orange, mTangerine, tdTomato), or any other suitable fluorescent protein. In other aspects, the reporter domain may be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6xHis, biotin carboxyl carrier protein (BCCP), and calmodulin.

A programmable nucleic acid modification system may further comprise at least one linker. For example, the programmable nucleic acid modification system, the nuclease domain of a protein, and other optional domains may be linked via one or more linkers. The linker may be flexible (e.g., comprising small, non-polar (e.g., Gly) or polar (e.g., Ser, Thr) amino acids). Non-limiting examples of flexible linkers include GGSGGGSG (SEQ ID NO:9), (GGGGS)1-4 (SEQ ID NO:10), and (Gly)6-8. Alternatively, the linker may be rigid, such as (EAAAK)1-4 (SEQ ID NO:11), A(EAAAK)2-5A (SEQ ID NO:12), PAPAP (AP)6-8, and (XP)n, wherein X is any amino acid, but preferably Ala, Lys, or Glu. Examples of suitable linkers are well known in the art, and programs to design linkers are readily available (Crasto et al., Protein Eng., 2000, 13(5):3096-312). In alternate aspects, the programmable DNA modification protein, the cell cycle regulated protein, and other optional domains may be linked directly.

A programmable nucleic acid modification system may further comprise an organelle localization or targeting signal that directs a molecule to a specific organelle. A signal may be polynucleotide or polypeptide signal, or may be an organic or inorganic compound sufficient to direct an attached molecule to a desired organelle. Exemplary organelle localization signals may be as described in U.S. Patent Publication No. 20070196334, the disclosure of which is incorporated herein in its entirety.

B. Donor Polynucleotide

Programmable nucleic acid modification systems also comprise a donor polynucleotide. In the presence of the donor polynucleotide, homologous recombination may lead to the replacement of nucleic acid sequences at or near the target nucleic acid locus with nucleic acid sequences of the donor polynucleotide. The donor polynucleotide encodes a reporter flanked by regions homologous to the nucleic acid locus in a gene of interest.

A donor polynucleotide may be an RNA or DNA, single-stranded or double-stranded, linear or circular. The donor polynucleotide may be part of a vector, e.g., a plasmid or viral vector as described in Section II.

i. Reporter

The donor polynucleotide encodes a reporter. As used herein, the term "reporter" refers to any biomolecule that may be used as an indicator of transcription and/or translation through a promoter. A reporter may be a polypeptide. A reporter may also be a nucleic acid. Suitable polypeptide and nucleic acid reporters are known in the art, and may include visual reporters, selectable reporters, screenable reporters, and combinations thereof. Other types of reporters will be recognized by individuals of skill in the art.

Visual reporters typically result in a visual signal, such as a color change in the cell, or fluorescence or luminescence of the cell. Suitable visual reporters include fluorescent proteins, visible reporters, epitope tags, affinity tags, RNA aptamers, and the like. Non-limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (e.g., mOrange, mKO, Kusabira-Orange, Monomeric Kusabira-Orange, mTangerine, tdTomato), or any other suitable fluorescent protein. Non-limiting examples of visual reporters include luciferase, alkaline phosphatase, beta-glucuronidase (GUS), beta-galactosidase, beta-lactamase, horseradish peroxidase, anthocyanin pigmentation, and variants thereof. Suitable epitope tags include, but are not limited to, myc, AcV5, AU1, AU5, E, ECS, E2, FLAG, HA, Maltose binding protein, nus, Softag 1, Softag 3, Strep, SBP, Glu-Glu, HSV, KT3, S, 51, T7, V5, VSV-G, 6xHis, BCCP, and calmodulin. Non-limiting examples of affinity tags include chitin binding protein (CBP), thioredoxin (TRX), poly(NANP), tandem affinity purification (TAP) tag, and glutathione-S-transferase (GST). Non-limiting examples of RNA aptamers include fluorescent RNA aptamers that sequester small molecule dyes and activate their fluorescence, such as spinach, broccoli, mango, or biliverdin-binding variants thereof.

Other visual reporters may include fluorescent resonance energy transfer (FRET), lanthamide resonance energy transfer (LRET), fluorescence cross-correlation spectroscopy, fluorescence quenching, fluorescence polarization, scintillation proximity, chemiluminescence energy transfer, bioluminescence resonance energy transfer, excimer formation, phosphorescence, electrochemical changes, molecular beacons, and redox potential changes.

Selectable reporters typically confer a positively or negatively selectable trait to a cell, such as a drug resistance (e.g., antibiotic resistance) positive selection reporter. Examples of suitable selectable reporters include, without limit, herbicide resistance or tolerance such as resistance to glyphosate, glufosinate ammonium, bromoxynil, 2,4-dichlorophenoxyacetate (2,4-D), or sulfonylurea herbicides, antibiotic or chemical selectable reporters such as puromycin, zeomycin, streptomycin, chloramphenicol, gentamycin, neomycin, hydromycin, phleomycin, hygromycin, bleomycin, sulfonamide, bromoxynil, spectinomycin, methotrexate, and the like. Additional examples include dihydrofolate reductase, 5-eno/pyruvylshikimate-3-phosphate synthase, and acetolactate synthase, neomycin phosphotransferase I and II, cyanamide hydratase, aspartate kinase, dihydrodipicolinate synthase, bar gene, tryptophane decarboxylase, hygromycin phosphotransferase (HPT or HYG), dihydrofolate reductase (DHFR), phosphinothricin acetyltransferase, 2,2-dichloropropionic acid dehalogenase, acetohydroxyacid synthase, 5-enolpyruvyl-shikimate-phosphate synthase, haloarylnitrilase, acetyl-coenzyme A carboxylase, dihydropteroate synthase, and 32 kDa photosystem II polypeptide (psbA).

Additionally, selectable reporters may include environmental or artificial stress resistance or tolerance reporters including, but not limited to, high glucose tolerance, low phosphate tolerance, mannose tolerance, and/or drought tolerance, salt tolerance or cold tolerance. Reporters that confer environmental or artificial stress resistance or tolerance include, but are not limited to, trehalose phosphate synthase, phophomannose isomerase, *Arabidopsis* vacuolar H+-pyrophosphatase, AVPI, aldehyde resistance, and cyanamide resistance.

Other reporters may also be morphogenic reporters. A morphogenic reporter may be any reporter capable of inducing a morphogenic trait that may be used to identify and isolate successful products of homologous recombination. For instance, a morphogenic reporter may be used to activate proliferation of cells that have correct insertion in a desired target gene of interest, when transcriptional activation of the target in the callus occurs. Such a reporter causes cells with the successful event to out-proliferate any other cell. Alternatively, a morphogenic reporter may be used to induce organogenesis by cells that have an correct homologous recombination event in a desired target gene of interest, when transcriptional activation of the target in the callus occurs. Such a reporter causes cells with the successful event to produce a plant instead thereby identifying the successful event. Non-limiting examples of morphogenic reporters include promoters of cellular proliferation. For instance, a morphogenic reporter may be a transcription factor that promotes stem cell proliferation or organogenesis. Non-limiting examples of morphogenic promoters may include the maize (*Zea mays*) Baby boom (Bbm), the maize Wuschel2 (Wus2) genes, and combinations thereof.

It will be recognized that combinations of reporters may be used. For instance, a visual reporter fused to a protein expressed by the gene of interest may be used to identify an accurate homologous recombination event, but the visual reporter is not permanently fused to the protein (see, e.g. FIG. 2). A second reporter may be used in combination with the visual reporter, wherein the second reporter is permanently fused to the protein.

Additionally, irrespective of the reporter used in a donor polynucleotide, the reporter may be a split reporter system. Split reporter systems may be used to reduce the size of a reporter sequence introduced into a target nucleic acid locus. Non-limiting examples of suitable split reporter systems include split GFP systems, split 5-EnolpyruvylShikimate-3-Phosphate Synthase for glyphosate resistance, among others. Similarly, irrespective of the reporter used, a donor polynucleotide may encode an activator for activating a reporter encoded in a location other than the donor polynucleotide. For instance, a donor polynucleotide may encode an activator for activating a reporter encoded on nucleic acid sequences introduced into a cell with the donor polynucleotide, such as T-DNA nucleic acid sequences.

ii. Gene of Interest

As used herein, the term "gene" refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions. Therefore, a target nucleic acid locus may be within any sequence in the gene of interest, including, but not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

As used herein, the term "encode" refers to is understood to have its plain and ordinary meaning as used in the biological fields, i.e., specifying a biological sequence. The term "encode," when used to describe the function of nucleic acid molecules, customarily means to identify one single amino acid sequence that makes up a unique polypeptide, or one nucleic acid sequence that makes up a unique RNA. That function is implemented by the particular nucleotide sequence of each nucleic acid molecule. In this aspect, the term "encode" refers to a reporter operably linked to the regions of homology such that the reporter is expressed upon accurate homologous recombination into the gene of interest and upon transcription activation of the gene of interest comprising the locus of interest. As used herein, the term "express" refers to the conversion of DNA sequence information into messenger RNA (mRNA) and/or protein. In this aspect, the term "express" refers to production of a detectable reporter signal as a result of an accurate homologous recombination event and transcription activation of the gene of interest.

Figure 6:
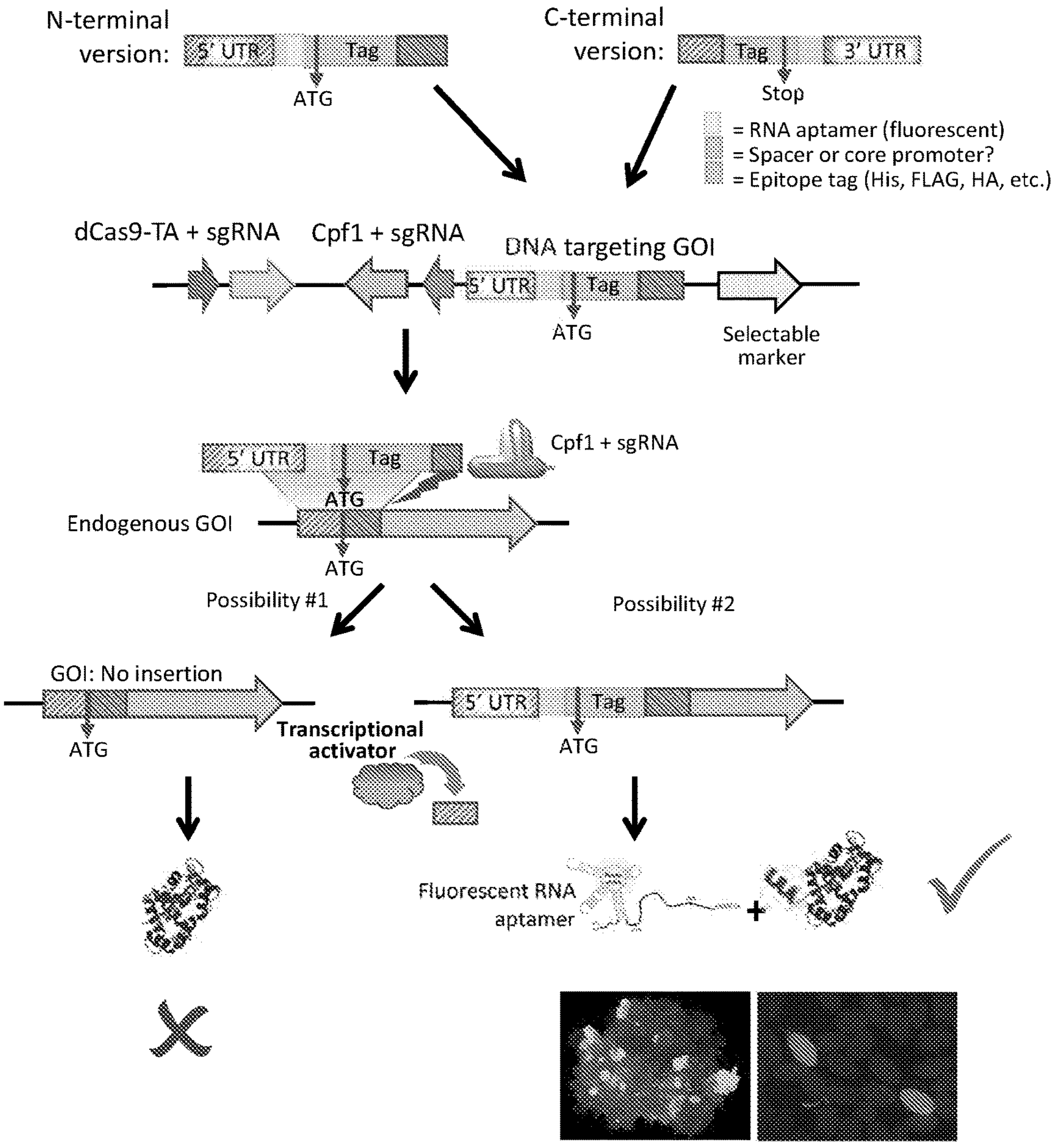
FIG. 6 schematically depicts a variant of the strategy depicted in FIG. 1, using a fluorescent RNA aptamer to detect in-frame fusions of non-visual epitope tags. In this variation, visual detection of insertion is detected using a short (40 to 100 nt) fluorescent RNA aptamer. In this aspect, these RNA aptamers are located in the 5' UTR upstream of the start codon. A short epitope tag fused in-frame with the open reading frame of the gene of interest is also shown.

The gene of interest may be a protein coding gene or an RNA coding gene. When the gene of interest is a protein coding gene, the reporter may be encoded in-frame with an open reading frame of the gene of interest such that expression of the gene of interest results in the expression of a fusion protein comprising the reporter polypeptide and the polypeptide encoded by the gene of interest (See, for example, FIGS. 1, 2, 4). In-frame reporters may be fused at the N terminus, C terminus, or internally to the polypeptide encoded by the gene of interest. In a variation, the reporter may completely or partially replace a coding sequence of the gene of interest, or introduce a stop codon such that expression of the gene of interest results in the expression of an unfused reporter, or a reporter fused at the N terminus, C terminus, or internally to a polypeptide fragment encoded by the partial open reading frame of the gene of interest (FIG. 3). Additionally, the reporter may be encoded in an intron of a gene of interest, or in an untranslated region of a protein-producing gene of interest, such that the reporter is expressed upon transcription of the gene of interest (FIG. 6).

Figure 7A:
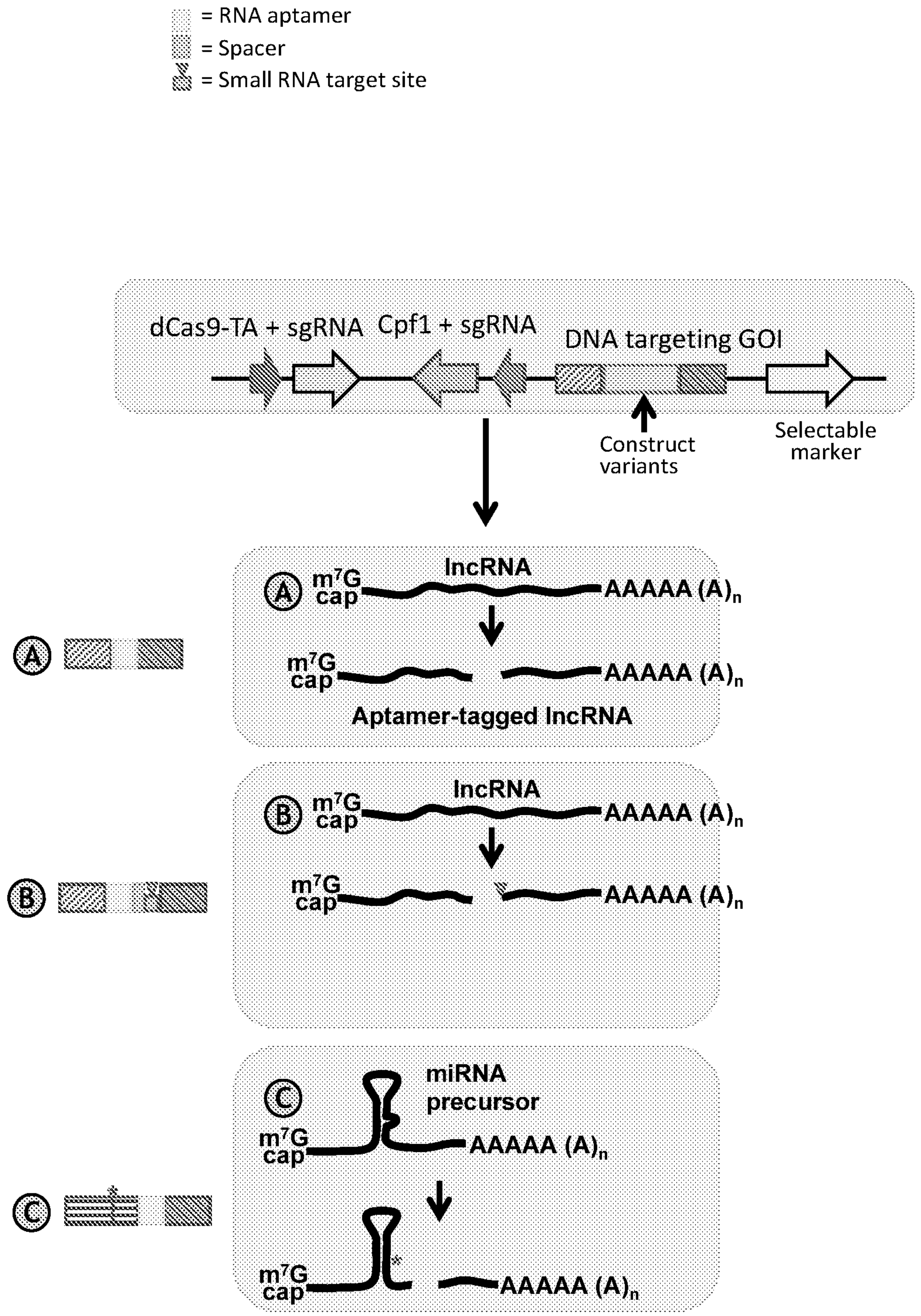
FIG. 7A schematically depicts a variant of the strategy depicted in FIG. 1, using a fluorescent RNA aptamer to create fusions with genes encoding lncRNA. Construct (A) and Panel (A) depicts an aspect wherein the gene encodes a long non-coding RNA. Construct (B) and Panel (B) depicts an aspect wherein a small RNA target site is introduced into the LNCRNA to "knock out" the lncRNA in addition to the fluorescent RNA aptamer. Construct (C) and Panel (C) depicts an aspect wherein the gene encodes a miRNA precursor, and a polymorphism is introduced (red asterisk) in addition to the fluorescent RNA aptamer.
Figure 7B:
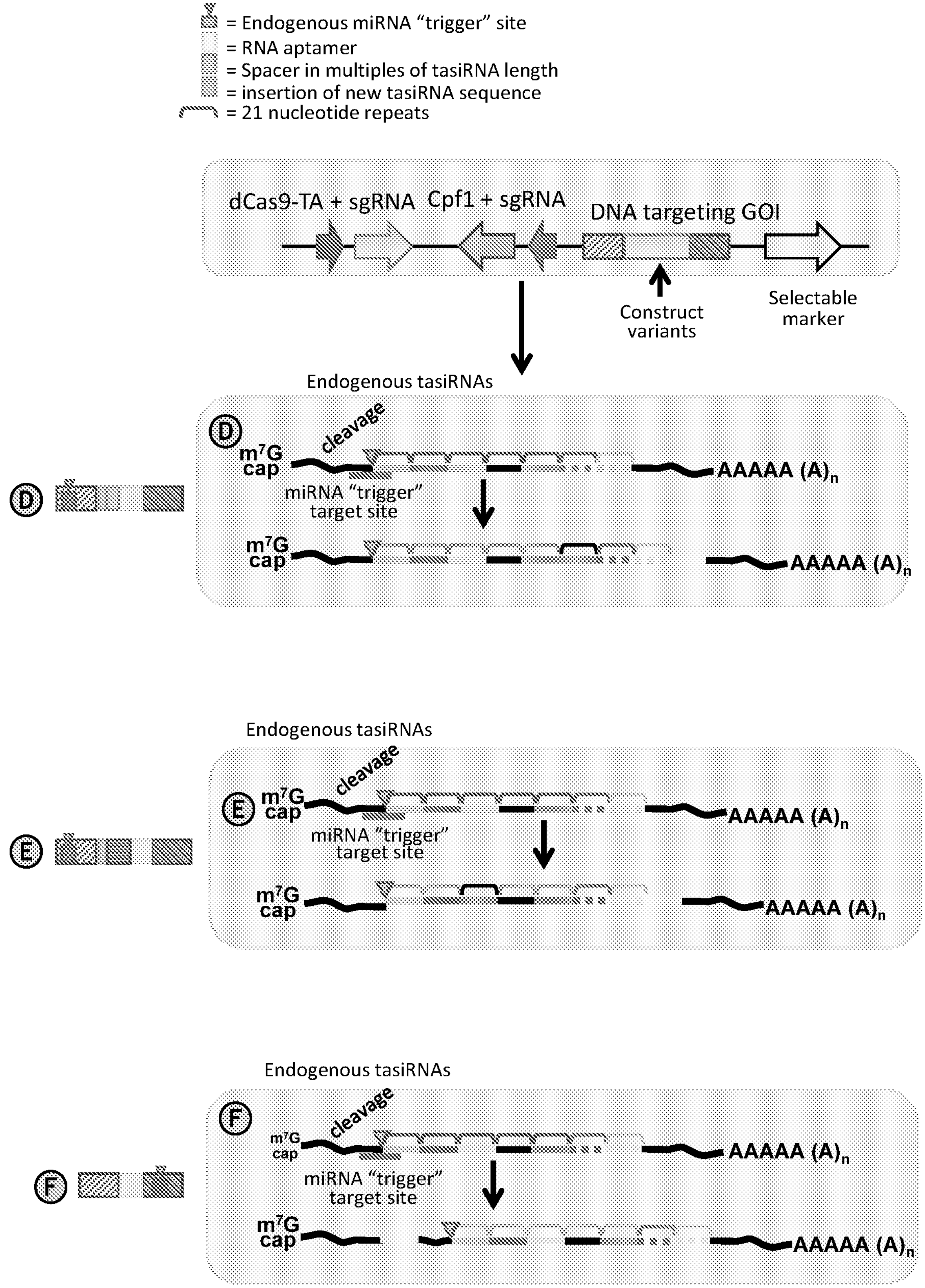
FIG. 7B schematically depicts a variant of the strategy depicted in FIG. 1, using a fluorescent RNA aptamer to create fusions with genes encoding tasi/phasiRNAs. Construct (D) and Panel (D) depicts an aspect wherein a new tasiRNA (pink 21 nucleotide repeat) is added downstream of the primary, endogenous tasiRNAs, in-phase, with the RNA aptamer added further 3'. Construct (E) and Panel (E) depicts an aspect wherein a 3' insertion or replacement of tasiRNAs (pink 21 nucleotide repeat) is performed in addition to adding an RNA aptamer. Construct (F) and Panel (F) depicts an aspect wherein an aptamer is added upstream of an miRNA target site.

The gene of interest may also be an RNA coding gene. Non-limiting examples of RNA coding genes may include genes encoding long non-translated RNAs (lntRNA), trans-acting siRNAs (tasiRNAs), antisense mRNAs, and the like (FIG. 7). When the gene of interest is an RNA coding gene, a reporter is preferably a fluorescent RNA aptamer, or other reporters that do not require translation to be expressed.

Figure 2A:
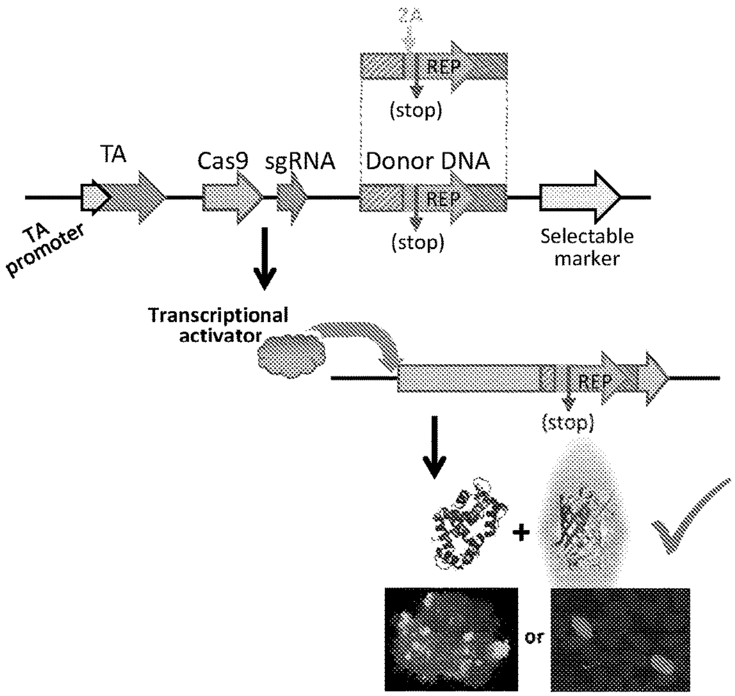
FIG. 2A schematically depict variations on the strategy depicted in FIG. 1, to identify products of homologous recombination without a permanent direct fusion of the reporter to a protein encoded by a gene of interest. In this aspect, the 2A self-cleaving peptide (2A) from the foot-and-mouth-disease virus (FMDV) is used. The 2A peptide is depicted fused at the N-terminus or the C terminus of the gene of interest, yielding a separate, unfused reporter protein. In the figure, an aspect is shown where epitope tags are added upstream of the 2A sequence.

Additionally, irrespective of the reporter used in a donor polynucleotide or the gene of interest, a donor polynucleotide may further comprise elements for expressing a reporter without a permanent fusion of the reporter with products of the gene of interest. For instance, as depicted in FIG. 2A, a reporter sequence encoded in frame at the C-terminus of an open reading frame of the gene of interest may be preceded by a skipping sequence that replaces the endogenous STOP codon of the gene of interest. After an accurate homologous recombination event, the gene of interest is expressed, a peptide encoded by the gene of interest and a separate reporter polypeptide are generated as a result of ribosomal skipping mediated by the skipping sequence. Non-limiting examples of skipping sequences include the 2A self-cleaving peptide of picornaviruses or 2A-like sequences (also called CHYSEL (cis-acting hydrolase element)) such as 2A-like sequences of iflaviridae, tetraviridae, dicistroviridae, and reoviridae.

Figure 2B:
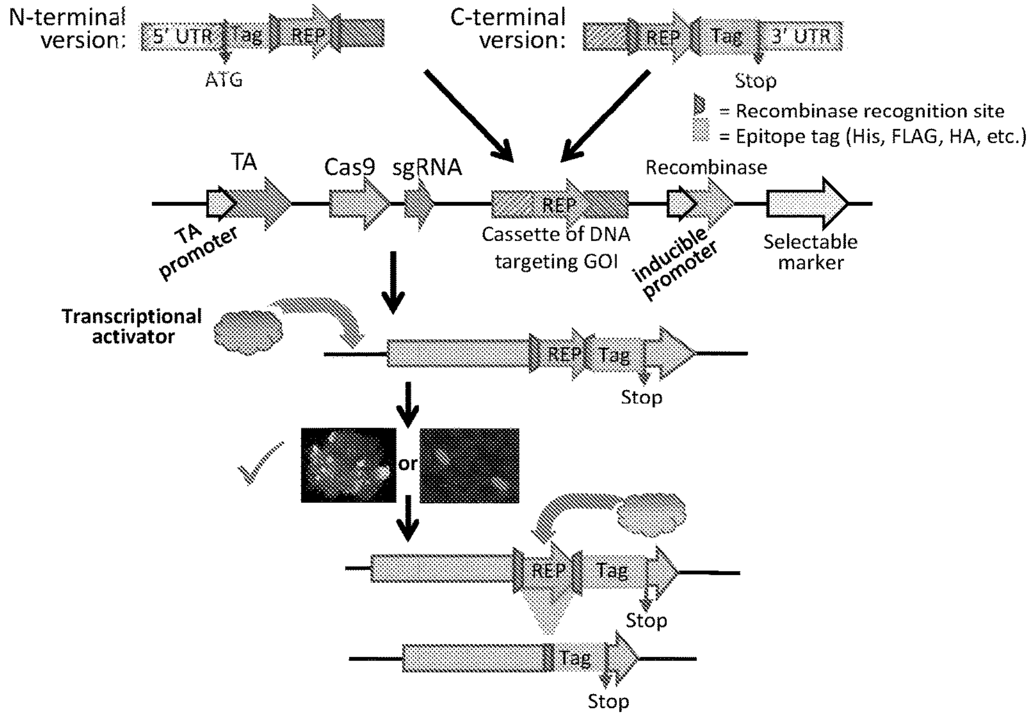
FIG. 2B schematically depict variations on the strategy depicted in FIG. 1, to identify products of homologous recombination without a permanent direct fusion of the reporter to a protein encoded by a gene of interest. In this aspect, an alternative strategy is shown, wherein the reporter sequence may be flanked with sites for a site-specific recombinase (inducible, encoded on the T-DNA backbone), to remove the reporter from the genome after identification of the correct product of HR, leaving behind the adjacent epitope tag and a short (~34 nt) recombinase site.

Alternatively, as depicted in FIG. 2B, a reporter sequence encoded in-frame with an open reading frame of the gene of interest may be flanked by recombinase recognition sites, and the homologous recombination composition may further comprise a recombinase. After an accurate homologous recombination event and expression of the gene of interest, a fusion protein comprising the reporter flanked by the recombinase recognition sites is expressed. The reporter may then be removed from the polypeptide of the gene of interest through the action of the recombinase. Non-limiting examples of a recombinase and recombinase recognition sites may include Cre recombinase and loxP recognition sites. Other strategies for expressing a reporter without a permanent fusion of the reporter with products of the gene of interest will be evident to an individual of skill in the art.

(iii) Homologous Regions

Typically, the reporter is flanked by upstream and downstream nucleic acid sequences homologous to the nucleic acid locus in a gene of interest. The upstream and downstream homologous sequences have substantial sequence identity to sequences located upstream and downstream, respectively, of the nucleic acid locus targeted by the targeting endonuclease. Because of these sequence similarities, the donor sequence may be integrated into (or exchanged with) a nucleic acid locus by homologous recombination. As used herein, the term "homologous" when used in reference to nucleic acid sequences, refers to sequences having at least about 75% sequence identity. Thus, the upstream and downstream sequences in the donor polynucleotide may have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with sequences upstream or downstream to the nucleic acid locus sequence. In specific aspects, the upstream and downstream sequences in the donor polynucleotide may have about 95% or 100% sequence identity with nucleic acid sequences upstream or downstream of the nucleic acid locus targeted by the targeting endonuclease.

As will be appreciated by those skilled in the art, the length of the donor polynucleotide may and does vary. For example, the construct sequence may vary in length from several base pairs to hundreds of base pairs to hundreds of thousands of base pairs. Each upstream or downstream sequence may range in length from about 20 base pairs to about 5000 base pairs. In some aspects, upstream and downstream sequences may comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 base pairs. In specific aspects, upstream and downstream sequences may range in length from about 50 to about 1500 base pairs.

(iv) Other Nucleic Acid Modifications

In addition to encoding a reporter, a donor polynucleotide may further encode other sequence modifications throughout the gene of interest at or near a nucleic acid locus. Non-limiting examples of sequences or sequence modifications that may be encoded in the donor polynucleotide include point mutations, partial sequence deletions, replacements, or additions, ribosomal skipping sequences, antibody epitopes and tags such as AcV5, AU1, AU5, E, ECS, E2, FLAG, Glu-Glu, HSV, KT3, myc, S, S1, T7, V5, VSV-G, and 6xHis and variants thereof, TAP tag, recombinase recognition sites, gene expression regulatory sequences, spacers, capture sequences, small RNA target sites, miRNA trigger sites, tasiRNA sequences. The following sections describe some aspects wherein a donor polynucleotide introduces a reporter, and further introduces other sequence modifications in the gene of interest. Other aspects will be readily apparent to individuals skilled in the art.

Promoter Replacement

Figure 4:
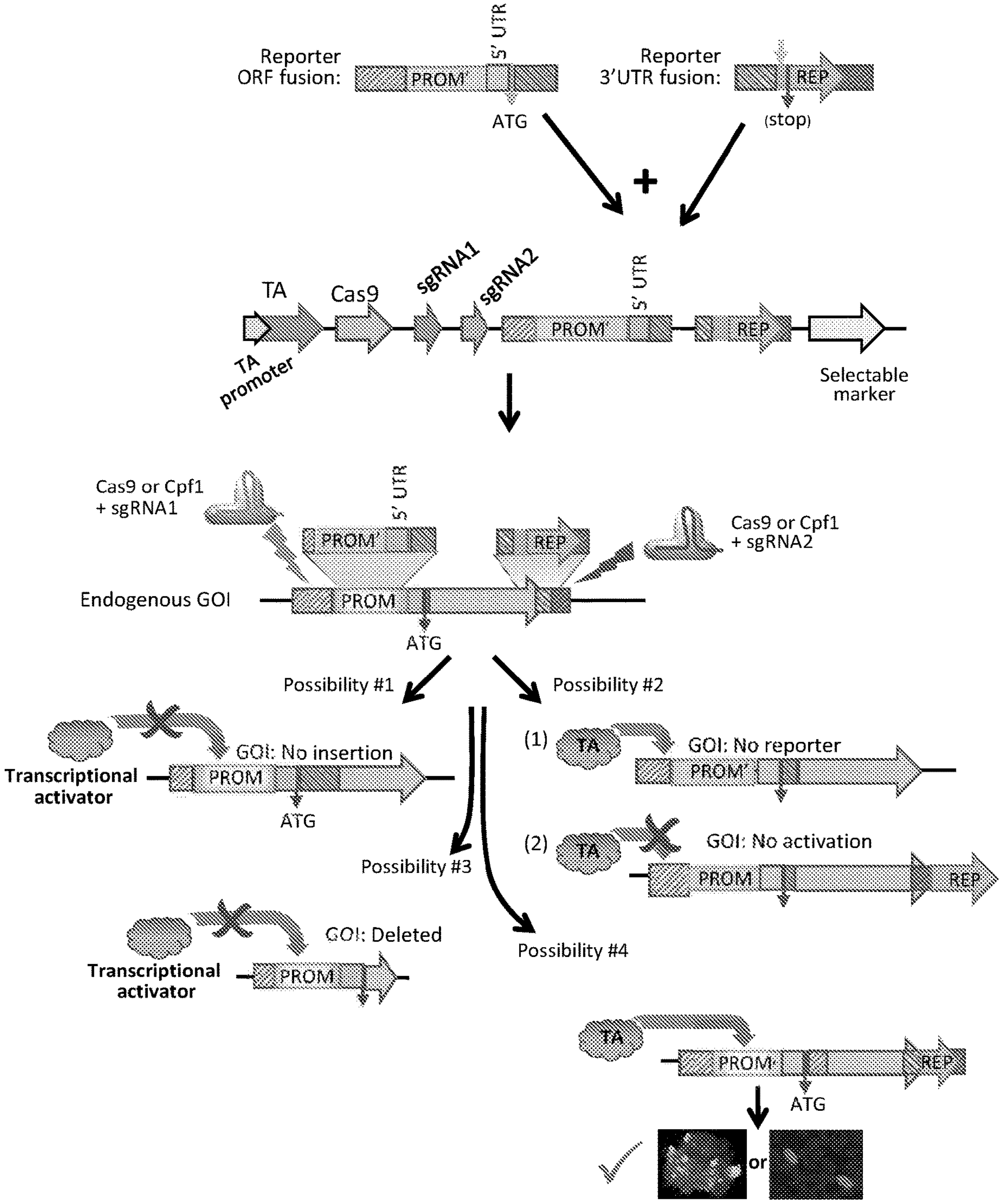
FIG. 4 schematically depicts variations on the strategy depicted in FIG. 1, to replace a promoter of an endogenous gene. The promoter (PROM) is replaced via homology at each end of the replacement cassette (Reporter ORF fusion) with the new promoter (PROM') using sgRNA1. A second sgRNA (sgRNA2) will target the 3' end of the target gene to trigger HR with a fragment to insert a 3' reporter (reporter 3' fusion), as shown in other figures. Four possible outcomes of the strategy are shown. Possibility #1: no HR, and no TA target site in the genome. Possibility #2: HR occurs as desired, but only at one of the two sites, yielding 2 possible fusions of reporter depicted as fusion (1) or fusion (2) but no activation in the presence of the TA. Possibility #3: The dual sgRNAs delete the GOI, and thus no HR has taken place. Possibility #4: The dual sgRNAs trigger two sites of HR, resulting in a TA-inducible GOI-reporter fusion with the promoter replaced as desired. Activation by a transcription activator specific for the new promoter expresses the reporter in the tissue in which screening is performed (for example, the seed or callus), and demonstrates that the new promoter plus the 3' end reporter both successfully inserted, as no other gene would be activated by the TA to express the reporter.

In some aspects, a donor polynucleotide may comprise more than one nucleic acid sequence to introduce more than one sequence or sequence modification at more than one locus in a gene of interest. For instance, when a donor polynucleotide further encodes a replacement of the endogenous promoter of a gene of interest, a reporter of the donor polynucleotide may be expressed, even when the homologous recombination is inaccurate or not at the intended target nucleic acid locus (FIG. 4). Therefore, to identify an accurate homologous recombination event wherein an endogenous promoter is replaced, a donor may comprise a first nucleic acid sequence targeting a first nucleic acid locus for replacing the endogenous promoter control sequences, and a second nucleic acid sequence at a second target nucleic acid locus for introducing a reporter. As shown in FIG. 4, the first nucleic acid sequence encodes the heterologous promoter flanked by regions of homology to the first locus, and the second nucleic acid sequence encodes a reporter flanked by regions homologous to a second nucleic acid locus in the gene of interest. Additionally, a programmable modification system of the composition may induce recombination at the first and second loci. For instance, the programmable nucleic acid modification system may encode two gRNAs, each specific for the first and second nucleic acid loci. In such an arrangement, a transcription activation system of the composition is specific to the heterologous promoter. Expression of the reporter after homologous recombination and transcription activation of the gene of interest indicates accurate homologous recombination events at the first and second loci in the gene of interest. Other strategies for using a donor polynucleotide comprising more than one nucleic acid sequence to introduce more than one sequence or sequence modification at more than one locus in a gene of interest may be envisioned by individuals skilled in the art.

Further Modifications of RNA Coding Genes

When the RNA coding gene encodes lncRNAs that are not further processed, such as COOLAIR, a reporter may be integrated at non-essential regions anywhere in the transcript (FIG. 7, Panel A). Additionally, a small RNA target site may further be introduced to "knock out" the lncRNA by inducing post-transcriptional control of the lncRNA (FIG. 7, Panel B). When the RNA coding gene encodes a miRNA precursor, one nucleotide polymorphism to several polymorphisms may be introduced at the 5' or 3' sequences of the precursor in addition to the RNA aptamer (FIG. 7, Panel C). When the RNA coding gene encodes a transcript processed into tasi/phasiRNAs, "in phase" insertions or even replacements of existing (but non-targeting) tasiRNAs or phasiRNAs may be generated (FIG. 7, Panels D-F). For instance, a new tasiRNA may be added downstream of the primary, endogenous tasiRNAs, in-phase with a fluorescent RNA aptamer added further 3' (FIG. 7, Panel D). Alternatively, a 3' insertion or replacement of tasiRNAs is performed, also adding a fluorescent RNA aptamer, but wherein an endogenous set of tasiRNAs is used as a spacer (FIG. 7, Panel E). Additionally, a fluorescent RNA aptamer may be added upstream of an miRNA target site, wherein the target site may be replaced with a target mimic to prevent slicing. Other modifications of RNA coding genes may be envisioned by individuals of skill in the art.

Modifying Intergenic Sequences between Two Genes of Interest

Figure 3A:
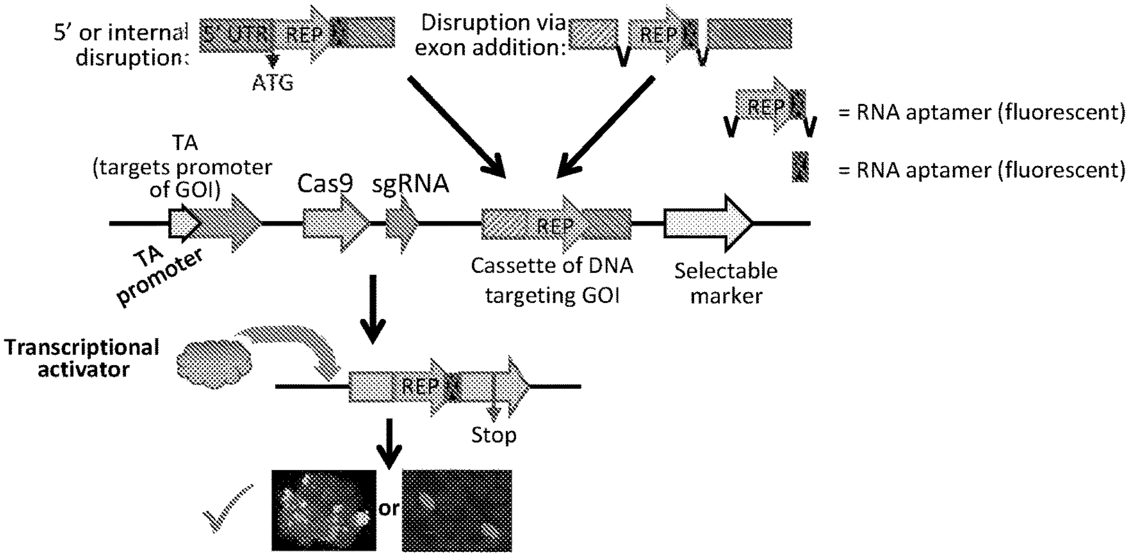
FIG. 3A schematically depict variations on the strategy depicted in FIG. 1 to accelerate targeted knockouts, without requiring large-scale genotyping. In this variation, a homologous recombination event introduces a reporter at the target nucleic acid locus, and disrupts the gene of interest by replacing the open reading frame, disrupting the start codon, and/or 5', 3', or internal coding exons, and providing a visual reporter that is induced by the TA in the tissue in which screening is performed (seed or callus).
Figure 3B:
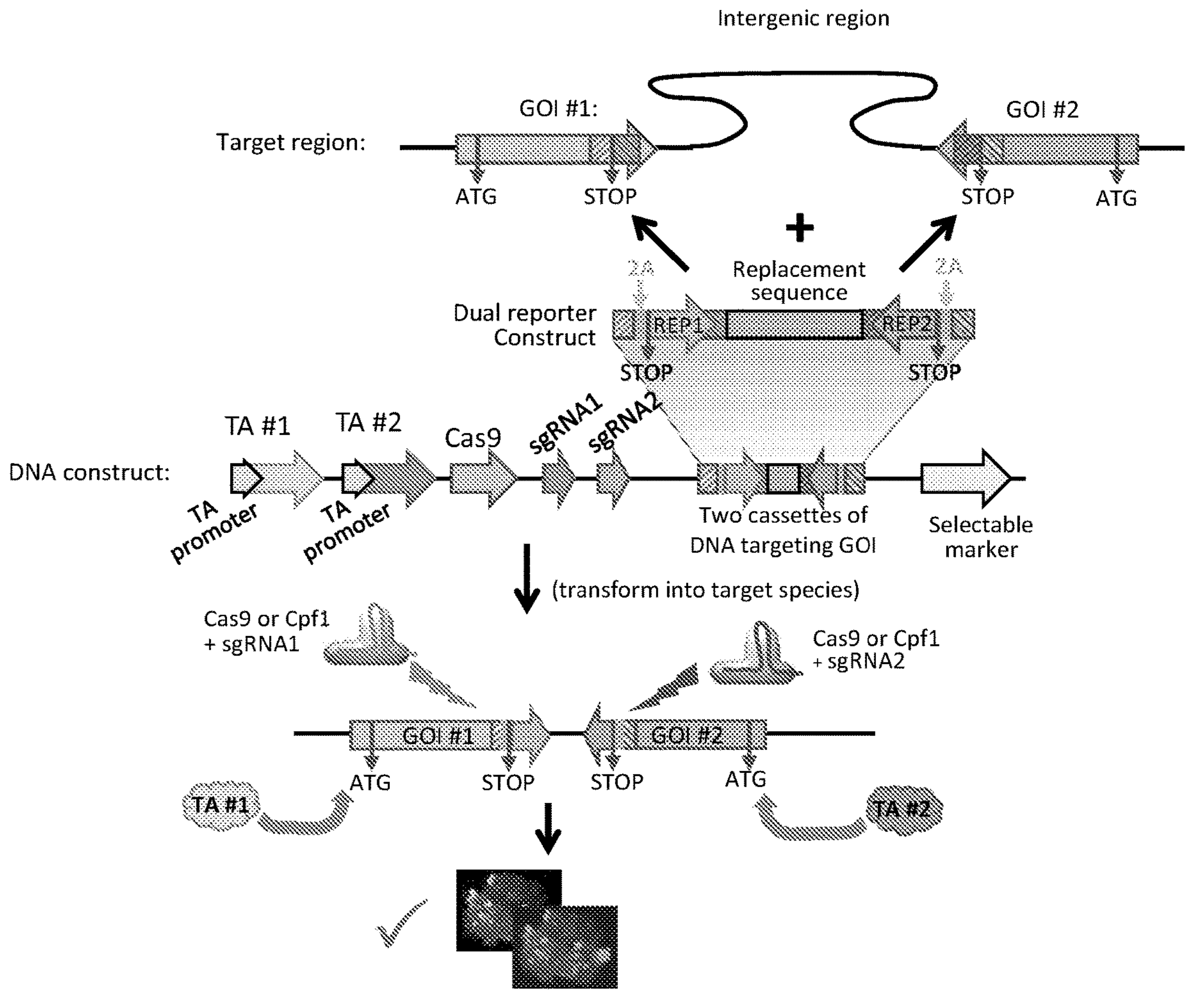
FIG. 3B schematically depict variations on the strategy depicted in FIG. 1 to accelerate targeted knockouts to introduce deletions between two genes of interest (FIG. 3B). Deletions or sequence replacements between two genes of interest may be achieved by targeting a pair of genes that are located some distance from one another, using HR and a dual reporter deletion-spanning replacement construct to introduce two reporters (green and red) into these genes, while also replacing the intervening sequence with a different nucleic acid sequence. Expression of both reporters after HR indicates replacement of the original nucleic acid sequence between the two genes of interest.

In some aspects, an intergenic nucleic acid sequence between two genes may be modified. For instance, an intergenic sequence may be deleted and/or replaced with a different sequence (FIG. 3B). The size of the intergenic sequence may range from 0 base pairs to 100s of base pairs, 1000s of base pairs or longer. Further, the intergenic region may comprise coding sequences, regulatory sequences, or any other kind of sequence. As shown in FIG. 3B, a pair of genes are targeted using a donor polynucleotide encoding (1) a first replacement polynucleotide comprising a first reporter flanked by regions of homology to a first nucleic acid locus in a first gene of interest, and (2) a second replacement polynucleotide comprising a second reporter flanked by regions of homology to a second nucleic acid locus in a second gene of interest. The donor polynucleotide further comprises an intergenic construct flanked by the first replacement polynucleotide and the second replacement polynucleotide. The size of the intergenic construct may range from 0 base pairs to 100s of base pairs, 1000s of base pairs or longer. In such an arrangement, a programmable modification system of the composition may induce recombination at the first and second loci in the first and second genes of interest, respectively. For instance, a programmable modification system may encode two gRNAs, each specific for the first and second nucleic acid loci, thereby inducing homologous recombination at the two loci. Accurate recombination at the first and second loci results in the replacement of the intergenic sequence with the intergenic construct. Additionally, in such a system, a homologous recombination composition further comprises a first transcription activation system specific for inducing expression of the first gene of interest, and a second transcription activation system specific for inducing expression of the second gene of interest. Expression of the first and second reporters after homologous recombination and transcription activation of the genes of interest indicates accurate homologous recombination events at the first and second loci in the genes of interest and replacement of the intergenic region with the intergenic construct.

Individuals skilled in the art may envision various useful configurations of useful replacement intergenic constructs. For instance, an intergenic sequence may be deleted. Alternatively, an intergenic sequence may be replaced with a shorter or longer version of the intergenic sequence, or may introduce heterologous nucleic acid sequences.

(b) Transcription Activation System

The homologous recombination composition comprises a transcription activation system specific for inducing expression of a gene of interest. The transcription activation system comprises a transcription activator (or transcription complex recruiting domain). A transcription activator is a protein that increases transcription of a gene of interest by directly or indirectly interacting with the promoter of the gene of interest.

As a homologous recombination composition of the disclosure may further introduce sequences or sequence modifications throughout the gene of interest in addition to introducing a reporter at a target locus, it will be recognized that the transcription activator of the disclosure induces expression of the modified gene of interest resulting from any intended accurate recombination events. For instance, when the open reading frame of a gene of interest is completely replaced by the coding sequence of a reporter, a transcription activation system induces expression of the reporter coding sequence. Similarly, when the promoter of the gene of interest is replaced with a heterologous promoter, a transcription activation system specifically induces expression of the gene of interest by directly or indirectly interacting with the heterologous promoter.

A transcription activator may be a wild type transcription activator naturally specific for inducing transcription of a gene of interest, or modified versions of a wild type transcription activator naturally specific for inducing transcription of a gene of interest. For instance, the transcription activator may be a wild type TALE effector naturally specific for inducing transcription of a gene of interest. Alternatively, a transcription activator may be a synthetic or artificial programmable transcription activator. Programmable transcription activators are well known in the art. Programmable transcription activators generally comprise wild-type or naturally-occurring nucleic acid-binding and/or transcription activation domains, modified versions of naturally-occurring nucleic acid-binding and/or transcription activation domains, synthetic or artificial nucleic acid-binding and/or transcription activation domains, or combinations thereof. In general, engineered transcription activators comprise a programmable nucleic acid-binding domain and a transcription activation domain.

A transcriptional activation domain interacts with transcriptional control elements and/or transcriptional regulatory proteins (i.e., transcription factors, RNA polymerases, etc.) to increase and/or activate transcription of a gene. Suitable transcriptional activation domains include, without limit, herpes simplex virus VP16 domain, VP64 (which is a tetrameric derivative of VP16), VP160 (i.e., 10xVP16), p65 activation domain from NFκB, p53 activation domains 1 and 2, heat-shock factor 1 (HSF1) activation domain, MyoD1 activation domain, GCN4 peptide, 10xGCN4, viral R transactivator (Rta), VPR (a fusion of VP64-p65-Rta), p53 activation domains 1 and 2, CREB (cAMP response element binding protein) activation domains, E2A activation domains, activation domains from human heat-shock factor 1 (HSF1), NFAT (nuclear factor of activated T-cells) activation domains, a histone acetyltransferase, activation domains from the *Arabidopsis thaliana* MYB46, HAM1, HAM2, MYB112, WRKY11, ERF6, or a combination thereof. Engineered transcription activation systems may comprise one transcription activation domain, two transcription activation domains, three transcription activation domains, or more than three transcription activation domains.

Programmable nucleic acid-binding domains may be a programmable endonuclease (i.e., CRISPR/CAS nuclease, Ago nuclease, or meganuclease) modified to lack all nuclease activity. Alternatively, a programmable nucleic acid-binding domain may be a programmable nucleic acid-binding protein such as, e.g., a zinc finger protein or a TALE. For instance, a programmable nucleic acid-binding domain may be a catalytically inactive CRISPR/Cas nuclease in which the nuclease activity was eliminated by mutation and/or deletion. For example, the catalytically inactive CRISPR/Cas protein may be a catalytically inactive (dead) Cas9 (dCas9) in which the RuvC-like domain comprises a D10A, E762A, and/or D986A mutation and the HNH-like domain comprises a H840A (or H839A), N854A and/or N863A mutation. Alternatively, the catalytically inactive CRISPR/Cas protein may be a catalytically inactive (dead) Cpf1 protein comprising comparable mutations in the nuclease domain. A programmable nucleic acid-binding domain may also be a catalytically inactive Ago endonuclease in which nuclease activity was eliminated by mutation and/or deletion. Alternatively, a programmable nucleic acid-binding domain may be a catalytically inactive meganuclease in which nuclease activity was eliminated by mutation and/or deletion, e.g., the catalytically inactive meganuclease may comprise a C-terminal truncation. A programmable nucleic acid-binding domain may also be a transcription activator-like effectors (TALEs) nucleic acid-binding protein.

Transcriptional activation domains may be genetically fused to the nucleic acid binding protein or bound via noncovalent protein-protein, protein-RNA, or protein-DNA interactions. As described above in Section (I)(a)(A)(vii) for programmable nucleic acid modification systems, transcription activation systems may also comprise at least one nuclear localization signal, cell-penetrating domain, reporter domain, and/or detectable label.

(c) Optional Components

A composition may further comprise additional components to facilitate processes such as a nucleic acid modification. For instance, a composition may further comprise a programmable nucleic acid-modification protein. A programmable nucleic acid-modification protein may be a fusion protein comprising a non-nuclease domain and a programmable nucleic acid-binding domain. Suitable programmable nucleic acid-binding domains are described above in Section (I)(a)(A). Examples of suitable non-nuclease domains include epigenetic modification domains. In general, epigenetic modification domains alter gene expression by modifying the histone structure and/or nucleic acid structure. Suitable epigenetic modification domains include, without limit, histone acetyltransferase domains, histone deacetylase domains, histone methyltransferase domains, histone demethylase domains, DNA methyltransferase domains, DNA demethylase domains, transposase domains, integrase domains, recombinase domains, resolvase domains, invertase domains, protease domains, DNA methyltransferase domains, DNA hydroxylmethylase domains, DNA demethylase domains, histone acetylase domains, repressor domains, activator domains, cellular uptake activity associated domains, antibody presentation domains, recruiter of histone modifying enzymes, inhibitor of histone modifying enzymes, histone kinase domains, histone phosphatase domains, histone ribosylase domains, histone deribosylase domains, histone ubiquitinase domains, histone deubiquitinase domains, histone biotinase domains, and histone tail protease domains.

II. Nucleic Acids

A further aspect of the present disclosure provides a system of one or more nucleic acid constructs encoding one or more components of the homologous recombination composition described above in Section I. The system may comprise one or more nucleic acid expression constructs encoding a programmable nucleic acid modification system, one or more expression constructs encoding a transcription activation system specific for inducing expression of a gene of interest, and combinations thereof. A system further comprises a nucleic acid construct encoding a donor polynucleotide of the homologous recombination system.

Compositions may be expressed or encoded by single nucleic acid constructs or multiple nucleic acid constructs. The nucleic acid constructs may be DNA or RNA, linear or circular, single-stranded or double-stranded, or any combination thereof. The nucleic acid constructs may be codon optimized for efficient translation into protein in the cell of interest. Codon optimization programs are available as freeware or from commercial sources.

One or more of the nucleic acid constructs may be RNA. The RNA may be enzymatically synthesized in vitro. For this, DNA encoding the one or more nucleic acids may be operably linked to a promoter sequence that is recognized by a phage RNA polymerase for in vitro RNA synthesis. For example, the promoter sequence may be a T7, T3, or SP6 promoter sequence or a variation of a T7, T3, or SP6 promoter sequence. The DNA encoding the one or more nucleic acids may be part of a vector, as detailed below. In such aspects, the in vitro-transcribed RNA may be purified, capped, and/or polyadenylated. Alternatively, the RNA may be part of a self-replicating RNA (Yoshioka et al., Cell Stem Cell, 2013, 13:246-254). The self-replicating RNA may be derived from a noninfectious, self-replicating Venezuelan equine encephalitis (VEE) virus RNA replicon, which is a positive-sense, single-stranded RNA that is capable of self-replicating for a limited number of cell divisions, and which may be modified to code proteins of interest (Yoshioka et al., Cell Stem Cell, 2013, 13:246-254).

One or more nucleic acid constructs encoding the composition may also be DNA. When one or more of the nucleic acid constructs are DNA, each of the programmable nucleic acid modification system and the transcription activation system may be encoded by one or more nucleic acid expression constructs. The expression constructs comprise DNA coding sequences operably linked to at least one promoter control sequence for expression in a cell of interest. Preferably, promoter control sequences control expression in screenable tissue or cells.

Promoter control sequences may control expression of the programmable nucleic acid modification system and/or the transcription activation system in bacterial (e.g., *E. coli*) cells or eukaryotic (e.g., yeast, insect, mammalian, or plant) cells. Suitable bacterial promoters include, without limit, T7 promoters, lac operon promoters, trp promoters, tac promoters (which are hybrids of trp and lac promoters), variations of any of the foregoing, and combinations of any of the foregoing. Non-limiting examples of suitable eukaryotic promoters include constitutive, regulated, or cell- or tissue-specific promoters. Suitable eukaryotic constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable eukaryotic regulated promoter control sequences include, without limit, those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter.

Promoters may also be plant-specific promoters, or promoters that may be used in plants. A wide variety of plant promoters are known to those of ordinary skill in the art, as are other regulatory elements that may be used alone or in combination with promoters. Preferably, promoter control sequences control expression in cassava such as promoters disclosed in Wilson et al., 2017, The New Phytologoist, 213(4):1632-1641, the disclosure of which is incorporated herein in its entirety.

Promoters may be divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters. Suitable plant-specific constitutive promoter control sequences include, but are not limited to, a CaMV35S promoter, CaMV 19S, GOS2, *Arabidopsis* At6669 promoter, Rice cyclophilin, Maize H3 histone, Synthetic Super MAS, an opine promoter, a plant ubiquitin (Ubi) promoter, an actin 1 (Act-1) promoter, pEMU, Cestrum yellow leaf curling virus promoter (CYMLV promoter), and an alcohol dehydrogenase 1 (Adh-1) promoter. Other constitutive promoters include those in U.S. Pat. Nos. 5,659,026; 5,608,149; 5,608,144; 5,604,121; 5,569,597; 5,466,785; 5,399,680; 5,268,463; and 5,608,142.

Regulated plant promoters respond to various forms of environmental stresses, or other stimuli, including, for example, mechanical shock, heat, cold, flooding, drought, salt, anoxia, pathogens such as bacteria, fungi, and viruses, and nutritional deprivation, including deprivation during times of flowering and/or fruiting, and other forms of plant stress. For example, the promoter may be a promoter which is induced by one or more, but not limited to one of the following: abiotic stresses such as wounding, cold, desiccation, ultraviolet-B, heat shock or other heat stress, drought stress or water stress. The promoter may further be one induced by biotic stresses including pathogen stress, such as stress induced by a virus or fungi, stresses induced as part of the plant defense pathway or by other environmental signals, such as light, carbon dioxide, hormones or other signaling molecules such as auxin, hydrogen peroxide and salicylic acid, sugars and gibberellin or abscisic acid and ethylene. Suitable regulated plant promoter control sequences include, but are not limited to, salt-inducible promoters such as RD29A; drought-inducible promoters such as maize rab17 gene promoter, maize rab28 gene promoter, and maize Ivr2 gene promoter; heat-inducible promoters such as heat tomato hsp80-promoter from tomato.

Tissue-specific promoters may include, but are not limited to, fiber-specific, green tissue-specific, root-specific, stem-specific, flower-specific, callus-specific, pollen-specific, egg-specific, and seed coat-specific. Suitable tissue-specific plant promoter control sequences include, but are not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed-specific genes (Simon et al., Plant Mol. Biol. 5. 191, 1985; Scofield et al., J. Biol. Chem. 262: 12202, 1987; Baszczynski et al., Plant Mol. Biol. 14: 633, 1990), Brazil Nut albumin (Pearson et al., Plant Mol. Biol. 18: 235-245, 1992), legumin (Ellis et al., Plant Mol. Biol. 10: 203-214, 1988), Glutelin (rice) (Takaiwa et al., Mol. Gen. Genet. 208: 15-22, 1986; Takaiwa et al., FEBS Letts. 221: 43-47, 1987), Zein (Matzke et al., Plant Mol Biol, 143: 323-32, 1990), napA (Stalberg et al., Planta 199: 515-519, 1996), Wheat SPA (Albanietal, Plant Cell, 9: 171-184, 1997), sunflower oleosin (Cummins et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMBO3:1409-15, 1984), Barley ItrI promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al., Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo-specific promoters [e.g., rice OSH1 (Sato et al., Proc. Natl. Acad. Sci. USA, 93: 8117-8122), KNOX (Postma-Haarsma et al., Plant Mol. Biol. 39:257-71, 1999), rice oleosin (Wu et al., J. Biochem., 123:386, 1998)], and flower-specific promoters [e.g., AtPRP4, chalene synthase (chsA) (Van der Meer et al., Plant Mol. Biol. 15, 95-109, 1990), LAT52 (Twell et al., Mol. Gen Genet. 217:240-245; 1989), apetala-3].

Promoter control sequences may also be promoter control sequences of the gene of interest, such that the expression pattern of the one or more nucleic acid constructs matches the expression pattern of the gene of interest. The promoter sequence may be wild type or it may be modified for more efficient or efficacious expression. The DNA coding sequence also may be linked to a polyadenylation signal (e.g., SV40 polyA signal, bovine growth hormone (BGH) polyA signal, etc.) and/or at least one transcriptional termination sequence. In some situations, the complex or fusion protein may be purified from the bacterial or eukaryotic cells.

Nucleic acids encoding one or more components of a homologous recombination system and/or transcription activation system may be present in a vector. Suitable vectors include plasmid vectors, viral vectors, and self-replicating RNA (Yoshioka et al., Cell Stem Cell, 2013, 13:246-254). For instance, the nucleic acid encoding one or more components of a homologous recombination system and/or transcription activation system may be present in a plasmid vector. Non-limiting examples of suitable plasmid vectors include pUC, pBR322, pET, pBluescript, and variants thereof. Alternatively, the nucleic acid encoding one or more components of a homologous recombination system and/or transcription activation system may be part of a viral vector (e.g., lentiviral vectors, adeno-associated viral vectors, adenoviral vectors, and so forth).

The plasmid or viral vector may comprise additional expression control sequences (e.g., enhancer sequences, Kozak sequences, polyadenylation sequences, transcriptional termination sequences, etc.), selectable reporter sequences (e.g., antibiotic resistance genes), origins of replication, T-DNA border sequences, and the like. The plasmid or viral vector may further comprise RNA processing elements such as glycine tRNAs, or Csy4 recognition sites. Such RNA processing elements may, for instance, intersperse polynucleotide sequences encoding multiple gRNAs under the control of a single promoter to produce the multiple gRNAs from a transcript encoding the multiple gRNAs. When a cys4 recognition cite is used, a vector may further comprise sequences for expression of Csy4 RNAse to process the gRNA transcript. Additional information about vectors and use thereof may be found in "Current Protocols in Molecular Biology", Ausubel et al., John Wiley & Sons, New York, 2003, or "Molecular Cloning: A Laboratory Manual", Sambrook & Russell, Cold Spring Harbor Press, Cold Spring Harbor, NY, 3rd edition, 2001.

Below, nucleic acid constructs encoding each component of the homologous recombination system will be described. As explained above, the nucleic acid constructs may be encoded by a single nucleic acid construct or multiple nucleic acid constructs.

(a) Modification System Constructs

As described above, programmable nucleic acid modification systems generally comprise a programmable, sequence-specific nucleic acid-binding domain, and a modification domain. As such, the programmable, sequence-specific nucleic acid-binding domain and the modification domain may be encoded by one or more nucleic acid expression constructs. For instance, when the sequence-specific nucleic acid-binding domain and the modification domain are a single protein, a single nucleic acid construct may encode both functions of the modification system. Alternatively, the sequence-specific nucleic acid-binding domain may be encoded by a first construct, and the modification domain may be encoded by a second construct. Additionally, when nucleic acid binding is mediated by one or more guide RNAs, the guide RNAs may further be encoded by a third nucleic acid expression construct.

When the programmable nucleic acid modification system is encoded by more than one nucleic acid DNA construct, each construct may be operably linked to a promoter, wherein the promoter control sequences for expression in the cell of interest are the same. Alternatively, each expression construct may be operably linked to a different promoter control sequence for finer control of expression in a cell of interest.

When the programmable nucleic acid modification system is encoded by more than one nucleic acid DNA construct, the constructs may be part of one or more vectors. Not being bound by a theory, the ability to simultaneously deliver components of the programmable nucleic acid modification system through a single vector enables application to any cell type of interest, without the need to first generate cell lines that express various components of the programmable nucleic acid modification system.

(b) Donor Polynucleotide Constructs

A donor polynucleotide may be an RNA polynucleotide, an RNA polynucleotide encoded by a DNA construct, or a DNA polynucleotide. An RNA polynucleotide and RNA polynucleotide encoded by a DNA construct may be as described above. When a donor polynucleotide is a DNA polynucleotide, the donor polynucleotide may be a DNA plasmid, a bacterial artificial chromosome (BAC), a yeast artificial chromosome (YAC), a viral vector, a linear piece of DNA, or a PCR fragment. A donor polynucleotide may also be encoded on a nucleic acid construct expressing a programmable nucleic acid modification system and/or a transcription activation system.

(c) Transcription Activation System

As described above, the transcription activation system may comprise a wild type or a modified version of a transcription activator naturally specific for inducing transcription of a gene of interest. A transcription activator may also be a synthetic or artificial programmable transcription activator comprising a nucleic acid-binding and a transcription activation domain. As such, the programmable, sequence-specific nucleic acid-binding domain, and the transcription activation domain may be encoded by one or more nucleic acid constructs. For instance, when the sequence-specific nucleic acid-binding domain and the transcription activation domain are a single protein, a single nucleic acid construct may encode both functions of the transcription activation system. Alternatively, the sequence-specific nucleic acid-binding domain may be encoded by a first construct, and the transcription activation domain may be encoded by a second construct. Additionally, when nucleic acid binding is mediated by a guide RNA, the guide RNA may further be encoded by a third nucleic acid construct.

When the transcription activation system is encoded by more than one nucleic acid DNA construct, each construct may be operably linked to a promoter, wherein the promoter control sequence for expression in the cell of interest is the same. Alternatively, each construct may be operably linked to different promoter control sequences for finer control of expression in the cell of interest.

When the transcription activation system is encoded by more than one nucleic acid DNA construct, the constructs may be part of one or more vectors. Not being bound by a theory, the ability to simultaneously deliver components of the transcription activation system through a single vector enables application to any cell type of interest, without the need to first generate cell lines that express various components of the transcription activation system.

At least one of the constructs expressing a transcription activation system is preferably operably linked to a tissue-specific promoter, more preferably a promoter expressed in easily screenable tissue. For instance, if the homologous recombination is in a plant cell, the easily screenable tissue may include callus tissue or seed coat tissue.

III. Cells

In another aspect, the present disclosure provides a cell comprising a homologous recombination composition. A homologous recombination composition may be as described in Section I above. One or more components of the homologous recombination composition may be encoded by one or more nucleic acid constructs of a system of vectors. The system of vectors may be as described in Section II above.

A variety of cells are suitable for use in the methods disclosed herein. The cell may be a prokaryotic cell. Alternatively, the cell is a eukaryotic cell. For example, the cell may be a prokaryotic cell, a human mammalian cell, a non-human mammalian cell, a non-mammalian vertebrate cell, an invertebrate cell, an insect cell, a plant cell, a yeast cell, or a single cell eukaryotic organism. The cell may also be a one-cell embryo. For example, a non-human mammalian embryo including rat, hamster, rodent, rabbit, feline, canine, ovine, porcine, bovine, equine, plant, and primate embryos. The cell may also be a stem cell such as embryonic stem cells, ES-like stem cells, fetal stem cells, adult stem cells, and the like. The cell may be in vitro, ex vivo, or in vivo (i.e., within an organism or within a tissue of an organism).

Non-limiting examples of suitable mammalian cells or cell lines include human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells; Chinese hamster ovary (CHO) cells; baby hamster kidney (BHK) cells; mouse myeloma NSO cells; mouse embryonic fibroblast 3T3 cells (NIH3T3); mouse B lymphoma A20 cells; mouse melanoma B16 cells; mouse myoblast C2C12 cells; mouse myeloma SP2/0 cells; mouse embryonic mesenchymal C3H-10T½ cells; mouse carcinoma CT26 cells; mouse prostate DuCuP cells; mouse breast EMT6 cells; mouse hepatoma Nepal c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; Afrimay green monkey kidney (VERO-76) cells. An extensive list of mammalian cell lines may be found in the Amerimay Type Culture Collection catalog (ATCC, Manassas, VA).

The cell may be a plant cell. Non-limiting examples of plant cells include parenchyma cells, sclerenchyma cells, collenchyma cells, xylem cells, and phloem cells. Preferably, the plant cell is a cell that allows for easy identification of an accurate homologous recombination event. Non-limiting examples of plant tissues that allow for easy identification of an accurate homologous recombination event include ptotoplast cells, cotyledon cells, callus cells, embryos, endosperm cells, and cells of the seed coat.

IV. Methods

A further aspect of the present disclosure provides a method of generating one or more accurate homologous recombination events. The homologous recombination events may be generated in vitro (see, e.g., Liu et al., 2015, mBio vol/6, no. 6, e01714-15). Alternatively, the homologous recombination events may be generated in a cell at one or more nucleic acid loci in nucleic acid sequences of a cell. The cell may be ex vivo or in vivo. The nucleic acid sequences may be chromosomal sequences, organellar chromosomal sequences, or extrachromosomal sequences.

When homologous recombination is generated in a cell, the method comprises providing one or more homologous recombination compositions, and introducing into the cell the one or more homologous recombination compositions. The method further comprises identifying one or more accurate homologous recombination events by identifying one or more cells expressing a reporter. The one or more homologous recombination compositions may be as described in Section I; a system of nucleic acid constructs encoding one or more components of the homologous recombination compositions may be as described in Section II; and the cells may be as described in Section III.

The one or more accurate homologous recombination events may be achieved in a single gene of interest or more. For instance, the accurate homologous recombination event may be achieved in 100 or more unique genes of interest, in 1000 or more unique genes, or in 20,000 or more unique genes. The accurate homologous recombination events may also be achieved in the entire genome. Additionally, more than one accurate homologous recombination event may be generated in a single gene of interest.

(a) Introduction into the Cell

The method comprises introducing the one or more homologous recombination compositions into a cell of interest. The one or more homologous recombination compositions may be introduced into the cell as a purified isolated composition, purified isolated components of a composition, as one or more nucleic acids encoding the one or more homologous recombination compositions, or components of the homologous recombination composition, and combinations thereof.

Components of the one or more homologous recombination compositions may be separately introduced into a cell. For example, a programmable nucleic acid modification system, a donor nucleic acid construct, and a transcription activation system of a composition may be introduced into a cell sequentially. Alternatively, components of a composition may be introduced simultaneously. Similarly, the one or more homologous recombination compositions (or nucleic acids encoding the one or more homologous recombination compositions) may be introduced into a cell sequentially or simultaneously.

The one or more homologous recombination compositions described above may be introduced into the cell by a variety of means. Suitable delivery means include microinjection, electroporation, sonoporation, biolistics, calcium phosphate-mediated transfection, cationic transfection, liposomes and other lipids, dendrimer transfection, heat shock transfection, nucleofection transfection, gene gun delivery, dip transformation, supercharged proteins, cell-penetrating peptides, implantable devices, magnetofection, lipofection, impalefection, optical transfection, proprietary agent-enhanced uptake of nucleic acids, *Agrobacterium tumefaciens* mediated foreign gene transformation, proprietary agent-enhanced uptake of nucleic acids, and delivery via liposomes, immunoliposomes, virosomes, or artificial virions. In a specific aspect, the targeting endonuclease molecule(s) and polynucleotides(s) are introduced into the cell by nucleofection.

(b) Culturing a Cell

The method further comprises maintaining the cell under appropriate conditions such that the double-stranded break introduced by the targeting endonuclease may be repaired by (i) a non-homologous end-joining repair process such that a nucleic acid locus sequence is modified by a deletion, insertion and/or substitution of at least one base pair or, optionally, (ii) a homology-directed repair process such that the nucleic acid locus sequence is exchanged with the donor sequence of the donor polynucleotide such that the nucleic acid locus sequence is modified. In aspects in which nucleic acid(s) encoding the targeting endonuclease(s) are introduced into the cell, the method comprises maintaining the cell under appropriate conditions such that the cell expresses the targeting endonuclease(s). When the cell is in tissue ex vivo, or in vivo within an organism or within a tissue of an organism, the tissue and/or organism may also be maintained under appropriate conditions for homologous recombination.

In general, the cell is maintained under conditions appropriate for cell growth and/or maintenance. Suitable cell culture conditions are well known in the art and are described, for example, in Santiago et al. (2008) PNAS 105:5809-5814; Moehle et al. (2007) PNAS 104:3055-3060; Urnov et al. (2005) Nature 435:646-651; and Lombardo et al. (2007) Nat. Biotechnology 25:1298-1306; Taylor et al., (2012) Tropical Plant Biology 5: 127-139. Those of skill in the art appreciate that methods for culturing cells are known in the art and may and will vary depending on the cell type. Routine optimization may be used, in all cases, to determine the best techniques for a particular cell type.

During this step of the process, the targeting endonuclease(s) recognizes, binds, and creates a double-stranded break(s) at the targeted cleavage site(s) in the nucleic acid locus sequence. In some aspects, repair of the double-stranded break(s) by NHEJ leads to a deletion, insertion, and/or substitution of at least one base pair in targeted nucleic acid locus sequence(s) such that the targeted nucleic acid locus sequence is inactivated and the cell produces less of the protein of interest. In aspects in which a donor polynucleotide is present, repair of the double-stranded break by a homology-directed process leads to integration of the donor sequence in the donor polynucleotide into the targeted nucleic acid locus such that the cell produces an exogenous protein or more of the protein of interest.

(c) Identification of an Accurate Homologous Recombination Event

The method further comprises identifying an accurate homologous recombination event. The accurate homologous recombination event may be identified by identifying a cell expressing the reporter. Methods of identifying a cell expressing a reporter may and will vary depending on the reporter, the cell, the tissue or the organism comprising the cell, among others. For instance, if a reporter is a visual reporter, a cell expressing a reporter may be identified by observing a visual signal in the cell. If a reporter is a selectable reporter such as antibiotic resistance, a cell expressing a reporter may be identified by selecting an antibiotic resistant cell.

Upon confirmation that an accurate homologous recombination event has occurred, single cell clones may be isolated. Additionally, cells comprising one accurate homologous recombination event may undergo one or more additional rounds of targeted modification to modify additional nucleic acid loci sequences.

V. Library of Compositions

A further aspect of the present disclosure provides a library of homologous recombination compositions comprising two or more homologous recombination compositions. As homologous recombination compositions and systems described herein may be used to efficiently and cost-effectively target numerous nucleic acid loci, the homologous recombination compositions may comprise a genome wide library of compositions. Such a library may provide for determining the function of genes, cellular pathways genes are involved in, and how any alteration in gene expression may result in a particular biological process. Using the library of homologous recombination compositions would accelerate the identification of accurately targeted homologous recombination events, without requiring large-scale genotyping. Homologous recombination compositions may be as described in Section I. Preferably, each homologous recombination composition is encoded by a system of one or more nucleic acid constructs encoding the homologous recombination composition. Systems of nucleic acid constructs encoding one or more components of the homologous recombination composition may be as described in Section II.

Figure 5:
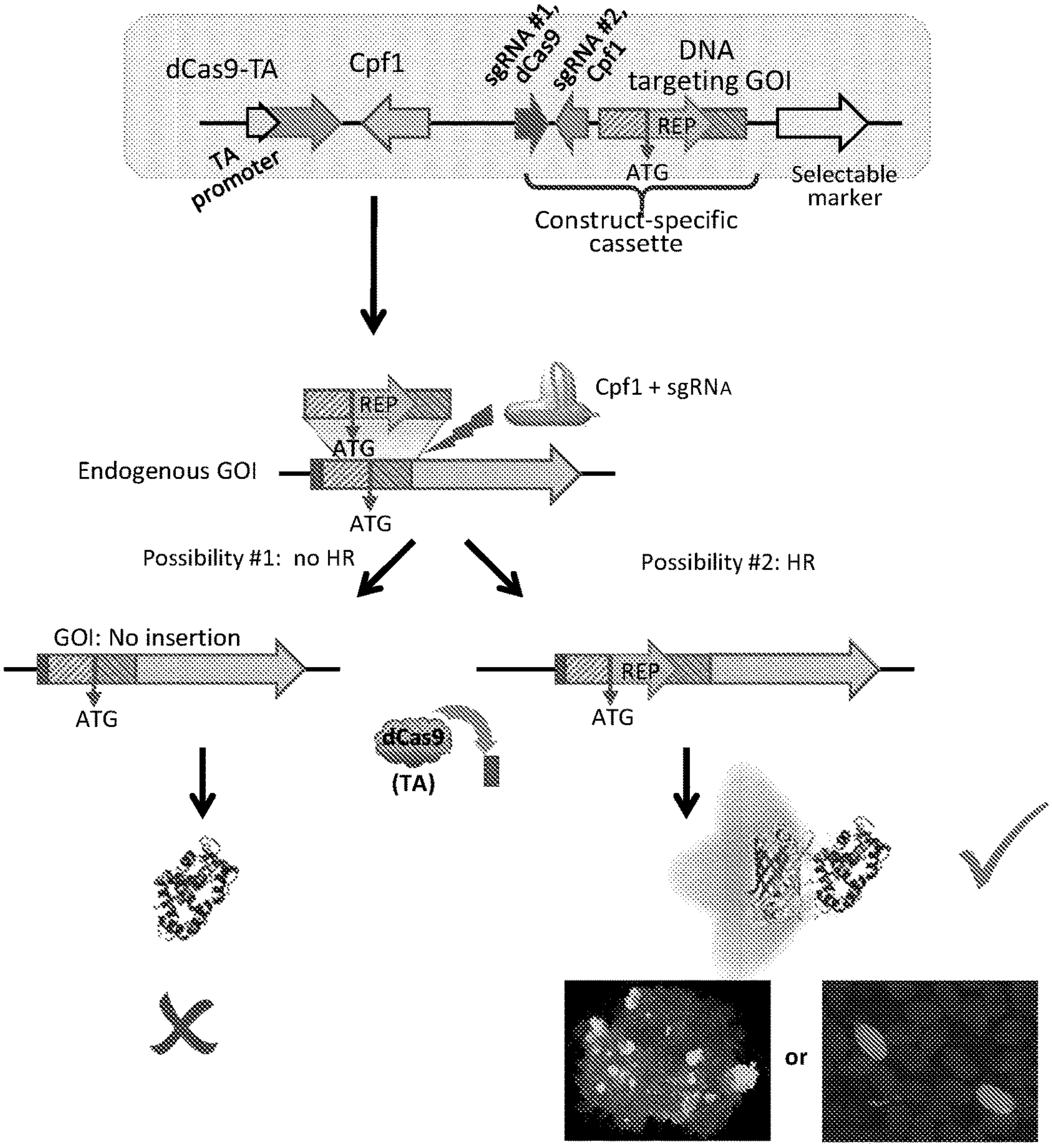
FIG. 5 schematically depicts a large-scale version of the strategy depicted in FIG. 1, but using a library of cassettes incorporating a transcriptional activator and insertion fragment specific to the gene of interest (GOI). Such cassettes may be generated in parallel (100s to 1000s of distinct cassettes) and incorporated into a construct encoding the additional components of the homologous recombination composition (T-DNA or other transformed DNA).

Preferably, each homologous recombination composition comprises a programmable nucleic acid modification system and a programmable transcription activator having a nucleic acid targeting domain that may be provided independently of their respective nuclease, nickase or transcription activation domains. For instance, if the homologous recombination system is a CRISPR nuclease system, each homologous recombination composition may comprise a guide RNA which may be provided independently from the other components of the CRISPR nuclease homologous recombination system. Similarly, if the transcription activation system is based on a CRISPR nuclease system modified to lack all nuclease activity, each homologous recombination composition may comprise a guide RNA which may be provided independently from the other components of the transcription activation system. This arrangement would enable libraries of nucleic acid constructs comprising a cassette of a donor polynucleotide, a gRNA of the CRISPR-based nucleic acid modification system, and a gRNA of the CRISPR-based transcription activation system, all specific for generating a homologous recombination event at a specific nucleic acid locus. Such cassettes may be generated in parallel (100s to 1000s of distinct cassettes) and incorporated into a construct for introducing into cells. Additional components of the CRISPR-based nucleic acid modification system and the CRISPR-based transcription activation system may then be provided independently. Preferably, all the components of the homologous recombination system are encoded on a modular homologous recombination construct comprising a backbone encoding the additional components of the CRISPR-based nucleic acid modification system and the CRISPR-based transcription activation system, and further comprising a cassette comprising the donor polynucleotide, a nucleic acid sequence encoding the gRNA of the CRISPR-based nucleic acid modification system, and a nucleic acid sequence encoding the gRNA of the CRISPR-based transcription activation system. Generating libraries of nucleic acid constructs using such modular constructs would only require inserting into the backbone cassettes comprising the donor polynucleotides and nucleic acid sequences encoding the gRNAs, wherein each cassette is specific for a target nucleic acid locus. One aspect of such a strategy may be as schematically depicted in FIG. 5. Other strategies for generating libraries of constructs may be envisioned by individuals skilled in the art.

VI. Kits

A further aspect of the present disclosure provides kits comprising one or more recombination compositions detailed above in Section I, wherein each of the homologous recombination compositions targets a distinct nucleic acid locus. The one or more homologous recombination compositions may be encoded by a system of one or more nucleic acid constructs described above in Section III. Alternatively, the kit may comprise one or more cells comprising one or more homologous recombination compositions, a system of one or more nucleic acid constructs, or combinations thereof.

The kits may further comprise transfection reagents, cell growth media, selection media, in-vitro transcription reagents, nucleic acid purification reagents, protein purification reagents, buffers, and the like. The kits provided herein generally include instructions for carrying out the methods detailed below. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

A "genetically modified" cell refers to a cell in which the nuclear, organellar or extrachromosomal nucleic acid sequences of a cell has been modified, i.e., the cell contains at least one nucleic acid sequence that has been engineered to contain an insertion of at least one nucleotide, a deletion of at least one nucleotide, and/or a substitution of at least one nucleotide.

The terms "genome modification" and "genome editing" refer to processes by which a specific nucleic acid sequence in a genome is changed such that the nucleic acid sequence is modified. The nucleic acid sequence may be modified to comprise an insertion of at least one nucleotide, a deletion of at least one nucleotide, and/or a substitution of at least one nucleotide. The modified nucleic acid sequence is inactivated such that no product is made. Alternatively, the nucleic acid sequence may be modified such that an altered product is made.

The term "heterologous" refers to an entity that is not native to the cell or species of interest.

The terms "nucleic acid" and "polynucleotide" refer to a deoxyribonucleotide or ribonucleotide polymer, in linear or circular conformation. For the purposes of the present disclosure, these terms are not to be construed as limiting with respect to the length of a polymer. The terms may encompass known analogs of natural nucleotides, as well as nucleotides that are modified in the base, sugar and/or phosphate moieties. In general, an analog of a particular nucleotide has the same base-pairing specificity, i.e., an analog of A will base-pair with T. The nucleotides of a nucleic acid or polynucleotide may be linked by phosphodiester, phosphothioate, phosphoramidite, phosphorodiamidate bonds, or combinations thereof.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

As used herein, the terms "target site", "target sequence", or "nucleic acid locus" refer to a nucleic acid sequence that defines a portion of a nucleic acid sequence to be modified or edited and to which a homologous recombination composition is engineered to target.

The terms "upstream" and "downstream" refer to locations in a nucleic acid sequence relative to a fixed position. Upstream refers to the region that is 5' (i.e., near the 5' end of the strand) to the position, and downstream refers to the region that is 3' (i.e., near the 3' end of the strand) to the position.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences may also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981).

This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

As various changes could be made in the above-described cells and methods without departing from the scope of the invention, it is intended that all matter contained in the above description and in the examples given below, shall be interpreted as illustrative and not in a limiting sense.

EXAMPLES

The publications discussed above are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes may be made in the disclosure and still obtain a like or similar result without departing from the spirit and scope of the disclosure, therefore all matter set forth is to be interpreted as illustrative and not in a limiting sense.

Example 1. Visualization of Repair Template Integration

Figure 8:
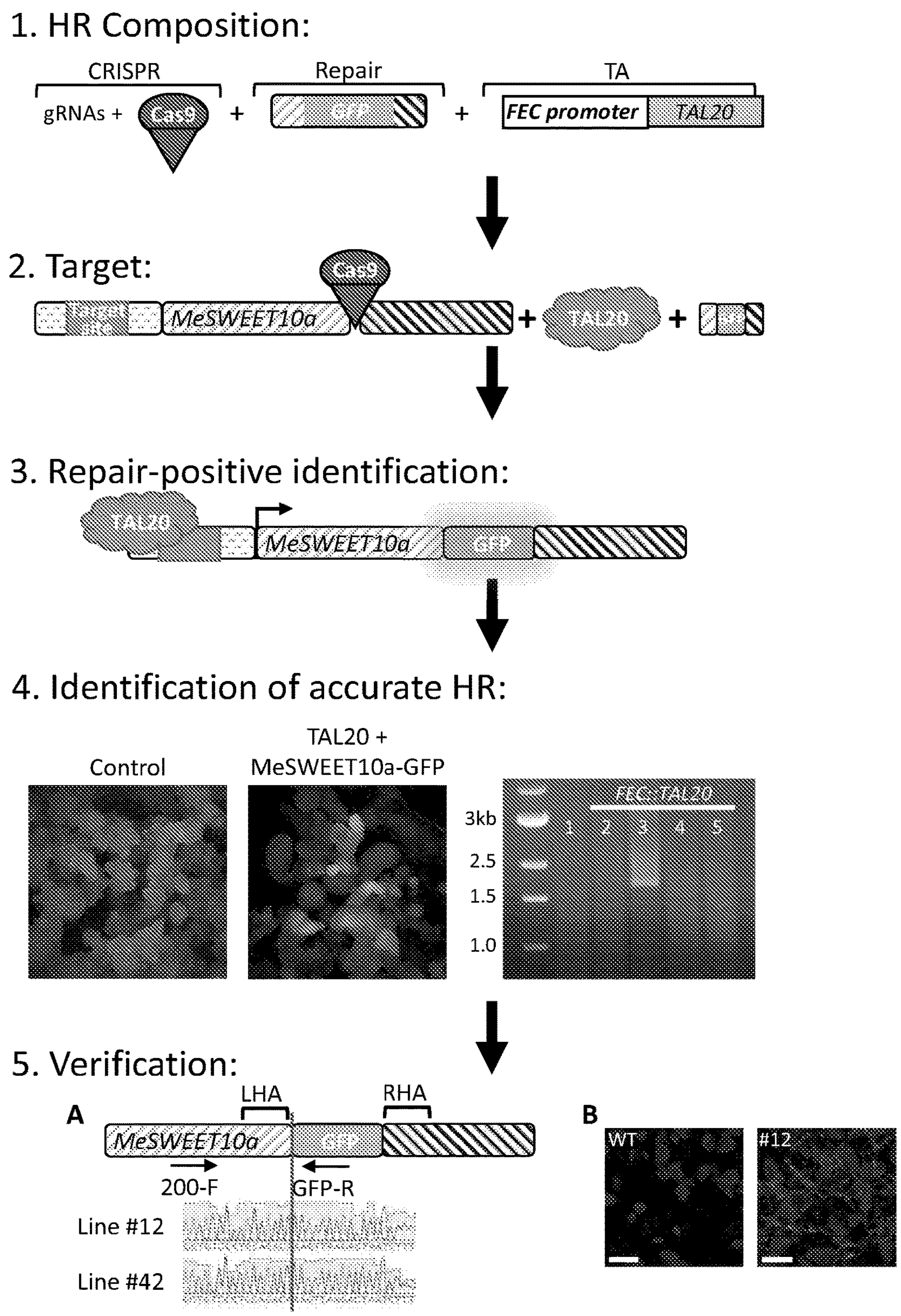
FIG. 8 depicts demonstrated use of a strategy used to fuse a GFP reporter at the C-terminus of the MeSWEET10a protein in cassava callus tissue. Panel 1: Schematic representation of the contents of DNA constructs used to introduce GFP at the endogenous MeSWEET10a locus of cassava. Represented are the CRISPR components (gRNAs and Cas9 nuclease), repair template (GFP plus left and right homology arms (LHA, RHA)), and tissue-specific (FEC) promoter driving expression of a MeSWEET10a-specific transcriptional activator (TAL20). Panel 2: Schematic representation of the repair process depicting digestion site of Cas9 nuclease at the cassava MeSWEET10a target, the TAL20 transcriptional activator, and the repair template. Panel 3: Accurate homologous recombination is visualized when the TAL20 transcription activator induces the expression of the MeSWEET10a/GFP fusion protein. Panel 4: Identification of accurate homologous recombination. Left: Fluorescence imaging photomicrographs of cassava callus tissue. A: negative control cassava callus transformed with a plasmid comprising all the components of homologous recombination composition except the transcription activator. B: positive control cassava callus transformed with all components of the homologous recombination composition, including the TAL20 transcription activator. Fluorescent cells, indicating an accurate homologous recombination event, are only seen in the positive control. Right: PCR screening for GFP integration at MeSWEET10a locus. Lane 1 control genomic DNA, lanes 2-5 GFP-positive lines with a FEC-specific promoter driving TAL20 expression. Panel 5: Depicts a schematic representation of sequence verification. (A) Top: Repair-positive lines identified through PCR were sequenced using a forward primer (200-F) outside of the left homology arm (LHA) and a GFP-specific reverse primer (GFP-R). Bottom: Sequence traces of two cassava cell lines identified as having homologous recombination. The red line indicates the predicted junction of MeSWEET10a and GFP, confirmed by sequencing depicted by the sequence traces. (B) Confocal images of WT and repair positive line #12 leaves depicting MeSWEET10a-GFP ER localization. Pseudocolors: red=chlorophyll, green=GFP. Scale bars=10 μm.

A homologous recombination composition was used to fuse a GFP reporter at the C-terminus of the MeSWEET10 protein in cassava callus tissue. As shown in FIG. 8, the strategy comprised providing combining the CRISPR-Cas9 binary vector (containing two gRNAs targeted to the C-terminus of MeSWEET10a), a repair template (GFP flanked by ~850 bp homology arms) and the TAL20 transcriptional activator, driven by the tissue-specific (FEC) promoter.

Specifically, two plasm ids were prepared. One plasmid (169; SEQ ID NO: 13) comprises a construct for expressing the AtCas9 protein in combination with the csy4 CRISPR RNA processing protein from Pseudomonas aeruginosa under the control of the 35S promoter. The sequence for expressing AtCas9 protein is codon optimized for expression in *Arabidopsis*. The plasmid further comprises a construct for expressing the two gRNAs of the system under the control of the CYMLV promoter. A first gRNA targets MeSWEET10a just before stop codon and a second gRNA targets region just after MeSWEET10a stop codon. The two gRNAs are separated by csy4 binding sites for processing the two gRNAs. The plasmid also comprises the donor nucleic acid sequence (repair template), an expression construct for expression of a selectable reporter (NPTII), and T-DNA borders for transformation into cassava cells. A construct for expressing the TAL20 transcription activator under the control of the 35S promoter was inserted into the 169 plasmid to generate plasmid 171 (SEQ ID NO: 15). As such, plasmid 171 provides all the components of the homologous recombination composition, whereas plasmid 169 may be used as a control wherein the transcription activator is not present.

The composition was introduced into cassava via *Agrobacterium*-mediated transformation using T-DNA, and callus cells (specifically Friable Embryonic Calli, or FEC cells) were screened for GFP signal using epifluorescence. Through this screening process, five GFP-positive sectors of FEC cells were identified out of many hundreds that harbored the T-DNA. PCR and sequencing confirmed integration of GFP in frame at the C-terminus of MeSWEET10a, just 5' of the stop codon, exactly matching the repair template, in one of these FEC populations (FIG. 8, Panel 5A). This demonstrates that Cas9-facilitated sequence integration coupled with a TA step is a viable strategy for identifying edited cells. Further, correct recombination was confirmed in leaves of cassava generated using the identified GFP-positive sectors of FEC cells (FIG. 8, Panel 5B). This was particularly encouraging since this work was done both in tissue culture (a typical step for plant transformation), and in a species that is relatively far from being a model for plants.

Example 2. Visualization of Repair Template Integration Using a Tissue Specific Promoter A similar experiment as described in Example 1 may be performed, wherein the transcription activator is under the control of the Manes.17G095200 callus-specific promoter.

Two plasmids are prepared. One plasmid comprises a construct for expressing the AtCas9 protein in combination with the csy4 CRISPR RNA processing protein, a construct for expressing the two gRNAs of the system under the control of the CYMLV promoter, and the donor nucleic acid sequence. The plasmid is plasmid 169 described in Example 1 above. A construct for expressing the TAL20 transcription activator under the control of the tissue-specific Manes.17G095200 is inserted into the 169 plasmid to generate plasmid 170 (SEQ ID NO: 14). Plasmid 170 provides all the components of the homologous recombination composition, whereas plasmid 169 is used as a control wherein the transcription activator is not present.

When used in cassava callus cells, the callus transformed with the 169 plasmid only shows background fluorescence. Conversely, cells transformed with the 170 plasmid shows some cells clearly expressing GFP over the background fluorescence, thereby identifying accurate homologous recombination events in these cells.

Example 3. Knock-Outs by Knock-Ins: Using a Homologous Recombination Composition for Single-Gene Knockouts and Large Deletions A powerful, but perhaps counterintuitive strategy is to use a homologous recombination composition to generate knockouts ("KOs"), reducing the time and cost associated with genotyping regenerated plants. Typically, when aiming to KO a gene with CRISPR, regenerants must be genotyped unless the phenotype is obvious. Using the homologous recombination composition of the disclosure, stop codons are introduced downstream of the fluorescent protein fusion (FIG. 3A). In the case of a single gene knockout, the reporter replaces the start codon, and/or 5', 3', or internal coding exons, or adds a new terminated exon, in each case disrupting the function of the GOI and leaving in its place a visual marker that is induced by the TA in the tissue in which screening is performed. This accelerates the process of genotyping, since the disruption results from successful HR.

A homologous recombination composition is also used to generate deletions or sequence replacements between two genes of interest. This is achieved by targeting a pair of genes that are located some distance from one another and using HR to simultaneously introduce two reporters into these genes, while also replacing the intervening sequence with a different nucleic acid sequence. Expression of both reporters after HR indicates replacement of the original nucleic acid sequence between the two genes of interest (FIG. 3B). Expression of both reporters after HR indicates replacement of the original nucleic acid sequence between the two genes of interest.

Example 4. Tagging Specific Members of Highly Similar Multi-Gene Families

Specific members of highly similar multigene families are tagged using 5' or 3' UTR differences. In this application of the disclosed compositions, an RNA aptamer strategy as described below is used. This strategy is used to tag specific members of the PPR gene family in *Arabidopsis*, as it is comprised of hundreds of members with a wide range of similarities, and family members are targets of many small RNAs.

Example 4. Tagging Using Fluorescence RNA Aptamers

When relying on fluorescent proteins, non-coding RNAs cannot be tagged (without introducing an ORF). Fluorescent RNA are non-coding, fluorophore-binding RNA sequences of ~70 nt. The ability to tag an RNA transcript in situ and track these transcripts is a powerful technique for studying gene function.

Intended uses of fluorescent aptamers includes: (i) use to direct homologous recombination with small translational epitope fusions in the 5' or 3' UTRs adjacent to a gene of interest (FIG. 6), or (ii) insert aptamers in noncoding RNAs, including miRNAs (FIG. 7). Use to tag the 5' or 3' UTRs adjacent to a gene of interest may be as described in Example 1.

For noncoding RNAs, a composition is used to tag TAS3 IncRNA and miR390 in cassava, *Setaria*, and *Arabidosis* with RNA aptamers that may ultimately allow the localization and quantification of these molecules, using super resolution microscopy. An additional application includes RNA capture. For example, an additional RNA sequence is added for RNA capture, such as the BoxB sequence bound by lambda protein "N".

For tagging IncRNA modifications, numerous possibilities are used, and are as schematically described in FIG. 7. Of particular interest is conversion of 22-nt miRNA to 21-nt miRNAs (FIG. 7, panel C), altering their ability to trigger secondary siRNAs at target transcripts. In cassava and many eudicots, miR482 that targets NB-LRR R-genes is of particular interest. Poorly understood reproductive phasiRNAs in grasses are also be targeted to insert a BoxB RNA binding site (for lambda N) into a Setaria phasiRNA precursor, into both the 3' and 5' precursor ends (FIG. 7, panels E and F).

Example 5. High-Throughput Applications: the Potential to Target Every Gene in a Genome Methods of the disclosure are upscaled to whole-genome applications. In other words, whole-genome methods have long been deployed in *Arabidopsis*. Disclosed compositions are used to create genome-wide knock-in libraries in diverse species in addition to *Arabidopsis*. Compositions are used to knock-out or epitope tag every gene in a species recalcitrant to homologous recombination. Constructs for a composition of the disclosure are prepared wherein gene-specific components are concentrated into a single cassette that can be synthesized and cloned in bulk (FIG. 5). Agilent oligo synthesis using inkjet printing-based methods are used to synthesize up to 100,000+ custom oligos that are over 150 nt in length. Overlapping oligos are designed, and annealing plus a fill-in reaction are performed to generate thousands of unique fragments of 100's of nts that are cloned en masse, to create a complex library for bulk transformation in methods of the disclosure. Methods are used for either forward (screening of anonymous but targeted knockout libraries) or reverse (epitope tagging, or deconvoluted knockout lines) genetics approaches. For deconvolution, the gene-specific construct is amplified and sequenced using a multi-dimensional pooling strategy. This type of strategy has been implemented in numerous large-scale CRISPR library screens in cell lines but has not been implemented in species recalcitrant to homologous recombination such as plants. To enable this application, constructs are constructed to co-locate the gene-specific components, flanked by BsaI sites, for intermediate cloning to a vector with Gateway cloning sites, enabling highly efficient ligation. Colocating components specific to the GOI (see FIG. 5) enables production on one cassette of two guide RNAs (Cpf1 for HR, dCas9 for TA), and the insertion fragment) totaling ~350 bp.

In an initial experiment, a set of 48 target genes are targeted, for which cassettes are synthesized using overlapping oligos in 96-well plates. This 48-plex library is transformed by dip transformation into *Arabidopsis* or flax, and is de-convoluted by sequencing the gene-specific cassette for each resulting line before assessing the target site modifications. For the 48 genes, components of a single pathway are selected, such as small RNA biogenesis (Dicers, AGOs, etc.).

What is claimed is:

1. A homologous recombination composition for identifying a cell comprising an accurate homologous recombination event, the recombination composition comprising:

a. a homologous recombination system comprising:

i. an expression construct comprising a promoter operably linked to a nucleic acid sequence encoding a programmable nucleic acid modification system, wherein the modification system targets a nucleic acid locus in a gene of interest; and ii. a donor polynucleotide comprising a nucleic acid sequence encoding a reporter flanked by regions homologous to the nucleic acid locus in the gene of interest; and b. an expression construct comprising a promoter operably linked to a nucleic acid sequence encoding a transcription activation system specific for inducing expression of the gene of interest;

wherein expression of the transcription activation system in a cell induces expression of the gene of interest, wherein expression of the transcription activation system in the cell does not induce expression of the reporter indicates an inaccurate recombination event, wherein expression of the transcription activation system in the cell induces expression of the reporter indicates an accurate recombination event, and wherein expression of the reporter identifies a cell comprising an accurate homologous recombination event.

2. The composition of claim 1, wherein the programmable nucleic acid modification system is an RNA-guided clustered regularly interspersed short palindromic repeats (CRISPR)/CRISPR-associated (Cas) (CRISPR/Cas) nuclease system, a CRISPR/Cpf1 nuclease system, a zinc finger nuclease (ZFN), a transcription activator-like effector nuclease (TALEN), a meganuclease, or a programmable DNA binding domain linked to a nuclease domain.

3. The composition of claim 1, wherein the gene of interest is a protein coding gene and the homologous recombination event results in the reporter fused in frame with an open reading frame of the gene of interest, the reporter completely or partially replacing a coding sequence of the gene of interest, introduction of the reporter into an intron of the gene of interest, or in an untranslated region of a protein-producing gene of interest, or introduction of a stop codon such that expression of the gene of interest results in the expression of an unfused reporter, fusing the reporter at an N terminus, C terminus, or internally to a polypeptide fragment encoded by a partial open reading frame of the gene of interest.

4. The composition of claim 1, wherein the gene of interest is a protein-coding gene and the reporter is a fluorescent RNA aptamer.

5. The composition of claim 1, wherein the transcription activation system comprises a programmable endonuclease modified to lack all nuclease activity, a catalytically inactive Ago endonuclease, a catalytically inactive meganuclease, or a transcription activator-like effectors (TALEs) nucleic acid binding protein.

6. The composition of claim 1, wherein the donor polynucleotide further encodes sequence modifications in the gene of interest at or near a nucleic acid locus.

7. The composition of claim 1, wherein the gene of interest is a RNA coding gene and the homologous recombination further introduces a small RNA target site to knock out a IncRNA, one or more polymorphisms at 5' or 3' sequences of a miRNA precursor, or introduces in phase insertions or replacements of tasiRNAs or phasiRNAs in a tasi/phasiRNAs.

8. The composition of claim 1, wherein a promoter of the gene of interest is replaced with a heterologous promoter.

9. The composition of claim 8, wherein the donor polynucleotide comprises a first nucleic acid sequence targeting a first nucleic acid locus for replacing endogenous promoter control sequences, and a second nucleic acid sequence at a second target nucleic acid locus for introducing the reporter in the gene of interest.

10. The composition of claim 1, wherein an intergenic nucleic acid sequence between two genes of interest is modified.

11. The composition of claim 10, wherein the donor polynucleotide encodes:

a. a first replacement polynucleotide comprising a first reporter flanked by regions of homology to a first nucleic acid locus in a first gene of interest;

b. a second replacement polynucleotide comprising a second reporter flanked by regions of homology to a second nucleic acid locus in a second gene of interest; and c. an intergenic construct flanked by the first replacement polynucleotide and the second replacement polynucleotide.

12. The composition of claim 1, wherein the transcription activation system and the homologous recombination system are encoded on one or more expression constructs.

13. The composition of claim 12, wherein expression of the transcription activation system is controlled by a tissue specific promoter.

14. The composition of claim 13, wherein the tissue specific promoter expresses the transcription activation system in screenable tissue.

15. A library of homologous recombination compositions comprising two or more homologous recombination compositions of claim 1, wherein each of the two or more homologous recombination compositions targets a distinct nucleic acid locus.

16. The library of claim 15, wherein the library targets all genes in a genome of a cell.

17. The library of claim 15, wherein each of the two or more homologous recombination compositions knocks out a distinct gene of interest.

18. The library of claim 15, wherein the homologous recombination system is a CRISPR nuclease system and the transcription activation system is based on a CRISPR nuclease system.

19. The library of claim 15, wherein the library comprises two or more homologous recombination constructs, wherein each construct comprises:

a. a nucleic acid cassette specific for a distinct nucleic acid locus and comprising a nucleic acid expression construct encoding a gRNA of a CRISPR-based nucleic acid modification system specific for the nucleic acid locus, a nucleic acid expression construct encoding a gRNA of a CRISPR-based transcription activation system, and a donor polynucleotide encoding a reporter flanked by regions homologous to the nucleic acid locus; and b. a modular homologous recombination construct comprising a backbone encoding additional components of the CRISPR-based nucleic acid modification system and the CRISPR-based transcription activation system.

20. A kit for generating one or more accurate homologous recombination events in a cell, the kit comprising one or more homologous recombination compositions of claim 1, wherein each of the homologous recombination compositions targets a distinct nucleic acid locus.

* * * * *